(12) United States Patent
O'Neill et al.

(10) Patent No.: US 12,214,015 B2
(45) Date of Patent: *Feb. 4, 2025

(54) USE OF C-TYPE NATRIURETIC PEPTIDE VARIANTS TO TREAT OSTEOARTHRITIS

(71) Applicant: BIOMARIN PHARMACEUTICAL INC., Novato, CA (US)

(72) Inventors: Charles A. O'Neill, Novato, CA (US); Todd M. Oppeneer, Novato, CA (US); Jason K. Pinkstaff, Novato, CA (US)

(73) Assignee: BIOMARIN PHARMACEUTICAL INC., Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/541,992

(22) Filed: Dec. 3, 2021

(65) Prior Publication Data

US 2022/0160836 A1    May 26, 2022

Related U.S. Application Data

(63) Continuation of application No. 15/779,049, filed as application No. PCT/US2016/065520 on Dec. 8, 2016, now Pat. No. 11,202,819.

(60) Provisional application No. 62/264,682, filed on Dec. 8, 2015.

(51) Int. Cl.
| | |
|---|---|
| *A61K 38/22* | (2006.01) |
| *A61K 9/19* | (2006.01) |
| *A61K 31/573* | (2006.01) |
| *A61K 31/728* | (2006.01) |
| *A61P 19/02* | (2006.01) |
| *C07K 14/58* | (2006.01) |

(52) U.S. Cl.
CPC ............... *A61K 38/22* (2013.01); *A61K 9/19* (2013.01); *A61K 31/573* (2013.01); *A61K 31/728* (2013.01); *A61K 38/2242* (2013.01); *A61P 19/02* (2018.01); *C07K 14/58* (2013.01)

(58) Field of Classification Search
CPC .... A61K 38/22; A61K 38/2242; C07K 14/58; A61P 19/02
See application file for complete search history.

(56) References Cited

U.S. PATENT DOCUMENTS

| | | | | |
|---|---|---|---|---|
| 7,642,243 B2 * | 1/2010 | Nakao | ..................... | A61P 31/10 |
| | | | | 514/21.4 |
| 2010/0297021 A1 * | 11/2010 | Wendt | ....................... | A61P 9/00 |
| | | | | 435/69.7 |
| 2010/0331256 A1 | 12/2010 | Wendt et al. | | |
| 2012/0164142 A1 | 6/2012 | Crine et al. | | |

FOREIGN PATENT DOCUMENTS

| | | |
|---|---|---|
| EP | 1743653 A1 | 1/2007 |
| EP | 1759710 A1 | 3/2007 |
| KR | 2007-0017366 A | 2/2007 |
| WO | WO-2009/067639 A2 | 5/2009 |

OTHER PUBLICATIONS

Uthman et al., Postgrad. Med. J., 2003, vol. 79:449-453.*
Tanishi et al., J. Orthop. Sci., May 2014, vol. 19(3):429-436 (abstract).*
Wendt et al., Neutral endopeptidase-resistant C-type natriuretic peptide variant represents a new therapeutic approach for treatment of fibroblast growth factor receptor 3-related dwarfism, J. Pharmacol. Exp. Ther., 353(1):132-49 (Apr. 2015).
Uthman et al., Intra-articular therapy in osteoarthritis, Postgrad Med. J., 79(934):449-53 (2003).
Tanishi et al., Usefulness of urinary CTX-II and NTX-I in evaluating radiological knee osteoarthritis : the Matsudai knee osteoarthritis survey, J. Orthop. Sci., 19(3):429-36 (2014).
Peake et al., Controlled release of C-type natriuretic peptide by microencapsulation dampens proinflammatory effects induced by IL-1β in cartilage explants, Biomacromolecules, 16(2):524-31 (2015).
Peake et al., C-type natriuretic peptide signalling drives homeostatic effects in human chondrocytes, 465(4):784-9 (2015).
Bukulmez et al., Protective effects of C-type natriuretic peptide on linear growth and articular cartilage integrity in a mouse model of inflammatory arthritis, Arthritis Rheumatol., 66(1):78-89 (2014).
International Search Report and Written Opinion, International Application No. PCT/US2016/065520, Sep. 22, 2017.

* cited by examiner

*Primary Examiner* — Xiaozhen Xie
(74) *Attorney, Agent, or Firm* — MARSHALL, GERSTEIN & BORUN LLP

(57) ABSTRACT

The disclosure relates to the use of variants of C-type natriuretic peptide (CNP) to treat osteoarthritis, to ameliorate one or more symptoms of osteoarthritis, and to treat disorders having an osteoarthritis component.

18 Claims, 27 Drawing Sheets

Specification includes a Sequence Listing.

USE OF C-TYPE NATRIURETIC PEPTIDE VARIANTS TO TREAT OSTEOARTHRITIS

CROSS-REFERENCE TO RELATED APPLICATIONS

The present application is a continuation of U.S. patent application Ser. No. 15/779,049, filed May 24, 2018, now U.S. Pat. No. 11,202,819, issued Dec. 21, 2021, which is the U.S. national phase application, pursuant to 35 U.S.C. § 371, of PCT international application Ser. No.: PCT/US2016/065520, filed Dec. 8, 2016, which claims the priority benefit of U.S. Provisional Patent Application No. 62/264,682, filed Dec. 8, 2015, herein incorporated by reference in their entireties.

INCORPORATION BY REFERENCE OF MATERIAL SUBMITTED ELECTRONICALLY

The Sequence Listing, which is a part of the present disclosure, is submitted with the specification as a computer readable file. The name of the file containing the Sequence Listing is "49583A_Seqlisting.txt", which was created on Feb. 15, 2024 and is 74,587 bytes in size. The subject matter of the Sequence Listing is incorporated herein in its entirety by reference.

FIELD OF THE DISCLOSURE

The disclosure relates to the use of variants of C-type natriuretic peptide (CNP) to treat osteoarthritis, to ameliorate one or more symptoms of osteoarthritis, and to treat disorders having an osteoarthritis component.

BACKGROUND OF THE DISCLOSURE

Osteoarthritis (OA) is a degenerative disease of the joints. It is the most prevalent joint disease affecting an estimated 10% of men and 18% of women over the age of sixty. Indeed, OA is one of the leading causes of pain and disability in aging adults. It is a complex disease that does not have a single cause but rather is the final endpoint of many predisposing factors including joint trauma, age, and obesity. The most common pathologic alterations in OA joints are degradation of articular cartilage, inflammation of the synovium, increase in subchondral bone depth, and the development of osteophytes. Current pharmaceutical therapies for OA target the inflammatory aspects of the disease but do not target the underlying degeneration or the altered architecture of the joint. These anti-inflammatory treatments only offer temporary pain relief. In contrast, treatments that would decrease or reverse the degeneration of the joint are thought to have longer lasting and favorable effects on patient pain and mobility. Accordingly, there is a need for pharmaceutical agents that can decrease joint degeneration and/or restore articular cartilage and joint structure in OA patients.

C-type natriuretic peptide (CNP) (GenBank Accession No. NP_077720, for the CNP precursor protein, NPPC) is a small, single-chain peptide that is widely expressed—most prominently by the central nervous system, reproductive tract, bone, and endothelium of blood vessels. CNP binds two distinct receptors: the natriuretic peptide receptor B (NPR-B) and the natriuretic peptide receptor C (NPR-C). NPR-B is a member of the membrane bound guanylyl cyclase multi-gene family and produces the second messenger cyclic guanosine monophosphate (cGMP) when activated by CNP binding. In contrast, NPR-C does not have any intracellular signaling domains and instead functions to clear natriuretic peptides from the extracellular space. Thus, when CNP binds to NPR-C the receptor internalizes and delivers the CNP to a lysosome where it is degraded, thereby lowering the effective extracellular concentration of CNP.

CNP is initially produced from the natriuretic peptide precursor C (NPPC) gene as a 126-amino acid pre-pro polypeptide. Removal of the signal peptide yields pro-CNP, and further cleavage by the endoprotease furin generates a biologically active 53-amino acid peptide (CNP-53), which is secreted and further processed to produce the mature 22-amino acid peptide (CNP-22). CNP-53 and CNP-22 differ in their distribution, with CNP-53 primarily found in tissues while CNP-22 is mainly found in plasma and cerebrospinal fluid. The predominant CNP form in cartilage is currently unknown. Both CNP-53 and CNP-22 bind to NPR-B with similar kinetics and both induce cGMP production in a dose-dependent manner. Downstream signaling mediated by cGMP influences a diverse array of biological processes, including endochondral ossification. Accordingly, elevated or depressed levels of any of the components in this pathway may lead to aberrant bone or cartilage growth. For example, knockout of either CNP or NPR-B in mouse models results in animals having a dwarfed phenotype with shorter long bones and vertebrae. In addition, mutations in human NPR-B that block CNP signaling result in dwarfism. In contrast, mice engineered to produce elevated levels of CNP display elongated long bones and vertebrae.

The therapeutic potential of CNP is limited by its short half-life. CNP is cleared by two mechanisms: 1) through the action of membrane-bound neutral endopeptidase (NEP), which rapidly degrades CNP, and 2) through binding NPR-C which targets CNP to lysosomes where it is degraded. These two clearance mechanisms are responsible for the short half-life of CNP (~2.6 min.). To increase CNP concentration above the levels typically found in human plasma (~5 pM), continuous infusion has been necessary, which severely limits its therapeutic potential. To overcome this problem, CNP variants with longer half-lives have been developed. Given its potential role in stimulating cartilage growth, CNP variants represent a novel class of therapeutics for offering longer lasting relief to OA patients.

SUMMARY OF THE DISCLOSURE

The present disclosure relates to use of CNP variants to treat primary or secondary osteoarthritis or one or more osteoarthritis-associated symptom(s). It is disclosed herein that administration of CNP variants can lead to improved range of motion of affected joints and slowed or decreased osteoarthritis-associated damage to cartilage, calcified cartilage, or subchondral bone in treated animals. In various embodiments, the CNP variant is Gly-CNP-37 or Pro-Gly-CNP-37.

In various embodiments, the disclosure provides a method of treating primary or secondary osteoarthritis or one or more osteoarthritis-associated symptom(s), comprising administering a CNP variant or composition comprising a CNP variant to a subject in need thereof, wherein the administering treats primary or secondary osteoarthritis or said one or more symptom(s) of the disease. Also contemplated is a method of increasing growth of cartilage, calcified cartilage or subchondral bone in a subject, comprising administering a CNP variant or composition comprising a CNP variant to a subject in need thereof. The disclosure also contemplates a method of slowing, preventing or inhibiting osteoarthritis-associated degeneration of cartilage, calcified cartilage or subchondral bone, comprising administering a CNP variant or composition comprising a CNP variant to a subject in need thereof. In addition the disclosure provides a method of increasing the range of motion or decreasing the stiffness in a joint affected by osteoarthritis, comprising administering a CNP variant to a subject in need thereof.

In various embodiments, the CNP variant is selected from the group consisting of:

```
(Pro-Gly-CNP37)
                                         (SEQ ID NO: 1)
PGQEHPNARKYKGANKKGLSKGCFGLKLDRIGSMSGLGC;

(Gly-CNP-37)
                                         (SEQ ID NO: 2)
GQEHPNARKYKGANKKGLSKGCFGLKLDRIGSMSGLGC;

(Gly-CNP53)
                                         (SEQ ID NO: 3)
GDLRVDTKSRAAWARLLQEHPNARKYKGANKKGLSKGCFGLKLDRIGSMSG
LGC;

(Pro-CNP53)
                                         (SEQ ID NO: 4)
PDLRVDTKSRAAWARLLQEHPNARKYKGANKKGLSKGCFGLKLDRIGSMSG
LGC;

(Met-CNP53)
                                         (SEQ ID NO: 5)
MDLRVDTKSRAAWARLLQEHPNARKYKGANKKGLSKGCFGLKLDRIGSMSG
LGC;

[CNP-53(M48N)]
                                         (SEQ ID NO: 6)
DLRVDTKSRAAWARLLQEHPNARKYKGANKKGLSKGCFGLKLDRIGSNSGL
GC;

(CNP-52)
                                         (SEQ ID NO: 7)
LRVDTKSRAAWARLLQEHPNARKYKGANKKGLSKGCFGLKLDRIGSMSGL
GC;

(CNP-51)
                                         (SEQ ID NO: 8)
RVDTKSRAAWARLLQEHPNARKYKGANKKGLSKGCFGLKLDRIGSMSGL
GC;

(CNP-50)
                                         (SEQ ID NO: 9)
VDTKSRAAWARLLQEHPNARKYKGANKKGLSKGCFGLKLDRIGSMSGLGC;

(CNP-49)
                                        (SEQ ID NO: 10)
DTKSRAAWARLLQEHPNARKYKGANKKGLSKGCFGLKLDRIGSMSGLGC;

(CNP-48)
                                        (SEQ ID NO: 11)
TKSRAAWARLLQEHPNARKYKGANKKGLSKGCFGLKLDRIGSMSGLGC;

(CNP-47)
                                        (SEQ ID NO: 12)
KSRAAWARLLQEHPNARKYKGANKKGLSKGCFGLKLDRIGSMSGLGC;

(CNP-46)
                                        (SEQ ID NO: 13)
SRAAWARLLQEHPNARKYKGANKKGLSKGCFGLKLDRIGSMSGLGC;

(CNP-45)
                                        (SEQ ID NO: 14)
RAAWARLLQEHPNARKYKGANKKGLSKGCFGLKLDRIGSMSGLGC;

(CNP-44)
                                        (SEQ ID NO: 15)
AAWARLLQEHPNARKYKGANKKGLSKGCFGLKLDRIGSMSGLGC;

(CNP-43)
                                        (SEQ ID NO: 16)
AWARLLQEHPNARKYKGANKKGLSKGCFGLKLDRIGSMSGLGC;

(CNP-42)
                                        (SEQ ID NO: 17)
WARLLQEHPNARKYKGANKKGLSKGCFGLKLDRIGSMSGLGC;

(CNP-41)
                                        (SEQ ID NO: 18)
ARLLQEHPNARKYKGANKKGLSKGCFGLKLDRIGSMSGLGC;

(CNP-40)
                                        (SEQ ID NO: 19)
RLLQEHPNARKYKGANKKGLSKGCFGLKLDRIGSMSGLGC;

(CNP-39)
                                        (SEQ ID NO: 20)
LLQEHPNARKYKGANKKGLSKGCFGLKLDRIGSMSGLGC;

(CNP-38)
                                        (SEQ ID NO: 21)
LQEHPNARKYKGANKKGLSKGCFGLKLDRIGSMSGLGC;

(CNP-37)
                                        (SEQ ID NO: 22)
QEHPNARKYKGANKKGLSKGCFGLKLDRIGSMSGLGC;

(CNP-36)
                                        (SEQ ID NO: 23)
EHPNARKYKGANKKGLSKGCFGLKLDRIGSMSGLGC;

(CNP-35)
                                        (SEQ ID NO: 24)
HPNARKYKGANKKGLSKGCFGLKLDRIGSMSGLGC;

(CNP-34)
                                        (SEQ ID NO: 25)
PNARKYKGANKKGLSKGCFGLKLDRIGSMSGLGC;

(CNP-33)
                                        (SEQ ID NO: 26)
NARKYKGANKKGLSKGCFGLKLDRIGSMSGLGC;

(CNP-32)
                                        (SEQ ID NO: 27)
ARKYKGANKKGLSKGCFGLKLDRIGSMSGLGC;

(CNP-31)
                                        (SEQ ID NO: 28)
RKYKGANKKGLSKGCFGLKLDRIGSMSGLGC;

(CNP-30)
                                        (SEQ ID NO: 29)
KYKGANKKGLSKGCFGLKLDRIGSMSGLGC;

(CNP-29)
                                        (SEQ ID NO: 30)
YKGANKKGLSKGCFGLKLDRIGSMSGLGC;

(CNP-28)
                                        (SEQ ID NO: 31)
KGANKKGLSKGCFGLKLDRIGSMSGLGC;

(CNP-27)
                                        (SEQ ID NO: 32)
GANKKGLSKGCFGLKLDRIGSMSGLGC;

(CNP-26)
                                        (SEQ ID NO: 33)
ANKKGLSKGCFGLKLDRIGSMSGLGC;

(CNP-25)
                                        (SEQ ID NO: 34)
NKKGLSKGCFGLKLDRIGSMSGLGC;
```

```
(CNP-24)
                                        (SEQ ID NO: 35)
KKGLSKGCFGLKLDRIGSMSGLGC;

(CNP-23)
                                        (SEQ ID NO: 36)
KGLSKGCFGLKLDRIGSMSGLGC;

(CNP-21)
                                        (SEQ ID NO: 38)
LSKGCFGLKLDRIGSMSGLGC;

(CNP-20)
                                        (SEQ ID NO: 39)
SKGCFGLKLDRIGSMSGLGC;

(CNP-19)
                                        (SEQ ID NO: 40)
KGCFGLKLDRIGSMSGLGC;

(CNP-18)
                                        (SEQ ID NO: 41)
GCFGLKLDRIGSMSGLGC;

[CNP-37(M32N)]
                                        (SEQ ID NO: 43)
QEHPNARKYKGANKKGLSKGCFGLKLDRIGSNSGLGC;

(Pro-CNP-37)
                                        (SEQ ID NO: 44)
PQEHPNARKYKGANKKGLSKGCFGLKLDRIGSMSGLGC;

(Met-CNP-37)
                                        (SEQ ID NO: 45)
MQEHPNARKYKGANKKGLSKGCFGLKLDRIGSMSGLGC;

(Gly-CNP-37)
                                        (SEQ ID NO: 2)
GQEHPNARKYKGANKKGLSKGCFGLKLDRIGSMSGLGC;

[Gly-CNP-37(M32N)]
                                        (SEQ ID NO: 46)
GQEHPNARKYKGANKKGLSKGCFGLKLDRIGSNSGLGC;

(Met-Gly-CNP-37)
                                        (SEQ ID NO: 47)
MGQEHPNARKYKGANKKGLSKGCFGLKLDRIGSMSGLGC;

(HSA-CNP-27)
                                        (SEQ ID NO: 48)
GHKSEVAHRFKGANKKGLSKGCFGLKLDRIGSMSGLGC;

[HSA-CNP-27(M22N)]
                                        (SEQ ID NO: 49)
GHKSEVAHRFKGANKKGLSKGCFGLKLDRIGSNSGLGC;

(Pro-HSA-CNP-27)
                                        (SEQ ID NO: 50)
PGHKSEVAHRFKGANKKGLSKGCFGLKLDRIGSMSGLGC;

(Met-HSA-CNP-27)
                                        (SEQ ID NO: 51)
MGHKSEVAHRFKGANKKGLSKGCFGLKLDRIGSMSGLGC;

[CNP-27(K4,5,9R)]
                                        (SEQ ID NO: 52)
GANRRGLSRGCFGLKLDRIGSMSGLGC;

[CNP-27(K4,5,9R, M22N)]
                                        (SEQ ID NO: 53)
GANRRGLSRGCFGLKLDRIGSNSGLGC;

[Pro-CNP-27(K4,5,9R)]
                                        (SEQ ID NO: 54)
PGANRRGLSRGCFGLKLDRIGSMSGLGC;

[Met-CNP-27(K4,5,9R)]
                                        (SEQ ID NO: 55)
MGANRRGLSRGCFGLKLDRIGSMSGLGC;

[PEG1K-CNP-27(K4,5,9R)]
                                        (SEQ ID NO: 56)
PEG1K-GANRRGLSRGCFGLKLDRIGSMSGLGC;

[PEG1K-CNP-27(K4,5,9R, M22N)]
                                        (SEQ ID NO: 57)
PEG1K-GANRRGLSRGCFGLKLDRIGSNSGLGC;

[PEG1K-Pro-CNP-27(K4,5,9R)]
                                        (SEQ ID NO: 58)
PEG1K-PGANRRGLSRGCFGLKLDRIGSMSGLGC;

[PEG1K-Met-CNP-27(K4,5,9R)]
                                        (SEQ ID NO: 59)
PEG1K-MGANRRGLSRGCFGLKLDRIGSMSGLGC;

[PEO12-CNP-27(K4,5,9R)]
                                        (SEQ ID NO: 60)
PEO12-GANRRGLSRGCFGLKLDRIGSMSGLGC;

[PEO12-CNP-27(K4,5,9R, M22N)]
                                        (SEQ ID NO: 61)
PEO12-GANRRGLSRGCFGLKLDRIGSNSGLGC;

[PEO12-Pro-CNP-27(K4,5,9R)]
                                        (SEQ ID NO: 62)
PEO12-PGANRRGLSRGCFGLKLDRIGSMSGLGC;

[PEO12-Met-CNP-27(K4,5,9R)]
                                        (SEQ ID NO: 63)
PEO12-MGANRRGLSRGCFGLKLDRIGSMSGLGC;

[PEO24-CNP-27(K4,5,9R)]
                                        (SEQ ID NO: 64)
PEO24-GANRRGLSRGCFGLKLDRIGSMSGLGC;

[PEO24-CNP-27(K4,5,9R, M22N)]
                                        (SEQ ID NO: 65)
PEO24-GANRRGLSRGCFGLKLDRIGSNSGLGC;

[PEO24-Pro-CNP-27(K4,5,9R)]
                                        (SEQ ID NO: 66)
PEO24-PGANRRGLSRGCFGLKLDRIGSMSGLGC;
and

[PEO24-Met-CNP-27(K4,5,9R)]
                                        (SEQ ID NO: 67)
PEO24-MGANRRGLSRGCFGLKLDRIGSMSGLGC.
```

In various embodiments, the increase in cartilage, calcified cartilage, or subchondral bone growth or slowing of cartilage, calcified cartilage, or subchondral bone degeneration is observed in the subject's knee, shoulder, elbow, finger, hand, wrist, hips, neck, ankle, spine, and/or lower back of the subject. In various embodiments, cartilage damage or growth is analyzed by chondrocyte death/loss, proteoglycan (PG) loss, and collagen loss or fibrillation.

Also provided is a method of increasing the range of motion in a joint in a subject with osteoarthritis, comprising administering a CNP variant to a subject in need thereof. In various embodiments, the CNP variant increases range of motion as measured by hip flexion, hip extension, hip abduction, hip adduction, knee flexion, or knee extension by 10%, 20%, 25%, 30%, 35%, 40%, 45%, 50%, 55%, 60%, 65%, 70% or 75%. It is also contemplated that administration of the CNP variant improves symptoms of arthritis, including osteoarthritis, as assessed on various patient and pain scales, such as those described in further detail in the Detailed Description. In various embodiments, the CNP variant is Gly-CNP-37 or Pro-Gly-CNP-37.

Yet another embodiment of the present invention is directed to a method of preventing, inhibiting or slowing the growth or formation of osteophytes in a mammal, comprising administering a CNP variant to a subject in need thereof. In various embodiments, the osteophyte formation or growth is associated with osteoarthritis in the subject. Osteophyte formation or growth, and the prevention or inhibition of formation or growth thereof, may be determined by physical measurement of the size of an osteophyte over time and during the course of a CNP variant treatment regimen. In various embodiments, the CNP variant is Gly-CNP-37 or Pro-Gly-CNP-37.

Another embodiment of the present invention is directed to a method of preventing, inhibiting or slowing abnormal growth of subchondral or epiphyseal trabecular bone in a mammal, comprising administering a CNP variant to a subject in need thereof. In one aspect, the abnormal growth of subchondral or epiphyseal bone is manifested by thickening of the bone. In another aspect, the abnormal growth of the subchondral or epiphyseal trabecular bone is associated with osteoarthritis, osteoporosis or osteosclerosis. In various embodiments, the CNP variant is Gly-CNP-37 or Pro-Gly-CNP-37.

Yet another embodiment of the present invention is directed to a method of preventing, inhibiting or slowing synovial inflammation (i.e., synovitis) in a mammal, comprising administering a CNP variant to a subject in need thereof. In one aspect, the synovial inflammation is manifested at least by mononuclear cell infiltration into an affected joint. In another aspect, the synovial inflammation is associated with osteoarthritis. In various embodiments, the CNP variant is Gly-CNP-37 or Pro-Gly-CNP-37.

In one embodiment, the CNP variant is administered intraarticularly. It is also contemplated that that the CNP variant is administered by other routes. Exemplary routes of administration include, but are not limited to subcutaneous, intraarticular, intravenous, intra-arterial, intraperitoneal, intramuscular, intradermal, intraperitoneal, intramuscular, intradermal, intrathecal, topical, transdermal, or transmucosal administration.

In another embodiment, the CNP variant is administered in response to joint trauma or injury. In a further embodiment the CNP variant is administered within a month of joint trauma or injury. In another embodiment the CNP variant is administered within a week of joint trauma or injury. In other embodiments the CNP variant is administered after cartilage degeneration has occurred.

In various embodiments, the disclosure provides a method of assessing the effect of a CNP variant on the level of at least one cartilage-associated biomarker in a subject having osteoarthritis, comprising assaying the level of at least one cartilage-associated biomarker in a biological sample from a subject having osteoarthritis that has been administered a CNP peptide or variant. In one embodiment, the CNP variant is administered to the subject before assaying the level of the at least one cartilage-associated biomarker.

In various embodiments, contemplated herein is a method of treating osteoarthritis or one or more osteoarthritis-associated symptom(s) or manifestation(s), comprising administering a CNP variant to a subject, wherein the subject was identified as having elevated levels of at least one cartilage-associated biomarkers. In various embodiments, the at least one cartilage-associated biomarker is selected from the group consisting of CNP, cGMP, propeptides of collagen type II and fragments thereof, collagen type II and fragments thereof, syndecan-3, annexin VI, proliferating cell nuclear antigen (PCNA), propeptides of type I procollagen (PINP) and fragments thereof, collagen type I and fragments thereof, and aggrecan chondroitin sulfate.

In various embodiments, the disclosure provides for use of a composition comprising a CNP variant. In one embodiment, the composition further comprises a pharmaceutically acceptable excipient, carrier or diluent. In one embodiment, the composition is a lyophilized formulation prepared from a formulation that comprises a citric acid/citrate buffer or an acetic acid/acetate buffer having a pH from about 4 to about 6.

Also contemplated is a method of treatment as described herein further comprising administration of a second agent. In various embodiments, the second agent is selected from the group consisting of an anti-inflammatory agent, an NSAID, a corticosteroid, and hyaluronic acid.

In various embodiments, the CNP variants used in the methods can be attached to a hydrophobic acid, or can be attached to one or more hydrophobic acids. Non-limiting examples of hydrophobic acids include straight-chain or branched, saturated or unsaturated $C_5$-$C_{12}$ carboxylic acids (e.g., pentanoic acid, heptanoic acid, etc.) and natural fatty acids. The hydrophobic acids can be attached to the N-terminus, the C-terminus, and/or the side chain of one or more amino acid residues. In one embodiment, the hydrophobic acid is conjugated to the N-terminus.

In yet another embodiment, the CNP variants used in the methods are chimera, or fusion proteins, comprising a CNP variant, and a cleavable peptide or protein, or peptide tag. Exemplary cleavable proteins or peptides include, but are not limited to, histidine (e.g., hexa-His) tags; TAF12: human transcription factor TAF12; KSI: ketosteroid isomerase; MBP: maltose-binding protein; ß-Gal: ß-galactosidase; GST: glutathione-S-transferase; Trx: thioredoxin; CBD: chitin binding domain; BMPM: BMP-2 mutation, SUMO, CAT, TrpE, staphylococcal protein A, streptococcal proteins, starch-binding protein, cellulose-binding domain of endoglucanase A, cellulose-binding domain of exoglucanase Cex, biotin-binding domain, recA, Flag, c-Myc, poly(His), poly(Arg), poly(Asp), poly(Gln), poly(Phe), poly(Cys), green fluorescent protein, red fluorescent protein, yellow fluorescent protein, cyan fluorescent protein, biotin, avidin, streptavidin, antibody epitopes, and fragments thereof.

In various embodiments, the CNP variant may be a monomer or a dimer. In a related embodiment the monomers of dimeric CNP variants can be attached N-terminus to N-terminus via a linker or no linker, N-terminus to C-terminus via a linker or no linker, or C-terminus to C-terminus via a linker or no linker.

In any of the embodiments disclosed herein, the CNP variants may have substantially the same or better biological activity than wild-type CNP-22. For example, the CNP variants may retain at least 50%, 60%, 70%, 80%, 90%, 95% or more of the activity of wild-type CNP-22, or may have greater activity than CNP-22, e.g., with respect to interaction with NPR-B to stimulate the generation of cGMP. Alternatively, or in addition, the CNP variants may retain at least 50%, 60%, 70%, 80%, 90%, 95% or more of the activity of wild-type CNP-22, or may have greater activity than CNP-22, with respect to regulating endochondral bone growth and chondrocyte activity, including but not limited to chondrocyte proliferation, chondrocyte differentiation, inhibition of the mitogen activated protein (MAP) kinase/MEK (Raf-1) kinase signaling pathway, and promoting endochondral ossification. In any of the embodiments described herein, the CNP variants may comprise an amino acid sequence that is at least 40%, 50%, 60%, 70%, 80%, 90%, 95% or more identical to amino acids 6-22 or 1-22 of wild-type CNP-22.

In various embodiments, the CNP variants can optionally have conjugation(s) or extension(s), e.g., at the N- and/or C-terminus to facilitate cartilage targeting, reduce renal clearance, and/or increase resistance to NEP degradation. Such conjugation(s) or extension(s) can comprise molecules or sequences formed or derived from, e.g., polyAsp, polyGlu, cartilage-targeting peptides, sialoprotein, PEGs, carbohydrates, hydrophobic acids, NPPC or non-CNP (poly) peptides, or combinations thereof.

It is further contemplated that the CNP variants can be conjugated to a hydrophobic polymeric or non-polymeric moiety, such as, e.g., heptanoic acid, pentanoic acid, or fatty acids. The hydrophobic moiety can be conjugated to the side chain of an amino acid residue, including but not limited to a lysine, a serine, a cysteine or a threonine, or can be attached to the N-terminus and/or C-terminus of the CNP variant.

In various embodiments, the CNP variants useful in the methods have a pI in the range from about 8 to about 10.5 or from about 8.5 to about 10.

In various embodiments, the disclosure provides for use of a pharmaceutical composition comprising a CNP variant, optionally another biologically active agent, and optionally a pharmaceutically acceptable excipient, carrier or diluent. In various embodiments, the compositions are sterile pharmaceutical compositions suitable for parenteral administration. In some embodiments, the compositions comprise substantially pure CNP variant, e.g. at least about 90% or 95% pure. In some embodiments, the compositions contain less than about 5%, 4%, 3%, 2%, 1% or 0.5% contaminants, such as other human proteins, porcine proteins, or CNP-53 or fragments thereof (other than the desired CNP variant). In certain embodiments, the sterile composition is administered to a subject for treating or preventing any of the CNP-responsive conditions or disorders disclosed herein.

CNP variants useful herein advantageously retain CNP activity and exhibit increased serum half-life. Retention of CNP activity can be shown, for example, as retention of desired in vivo biological effect, or retention of at least about 50%, 60%, 70%, 80%, 90%, 95% or at least about 100% of the cGMP stimulating activity of CNP-22, under the same concentration (e.g., 1 µM of CNP peptide or greater than the ED80). In some embodiments, CNP variants exhibit at least about 1.5-fold, 2-fold, 3-fold, 4-fold, 5-fold, 10-fold, 15-fold, 20-fold, 25-fold, 30-fold, 35-fold or 40-fold increase in serum half-life compared to CNP-22.

In a related embodiment, the CNP variants described herein have increased NEP resistance and exhibit increased half-life compared to wild-type CNP-22. In one embodiment, the half-life of the CNP variants is increased by about 20%, 30%, 40%, 50%, 60%, 70%, 80%, 90%, 95%, 96%, 97%, 98%, 99% or about 100% compared to wild-type CNP-22.

In certain embodiments, the CNP variants described herein for use in the methods increase cGMP production in vitro, increase cGMP production in vivo, increase in vivo the level of one or more biomarkers associated with cartilage or bone formation or growth, increase resistance to NEP cleavage in vitro, increase plasma or serum half-life in vivo, increase bioavailability in vivo, or increase the growth or regeneration of cartilage in vivo, or effect combinations of such increases, by about 1.5-fold, about 2-fold, about 2.5-fold, about 3-fold, about 3.5-fold, about 4-fold, about 4.5-fold, or about 5-fold or more compared to wild-type CNP-22.

In various embodiments, the CNP variants described herein are administered at a dose in the range from about 5 or 10 nmol/kg to about 300 nmol/kg, or from about 20 nmol/kg to about 200 nmol/kg. In some embodiments, the CNP variants are administered at a dose of about 5, 10, 15, 20, 25, 30, 35, 40, 45, 50, 55, 60, 65, 70, 75, 80, 85, 90, 95, 100, 125, 150, 175, 200, 210, 220, 230, 240, 250, 260, 270, 280, 290, 300, 350, 400, 450, 500, 750, 1000, 1250, 1500, 1750 or 2000 nmol/kg or other dose deemed appropriate by the treating physician. In other embodiments, the CNP variants are administered at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750 or 800 µg/kg, or about 1 mg/kg, 1.25 mg/kg, 1.5 mg/kg, 2 mg/kg or other dose deemed appropriate by the treating physician.

In various embodiments, the CNP variants are administered in a single treatment or in multiple doses. The multiple doses may be administered daily, or in multiple doses over the course of treatment. In various embodiments, it is contemplated that the CNP variant is administered, in a single dose or in multiple doses, daily, every other day, every 3 days, 2 times per week, 3 times per week, weekly, bi-weekly, every 3 weeks, monthly, every 6 weeks, every 2 months, every 3 months or as deemed appropriate by a treating physician.

In certain embodiments, administration of the CNP variant is adjusted to allow for periods of preventative or therapeutic treatment followed by a recovery period. For example, the CNP variant may be administered intraarticularly, subcutaneously, intravenously, or by another mode daily or multiple times per week for a period of time, followed by a period of no treatment, then the cycle is repeated. In some embodiments, the initial period of treatment (e.g., administration of the CNP variant daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the CNP variant is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

In additional embodiments, the disclosure provides a method of treating osteoarthritis or a disorder having an osteoarthritis-associated symptom, comprising administering a CNP variant to a subject, and monitoring the level of at least one cartilage-associated biomarker in the subject (e.g., in a biological sample from the subject), wherein an increase or decrease in the level of the cartilage-associated biomarker indicates a therapeutic effect of the CNP variant on the subject. In some embodiments, when the level of a biomarker increases in association with cartilage, calcified cartilage or subchondral bone formation or growth, an increase in the level of that biomarker indicates a therapeutic effect of the CNP variant on the subject. In other embodiments, when the level of a biomarker decreases in association with cartilage, calcified cartilage or subchondral bone formation or growth, a decrease in the level of that biomarker indicates a therapeutic effect of the CNP variant on the subject.

In further embodiments, the therapeutic method further comprises adjusting the amount (or dose) or frequency of administration of the CNP variant, wherein:
(i) the amount (or dose) or frequency of administration of the CNP variant is increased if the level of the at least one cartilage-associated biomarker is below a target level, where the level of the biomarker increases in association with cartilage formation or growth; or (ii) the amount (or dose) or frequency of administration of the CNP variant is decreased if the level of the at least one cartilage-associated biomarker is above a target level, where the level of the biomarker increases in association with cartilage formation or growth; or (iii) the amount (or dose) or frequency of administration of the CNP variant is increased if the level of the at least one cartilage-associated biomarker is above a target level, where the level of the biomarker decreases in association with cartilage formation or growth; or (iv) the amount (or dose) or frequency of administration of the CNP variant is decreased if the level of the at least one cartilage-associated biomarker is below a target level, where the level of the biomarker decreases in association with cartilage formation or growth.

It is contemplated that the target level of a biomarker refers to the level or range of levels of the biomarker that is associated with therapeutic effect in the subject and/or beneficial effect in alleviating or ameliorating symptoms of the disorder or condition. In certain embodiments, a level of a biomarker above or below a target level may be deleterious to the subject.

In other embodiments, the disclosure contemplates a method for assessing the effect of administration of a CNP variant on cartilage, calcified cartilage or subchondral bone formation or growth. In one embodiment, the method provides for assaying or measuring the level of at least one cartilage-associated biomarker in a subject that has been administered a CNP variant in order to assess the effect of the CNP variant on cartilage, calcified cartilage or subchondral bone formation and growth in vivo. In a related embodiment, an increase in the level of the at least one cartilage-associated biomarker may indicate that administration of a CNP variant has a positive effect on cartilage, calcified cartilage or subchondral bone formation or growth and is a useful treatment for osteoarthritis and other cartilage-related diseases or disorders associated with decreased CNP activity. Exemplary cartilage-associated biomarkers include, but are not limited to, CNP (e.g., endogenous level of CNP-22 or CNP-53), cGMP, propeptides of collagen type II and fragments thereof, collagen type II and fragments thereof, syndecan-3, annexin VI, proliferating cell nuclear antigen (PCNA), propeptides of type I procollagen (PINP) and fragments thereof, collagen type I and fragments thereof, and aggrecan chondroitin sulfate.

In further embodiments, the disclosure contemplates a method for assessing the effect of a CNP variant on the level of at least one cartilage-associated biomarker in a subject, comprising assaying or measuring the level of the cartilage-associated biomarker in a biological sample from a subject that has been administered a CNP variant. In some embodiments, the method further comprises administering the CNP variant to the subject before assaying or measuring the level of the cartilage-associated biomarker.

In some embodiments of the methods (e.g., therapeutic, diagnostic and assay methods) relating to cartilage-associated biomarkers, the CNP variant is Gly-CNP-37, also referred to as Gly-CNP-37, or any of the CNP peptides and variants described herein, including the CNP variants shown herein. In certain embodiments of such methods, the CNP peptide or variant is not CNP-22 or CNP-53. In a particular embodiment, the CNP variant is Pro-Gly-CNP-37.

Use of any of the foregoing CNP variants described herein in preparation of a medicament for treatment of osteoarthritis and symptoms or other physiological manifestations described herein associated with osteoarthritis is also contemplated. Syringes, e.g., single use or pre-filled syringes, sterile sealed containers, e.g. vials, bottle, vessel, and/or kits or packages comprising any of the foregoing peptides or polypeptides, optionally with suitable instructions for use, are also contemplated.

It is understood that each feature described herein is a non-limiting, illustrative example of any of the aspects of the disclosure and, as such, is meant to be combinable with any other features described herein. For example, where features are described with language such as "one embodiment," "certain embodiments," "some embodiments," "further embodiment," "specific exemplary embodiments," and/or "another embodiment," each of these features may be combined with any other feature, or features, described herein without having to list every possible combination. Where examples of values falling within ranges are disclosed, any of these examples are contemplated as possible endpoints of a range, any and all numeric values between such endpoints are contemplated, and any and all combinations of upper and lower endpoints are envisioned.

DETAILED DESCRIPTION OF THE DISCLOSURE

Figure 1:
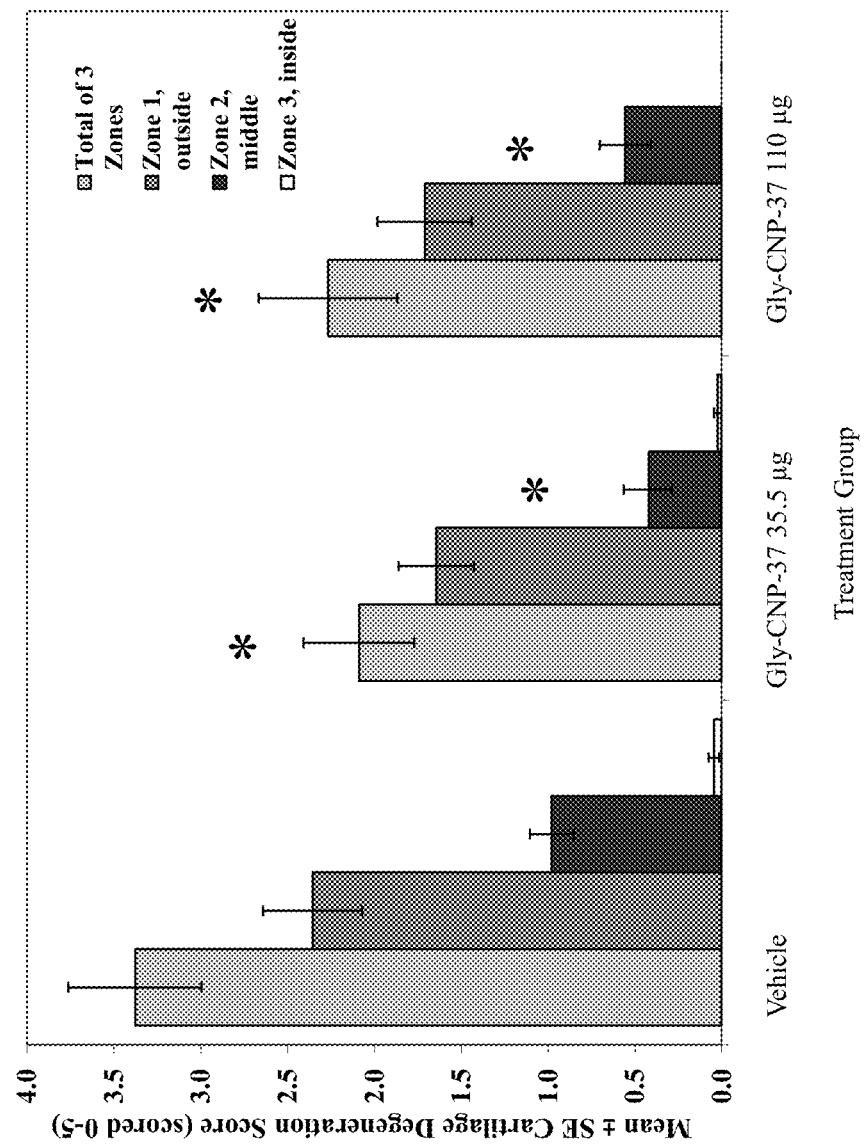
FIG. 1 illustrates that Gly-CNP-37 administration at low (35.5 µg) or high dose (110 µg) showed significant reduction in cartilage degeneration in the tibia. *$p \leq 0.05$ ANOVA to vehicle.

The present disclosure relates to methods of using CNP variants to treat osteoarthritis, one or more symptoms of osteoarthritis and other disorders having an osteoarthritis-associated symptom or component.

A. DEFINITIONS

Unless otherwise stated, the following terms used in this application, including the specification and claims, have the definitions given below.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

Definition of standard chemistry terms may be found in reference works, including Carey and Sundberg, Advanced Organic Chemistry, $3^{rd}$ Edition, Vols. A and B (Plenum Press, New York 1992). The practice of the present disclosure may employ, unless otherwise indicated, certain conventional methods of synthetic organic chemistry, mass spectrometry, preparative and analytical chromatography, protein chemistry, biochemistry, recombinant DNA technology and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., $4^{th}$ Edition, 2004); Sambrook, et al., Molecular Cloning: A Laboratory Manual ($2^{nd}$ Edition, 1989); Methods In Enzymology (S. Colowick and N. Kaplan eds., Academic Press, Inc.); Remington's Pharmaceutical Sciences, $18^{th}$ Edition (Easton, Pennsylvania: Mack Publishing Company, 1990).

All publications, patents and patent applications cited herein, whether supra or infra, are hereby incorporated by reference in their entirety.

"Polypeptide" and "protein" refer to a polymer composed of amino acid residues, related naturally occurring structural variants, and synthetic non-naturally occurring analogs thereof, linked via peptide bonds or peptide bond isosteres. Synthetic polypeptides can be synthesized, for example, using an automated polypeptide synthesizer. The terms "polypeptide" and "protein" are not limited to a minimum length of the product.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to substitution of an amino acid in a polypeptide with a functionally, structurally or chemically similar natural or unnatural amino acid. In one embodiment, the following groups each contain natural amino acids that are conservative substitutions for one another:
  (1), Alanine (A) Serine (S), Threonine (T);
  (2) Aspartic acid (D), Glutamic acid (E);
  (3) Asparagine (N), Glutamine (Q);
  (4) Arginine (R), Lysine (K);
  (5) Isoleucine (I), Leucine (L), Methionine (M), Valine (V); and
  (6) Phenylalanine (F), Tyrosine (Y), Tryptophan (W).

In another embodiment, the following groups each contain natural amino acids that are conservative substitutions for one another:
  (1) Glycine (G), Alanine (A);
  (2) Aspartic acid (D), Glutamic acid (E);
  (3) Asparagine (N), Glutamine (Q);
  (4) Arginine (R), Lysine (K);
  (5) Isoleucine (I), Leucine (L), Methionine (M), Valine (V), Alanine (A);
  (6) Phenylalanine (F), Tyrosine (Y), Tryptophan (W); and
  (7) Serine (S), Threonine (T), Cysteine (C).

In a further embodiment, amino acids may be grouped as set out below.
  (1) hydrophobic: Met, Ala, Val, Leu, Be, Phe, Trp;
  (2) neutral hydrophilic: Cys, Ser, Thr, Asn, Gln;
  (3) acidic: Asp, Glu;
  (4) basic: His, Lys, Arg;
  (5) residues that influence backbone orientation: Gly, Pro; and
  (6) aromatic: Trp, Tyr, Phe, His.

In one embodiment, the CNP variants described herein useful in the methods are generated via recombinant means, using a polynucleotide encoding a CNP variant. CNP variants expressed by such polynucleotides may be produced by methods including growing host cells in culture medium under conditions suitable for expression of the polynucleotide encoding a CNP variant, and isolating the expression product from the host cells or culture medium. Actual expression products may vary slightly from the encoded protein product depending on any post-translational processing.

"Polynucleotide" refers to a polymer composed of nucleotide units. Polynucleotides include naturally occurring biopolymers (with respect to molecular type but not necessarily biopolymer sequence), such as deoxyribonucleic acid ("DNA") and ribonucleic acid ("RNA") as well as nucleic acid analogs. "cDNA" refers to a DNA that is complementary or identical to an mRNA, in either single stranded or double stranded form.

"Expression control sequence" refers to a nucleotide sequence that regulates the expression of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), 3'UTRs, enhancers, transcription terminators, a start codon (i.e., ATG), splicing signals for introns, and stop codons.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Chimera" as used herein refers to a polynucleotide or polypeptide comprising at least two heterologous polynucleotide or polypeptide sequences (i.e. derived from different sources or not associated with each other as a naturally-occurring sequence) which are directly or indirectly attached or linked together using techniques commonly known in the art, e.g., recombinant expression or chemical crosslinking. In one embodiment, the heterologous sequence can comprise a protein or peptide directly or indirectly linked to a CNP variant, including proteins or peptides which are cleavable from the CNP variant. In a related embodiment, CNP variants are chimera as described herein.

In certain embodiments, chimeras include CNP fusion proteins comprising a cleavable carrier protein or peptide tag. The term "cleavable carrier protein" or "cleavable peptide tag" refers to a peptide or polypeptide sequence that may be fused, directly or indirectly via a linker, to a heterologous polypeptide sequence, and is removable from the heterologous sequence using an agent that cleaves or separates the cleavable peptide or polypeptide from the heterologous polypeptide or protein. In some embodiments, the cleavable carrier protein or peptide tag improves generation, purification and/or detection of the fusion protein or the heterologous polypeptide. Exemplary cleavable carrier proteins and peptide tags include, but are not limited to, human transcription factor TAF12 (TAF12), ketosteroid isomerase (KSI), maltose-binding protein (MBP), ß-galactosidase (ß-Gal), glutathione-S-transferase (GST), thioredoxin (Trx), chitin-binding domain (CBD), BMP-2 mutation (BMPM), SUMO, CAT, TrpE, staphylococcal protein A, streptococcal proteins, starch-binding protein, cellulose-binding domain of endoglucanase A, cellulose-binding domain of exoglucanase Cex, biotin-binding domain, recA, FLAG®, c-Myc, poly(His), poly(Arg), poly(Asp), poly(Gln), poly(Phe), poly(Cys), green fluorescent protein, red fluorescent protein, yellow fluorescent protein, cyan fluorescent protein, biotin, avidin, streptavidin, antibody epitopes, and fragments thereof.

By "range of motion" is meant the full movement potential of a joint, typically its range of flexion and/or extension. Range of motion is typically measured using a goniometer and presented in degrees of arc. Any method of measurement known to those of skill in the art can be used to measure the range of motion of a subject's joint. One illustrative method of measuring range of motion of a joint is provided, for example, by Norkin, C. C. and White D. J., Measurement of joint motion: a guide to goniometry (F.A. Davis Company, $2^{nd}$ ed. Philadelphia) (1995).

By "joint stiffness" is meant the sensation of difficulty in moving a joint or the apparent loss of range of motion of a joint A "cleaving agent" is an agent that is useful to cleave or separate, e.g., a cleavable peptide or polypeptide from a heterologous polypeptide or protein. Cleaving agents include, but are not limited to, palladium, cyanogen bromide (CNBr), formic acid, hydroxylamine, clostripain, thrombin, chymotrypsin, trypsin, tryp sin-like proteases, carboxypeptidase, enterokinase (enteropeptidase), Kex 2 protease, Omp T protease, Factor Xa protease, subtilisin, proTEV, SUMO protease, V8 protease, HIV protease, rhinovirus protease, furilisin protease, IgA proteases, human Pace protease, collagenase, Nia protease, poliovirus 2 Apro protease, poliovirus 3C protease, genenase, furin, elastase, Proteinase K, pepsin, rennin (chymosin), microbial aspartic proteases, papain, calpain, chymopapain, ficin (ficain), bromelain (bromelase), cathespisin B, caspases, thermolysin, Endoprotease Arg-C, Endoprotease Glu-C, Endoprotease Lys-C, kallikrein, and plasmin.

The terms "identical" and percent "identity", in the context of two or more polynucleotide or polypeptide sequences, refer to two or more sequences or subsequences that are the same or have a specified percentage of nucleotides or amino acid residues that are the same, when compared and aligned for maximum correspondence.

The phrase "substantially homologous" or "substantially identical", in the context of two nucleic acids or polypeptides, generally refers to two or more sequences or subsequences that have at least 40%, 50%, 60%, 70%, 80%, 90%, 95%, or 98% nucleotide or amino acid residue identity, when globally aligned.

Global alignment of sequences for comparison is conducted using the EMBOSS Needle program (e.g., as implemented by EMBL-EBI via web interface) using default parameters (for protein: matrix=BLOSUM62, Gap open=10, gap extend=0.5, output format=pair, end gap penalty=false, end gap open=10, end gap extend=0.5; for nucleotide, matrix=DNAfull, Gap open=10, gap extend=0.5, output format=pair, end gap penalty=false, end gap open=10, end gap extend=0.5)

A further indication that two nucleic acid sequences or polypeptides are substantially homologous or identical is that the polypeptide encoded by the first nucleic acid is immunologically cross reactive with the polypeptide encoded by the second nucleic acid, as described below. Thus, a polypeptide is typically substantially identical to a second polypeptide, for example, where the two polypeptides differ only by conservative substitutions. Another indication that two nucleic acid sequences are substantially identical is that the two molecules hybridize to each other under stringent conditions, as described herein.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. In various embodiments, the species of interest comprises at least about 70%, 75%, 80%, 85%, 90%, 95%, or 98% of the macromolecular species present in the composition on a molar or weight basis. The object species is purified to "essential homogeneity" if contaminant macromolecular species cannot be detected in the composition by conventional detection methods. Solvent species, small molecules (<500 Daltons), stabilizers (e.g., BSA), and elemental ion species are not considered macromolecular species for purposes of this definition. In an embodiment, the compounds of the disclosure are substantially pure or isolated. In another embodiment, the compounds of the disclosure are substantially pure or isolated with respect to the macromolecular starting materials used in their production. In yet another embodiment, the pharmaceutical compositions of the disclosure comprise a substantially pure or isolated CNP variant admixed with one or more pharmaceutically acceptable excipients, carriers or diluents, and optionally with another biologically active agent.

"Wild-type" (wt) is a term referring to the natural form, including sequence, of a polynucleotide, polypeptide or protein in a species. A wild-type form is distinguished from a mutant form of a polynucleotide, polypeptide or protein arising from genetic mutation(s).

In one embodiment, a first polypeptide that is an "analog" or "variant" or "derivative" of a second polypeptide is a polypeptide having at least about 50%, 60% or 70% sequence identity, but less than 100% sequence identity, with the second polypeptide. Such analogs, variants or derivatives may be comprised of non-naturally occurring amino acid residues, including without limitation, homoarginine, ornithine, penicillamine, and norvaline, as well as naturally occurring amino acid residues. Such analogs, variants or derivatives may also be composed of one or a plurality of D-amino acid residues, and may also contain peptidomimetics or peptide bond isosteres such as non-peptide linkages between two or more amino acid or peptidomimetic residues. In another embodiment, a first polypeptide is an "analog", "variant" or "derivative" of a second polypeptide if the first polypeptide is not a known cleavage product of the second polypeptide or is not a known precursor of the second polypeptide, even if the first polypeptide has 100% sequence identity to the second polypeptide or has a wild-type sequence.

In an embodiment, the term "derived from" as used herein refers to a polypeptide or peptide sequence that is based on a wild type or naturally occurring polypeptide or peptide sequence and can have one or more deletions, additions, and/or substitutions with natural amino acids, unnatural amino acids or peptidomimetics. In one embodiment, the derivative sequence shares at least about 40%, 50%, 60% or 70%, but less than 100%, sequence identity to the wild-type or naturally occurring sequence. In another embodiment, the derivative may be a fragment of a polypeptide, wherein the fragment is substantially identical (e.g., at least about 70%, 75%, 80%, 85%, 90%, or 95% identical) to the wild-type polypeptide over a length of at least about 5, 10, 15, 20, 25, 30, 35, or 40 amino acids. In still another embodiment, a polypeptide is "derived from" a wild-type polypeptide if it has a moiety (e.g., a polymer such as, e.g., PEG) directly or indirectly attached to it which is not present on the wild-type polypeptide, even if both polypeptides share 100% identity in their amino acid sequence.

The natriuretic peptide precursor C (NPPC) polypeptide is a single chain 126-amino acid pre-pro polypeptide, and which upon processing ultimately results in wild type CNP-22 (wtCNP-22). Removal of the signal peptide from NPPC yields pro-CNP, and further cleavage by the endoprotease furin generates an active 53-amino acid peptide (CNP-53), which is secreted and cleaved again to produce the mature 22-amino acid peptide (CNP, or CNP-22). In one embodiment, a "CNP variant" is at least about 40%, 50%, 60%, 70%, 75%, 80%, 85%, 90%, or 95% identical to the wild type NPPC over the same number of amino acid residues.

The term "effective amount" means a dosage sufficient to produce a desired result on a health condition, pathology, or disease of a subject or for a diagnostic purpose. The desired result may comprise a subjective or objective improvement in the recipient of the dosage. "Therapeutically effective amount" refers to that amount of an agent effective to produce the intended beneficial effect on health. It will be understood that the specific dose level and frequency of dosage for any particular patient may be varied and will depend upon a variety of factors, including the activity of the specific compound employed; the bioavailability, metabolic stability, rate of excretion and length of action of that compound; the mode and time of administration of the compound; the age, body weight, general health, sex, and diet of the patient; and the severity of the particular condition.

"Treatment" refers to prophylactic treatment or therapeutic treatment or diagnostic treatment. In certain embodiments, "treatment" refers to administration of a compound or composition to a subject for therapeutic, prophylactic or diagnostic purposes.

A "prophylactic" treatment is a treatment administered to a subject who does not exhibit signs of a disease or exhibits only early signs of the disease, for the purpose of decreasing the risk of developing pathology. The compounds or compositions of the disclosure may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional or physical, subjective or objective. The compounds of the disclosure may also be given as a therapeutic treatment or for diagnosis.

"Diagnostic" means identifying the presence, extent and/or nature of a pathologic condition. Diagnostic methods differ in their specificity and selectivity. While a particular diagnostic method may not provide a definitive diagnosis of a condition, it suffices if the method provides a positive indication that aids in diagnosis. A diagnostic treatment is administering a compound of the disclosure to aid in diagnosing a subject.

"Cartilage-associated biomarker" or "cartilage-associated marker" refers to a growth factor, enzyme, protein, nucleic acid, or other detectable biological substance or moiety whose level is increased or decreased in association with, e.g., cartilage turnover, cartilage formation, and/or cartilage growth. Such biomarkers may be measured before, during and/or after administration of a CNP variant as described herein. Exemplary cartilage-associated biomarkers include, but are not limited to, CNP, cGMP, propeptides of collagen type II and fragments thereof, collagen type II and fragments thereof, propeptides of collagen type I and fragments thereof, collagen type I and fragments thereof, proliferating cell nuclear antigen (PCNA), aggrecan chondroitin sulfate, syndecan-3 and annexin VI. Cartilage-associated biomarkers can be measured in any appropriate biological sample, including but not limited to tissues, blood, serum, plasma, cerebrospinal fluid, synovial fluid and urine. In some embodiments, the biomarkers are measured in blood, plasma or serum from animals undergoing efficacy/pharmacodynamic in vivo studies and/or from the conditioned media of ex vivo studies.

In certain embodiments, the level of at least one cartilage-associated biomarker is measured and the amount or frequency of administration of CNP variant administered to a subject can be adjusted according to the level of the biomarker measured. In some embodiments, the level of biomarker is "below a target level" or "above a target level." A target level of a biomarker is a level or range of levels of the biomarker at which a therapeutic effect is observed in the subject receiving the CNP variant. In certain embodiments, the target level of a biomarker for a subject having osteoarthritis is the level or range of levels of the biomarker observed in a normal, non-affected subject. In various embodiments, to indicate a therapeutic effect, the target level of a biomarker need not be equivalent to the level or range of levels of the biomarker observed in a normal subject, but can be within, e.g., 100%, 90%, 80%, 70%, 60%, 50%, 40%, 30%, 20%, 10% or 5% of the "normal" level or range of levels of the biomarker observed in a non-affected subject.

For example, if the level of a biomarker increases in association with cartilage formation or growth, the target level of the biomarker indicating a therapeutic effect may be higher than the level of the biomarker in patients suffering from osteoarthritis who have not been administered a CNP variant, and may optionally be lower than the "normal" level(s), at about the "normal" level(s), or above the "normal" level(s) of the biomarker in subjects not suffering from that disorder. In one embodiment, if the level of a biomarker is below a target level, it indicates an inadequate therapeutic effect, which may require an increase in the amount or frequency of administration of CNP variant administered. In a related embodiment, if the biomarker is above a target level, it indicates that more CNP variant than necessary has been administered, which may require a decrease in the amount or frequency of administration of the CNP variant administered.

As another example, if the level of a biomarker decreases in association with cartilage formation or growth, the target level of the biomarker indicating a therapeutic effect may be lower than the level of the biomarker in patients suffering from osteoarthritis who have not been administered a CNP variant, and may optionally be higher than the "normal" level(s), at about the "normal" level(s), or below the "normal" level(s) of the biomarker in subjects not suffering from that disorder. In such a case, the converse of the above adjustments in CNP variant amount and frequency of administration may apply.

"Pharmaceutical composition" refers to a composition suitable for pharmaceutical use in subject animal, including humans and mammals. A pharmaceutical composition comprises a therapeutically effective amount of a CNP variant, optionally another biologically active agent, and optionally a pharmaceutically acceptable excipient, carrier or diluent. In an embodiment, a pharmaceutical composition encompasses a composition comprising the active ingredient(s), and the inert ingredient(s) that make up the carrier, as well as any product that results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the disclosure and a pharmaceutically acceptable excipient, carrier or diluent.

"Pharmaceutically acceptable carrier" refers to any of the standard pharmaceutical carriers, buffers, and the like, such as a phosphate buffered saline solution, 5% aqueous solution of dextrose, and emulsions (e.g., an oil/water or water/oil emulsion). Non-limiting examples of excipients include adjuvants, binders, fillers, diluents, disintegrants, emulsifying agents, wetting agents, lubricants, glidants, sweetening agents, flavoring agents, and coloring agents. Suitable pharmaceutical carriers, excipients and diluents are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration).

A "pharmaceutically acceptable salt" is a salt that can be formulated into a compound for pharmaceutical use, including but not limited to metal salts (e.g., sodium, potassium, magnesium, calcium, etc.) and salts of ammonia or organic amines.

By "pharmaceutically acceptable" or "pharmacologically acceptable" is meant a material that is not biologically or otherwise undesirable, i.e., the material may be administered to an individual without causing any undesirable biological effects or without interacting in a deleterious manner with any of the components of the composition in which it is contained or with any components present on or in the body of the individual.

The term "unit dosage form" refers to physically discrete units suitable as unitary dosages for human and animal subjects, each unit containing a predetermined quantity of a compound of the disclosure calculated in an amount sufficient to produce the desired effect, optionally in association with a pharmaceutically acceptable excipient, diluent, carrier or vehicle. The specifications for the novel unit dosage forms of the present disclosure depend on the particular compound employed and the effect to be achieved, and the pharmacodynamics associated with each compound in the host.

"Physiological conditions" refer to conditions in the body of an animal (e.g., a human). Physiological conditions include, but are not limited to, body temperature and an aqueous environment of physiologic ionic strength, pH and enzymes.

As used herein, the term "subject" encompasses humans and non-human mammals and non-mammals to the extent that the compositions disclosed herein are useful when administered to such non-human species. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, vertebrates such as birds and fish. The term does not denote a particular age or gender.

The terms "polyethylene glycol," "PEG," "polyethylene oxide," and "PEO" are used interchangeably herein unless indicated otherwise. A CNP variant conjugated via an amino group to a "PEOn" polymer associated with the number n, in general has the formula: $CH_3-[-O-CH_2CH_2-]_n-C(=O)-NHR$, where n is the number of ethylene oxide units and R denotes the rest of the peptide. The "PEOn" polymer can optionally have an alkylene group, $(CH_2)_m$, where m is an integer from 1 to 5, between the carbonyl carbon and the repeating ethylene oxide units. Such a "PEOn" (e.g., PEO12 or PEO24) polymer is monodispersed, i.e., is a single discrete polymer of a particular molecular weight. Similarly, a CNP variant conjugated via an amino group to a "PEGnK" polymer associated with the number nK, in general has the formula: $CH_3-[-O-CH_2CH_2-]_p-C(=O)-NHR$, where p is an integer greater than 1. The "PEGnK" polymer also can optionally have an alkylene group, $(CH_2)_m$, where m is an integer from 1 to 5, between the carbonyl carbon and the repeating ethylene oxide units. However, such a "PEGnK" (e.g., PEG1K, PEG2K, PEG5K or PEG20K) polymer is polydispersed, i.e., contains a mixture of polymers having a distribution of molecular weights, where the number nK denotes the polymer number-average molecular weight ($M_n$) in kilo Daltons. For example, "PEG2K" conjugated to a CNP variant denotes a polydispersed PEG polymer having a polymer number-average molecular weight of around 2 kDa.

When a range of the mass of a polymer (e.g., PEG) is given (e.g., in units of kDa), the range refers to a range of polymer number-average molecular weights, not to a range of molecular weights of multiple polymers in a polydispersed mixture, unless expressly indicated otherwise.

The term "halogen," "halide," or "halo" refers to fluorine, chlorine, bromine, and/or iodine.

The term "alkyl" refers to a linear or branched saturated monovalent hydrocarbon radical, wherein the alkyl may optionally be substituted with one or more substituents Q as described herein. In certain embodiments, the alkyl is a linear saturated monovalent hydrocarbon radical that has 1 to 20 ($C_{1-20}$), 1 to 15 ($C_{1-15}$), 1 to 12 ($C_{1-12}$), 1 to 10 ($C_{1-10}$), or 1 to 6 ($C_{1-6}$) carbon atoms, or a branched saturated monovalent hydrocarbon radical of 3 to 20 ($C_{3-20}$), 3 to 15 ($C_{3-15}$), 3 to 12 ($C_{3-12}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms, including n-propyl and isopropyl), butyl (including all isomeric forms, including n-butyl, isobutyl, sec-butyl and tert-butyl), pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkoxy" refers to an —O-alkyl group. In certain embodiments, an alkoxy group may optionally be substituted with one or more substituents Q as described herein.

The term "haloalkyl" refers to an alkyl group that is substituted with one or more halide atoms. In certain embodiments, a haloalkyl group is substituted with one, two, three, four, five or six halide atoms. In certain embodiments, a haloalkyl group may optionally be substituted with one or more additional substituents Q as described herein.

The term "cycloalkyl" refers to a cyclic saturated bridged and/or non-bridged monovalent hydrocarbon radical, which may be optionally substituted with one or more substituents Q as described herein. In certain embodiments, the cycloalkyl has from 3 to 20 ($C_{3-20}$), from 3 to 15 ($C_{3-15}$), from 3 to 12 ($C_{3-12}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, decalinyl, and adamantyl.

The term "heterocyclyl" or "heterocyclic" refers to a monocyclic non-aromatic ring system or a multicyclic ring system that contains at least one non-aromatic ring, wherein one or more of the non-aromatic ring atoms are heteroatoms independently selected from 0, S, or N, and the remaining non-aromatic ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of heterocyclic groups include, but are not limited to, acridinyl, azepinyl, benzimidazolyl, benzindolyl, benzoisoxazolyl, benzisoxazinyl, benzodioxanyl, benzodioxolyl, benzofuranonyl, benzofuranyl, benzonaphthofuranyl, benzopyranonyl, benzopyranyl, benzotetrahydrofuranyl, benzotetrahydrothienyl, benzothiadiazolyl, benzothiazolyl, benzothiophenyl, benzotriazolyl, benzothiopyranyl, benzoxazinyl, benzoxazolyl, benzothiazolyl, β-carbolinyl, carbazolyl, chromanyl, chromonyl, cinnolinyl, coumarinyl, decahydroisoquinolinyl, dibenzofuranyl, dihydrobenzisothiazinyl, dihydrobenzisoxazinyl, dihydrofuryl, dihydropyranyl, dioxolanyl, dihydropyrazinyl, dihydropyridinyl, dihydropyrazolyl, dihydropyrimidinyl, dihydropyrrolyl, dioxolanyl, 1,4-dithianyl, furanonyl, furanyl, imidazolidinyl, imidazolinyl, imidazolyl, imidazopyridinyl, imidazothiazolyl, indazolyl, indolinyl, indolizinyl, indolyl, isobenzotetrahydrofuranyl, isobenzotetrahydrothienyl, isobenzothienyl, isochromanyl, isocoumarinyl, isoindolinyl, isoindolyl, isoquinolinyl, isothiazolidinyl, isothiazolyl, isoxazolidinyl, isoxazolyl, morpholinyl, naphthyridinyl, octahydroindolyl, octahydroisoindolyl, oxadiazolyl, oxazolidinonyl, oxazolidinyl, oxazolopyridinyl, oxazolyl, oxiranyl, perimidinyl, phenanthridinyl, phenathrolinyl, phenarsazinyl, phenazinyl, phenothiazinyl, phenoxazinyl, phthalazinyl, piperazinyl, piperidinyl, 4-piperidonyl, pteridinyl, purinyl, pyrazinyl, pyrazolidinyl, pyrazolyl, pyridazinyl, pyridinyl, pyridopyridinyl, pyrimidinyl, pyrrolidinyl, pyrrolinyl, pyrrolyl, quinazolinyl, quinolinyl, quinoxalinyl, quinuclidinyl, tetrahydrofuryl, tetrahydrofuranyl, tetrahydroisoquinolinyl, tetrahydropyranyl, tetrahydrothienyl, tetrazolyl, thiadiazolopyrimidinyl, thiadiazolyl, thiamorpholinyl, thiazolidinyl, thiazolyl, thienyl, triazinyl, triazolyl, and 1,3,5-trithianyl. In certain embodiments, a heterocyclic group may optionally be substituted with one or more substituents Q as described herein.

The term "aryl" refers to a monocyclic aromatic group or a multicyclic monovalent aromatic group that contain at least one aromatic hydrocarbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where at least one of the rings is aromatic and the others may be saturated, partially unsaturated, or aromatic, for example, dihydronaphthyl, indenyl, indanyl, and tetrahydronaphthyl (tetralinyl). In certain embodiments, an aryl group may optionally be substituted with one or more substituents Q as described herein.

The term "heteroaryl" refers to a monocyclic aromatic group or a multicyclic aromatic group that contain at least one aromatic ring, wherein at least one aromatic ring contains one or more heteroatoms independently selected from O, S, and N. Each ring of a heteroaryl group can contain one or two O atoms, one or two S atoms, and/or one to four N atoms, provided that the total number of heteroatoms in each ring is four or less and each ring contains at least one carbon atom. The heteroaryl may be attached to the main structure at any heteroatom or carbon atom which results in the creation of a stable compound. In certain embodiments, the heteroaryl has from 5 to 20, from 5 to 15, or from 5 to 10 ring atoms. Examples of monocyclic heteroaryl groups include, but are not limited to, pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, and triazinyl. Examples of bicyclic heteroaryl groups include, but are not limited to, indolyl, benzothiazolyl, benzoxazolyl, benzothienyl, quinolinyl, tetrahydroisoquinolinyl, isoquinolinyl, benzimidazolyl, benzopyranyl, indolizinyl, benzofuranyl, isobenzofuranyl, chromonyl, coumarinyl, cinnolinyl, quinoxalinyl, indazolyl, purinyl, pyrrolopyridinyl, furopyridinyl, thienopyridinyl, dihydroisoindolyl, and tetrahydroquinolinyl. Examples of tricyclic heteroaryl groups include, but are not limited to, carbazolyl, benzindolyl, phenanthrollinyl, acridinyl, phenanthridinyl, and xanthenyl. In certain embodiments, a heteroaryl group may optionally be substituted with one or more substituents Q as described herein.

The term "optionally substituted" is intended to mean that a group, including alkyl, alkoxy, haloalkyl, cycloalkyl, heterocyclyl, aryl and heteroaryl, may be substituted with one or more substituents Q (in one embodiment, one, two, three or four substituents Q), where each Q is independently selected from the group consisting of cyano, halo, oxo, nitro, $C_{1-6}$ alkyl, $C_{1-6}$ alkoxy, halo-$C_{1-6}$ alkyl, $C_{3-7}$ cycloalkyl, heterocyclyl, $C_{6-14}$ aryl, heteroaryl, —C(O)$R^e$, —C(O)O$R^e$, —C(O)N$R^f R^g$, —C(N$R^e$)N$R^f R^g$, —O$R^e$, —OC(O)$R^e$, —OC(O)O$R^e$, —OC(O)N$R^f R^g$, —OC(=N$R^e$)N$R^f R^g$, —OS(O)$R^e$, —OS(O)$_2 R^e$, —OS(O)N$R^f R^g$, —OS(O)$_2$N$R^f R^g$, —N$R^f R^g$, —N$R^e$C(O)$R^f$, —N$R^e$C(O)O$R^f$, —N$R^e$C(O)N$R^f R^g$, —N$R^e$C(=N$R^h$)N$R^f R^g$, —NR'S(O)$R^f$, —N$R^e$S(O)$_2 R^f$, —N$R^e$S(O)N$R^f R^g$, —N$R_e$S(O)$_2$N$R^f R^g$, —S$R^e$, —S(O)$_2 R^e$, —S(O)$_2 R^e$, and —S(O)$_2$N$R^f R^g$, wherein each $R^e$, $R^f$, $R^g$, and $R^h$ is independently hydrogen, $C_{1-6}$ alkyl, $C_{3-7}$ cycloalkyl, heterocyclyl, $C_{6-14}$ aryl, or heteroaryl; or $R^f$ and $R^g$, together with the N atom to which they are attached, form heterocyclyl.

B. CNP VARIANTS

The use of CNP22 as a therapeutic is limited by its short half-life in plasma (J. Clin. Endocrinol. Metab., 78: 1428-35 (1994)). In human plasma, the concentration of CNP22 typically is less than five picomolar. CNP22 is degraded and cleared from circulation by NEP and NPR-C in humans (Growth Hormone & IGF Res., 16: S6-S14). In all human and animal studies using systemically administered CNP22, continuous infusion has been used to increase the CNP22 concentration in the subjects. A CNP peptide having a longer half-life and at least a similar level of functionality would be beneficial to a CNP-based therapeutic strategy. CNP variants are also disclosed in related issued patents: U.S. Pat. Nos. 8,377,884; 8,198,242; and 8,598,121. Each of the recited patents are specifically incorporated herein by reference in their entirety.

The present disclosure provides CNP variants which have reduced affinity to NEP and/or NPR-C, and reduced susceptibility to cleavage by NEP and/or clearance by NPR-C, but which have substantially similar or better functionality than wild-type CNP22. Reduced susceptibility of CNP variants to cleavage by NEP and/or clearance by NPR-C would increase the plasma or serum half-life of the variants, thereby increasing the opportunity for the variants to distribute to the target tissues and sites and effectuate the desired pharmacological effects. In certain embodiments, the CNP variants described herein have reduced susceptibility to cleavage by NEP and/or clearance by NPR-C in vitro or in vivo by at least about 1.5-fold, 2-fold, 2.5-fold, 3-fold, 3.5-fold, 4-fold, 4.5-fold, or 5-fold compared to wtCNP22, and have increased plasma or serum half-life in vivo by at least about 1.5-fold, 2-fold, 2.5-fold, 3-fold, 3.5-fold, 4-fold, 4.5-fold, or 5-fold compared to wtCNP22, while retaining at least about 50%, 60%, 70%, 80%, 90% or 100% of the functionality of wtCNP22, or having at least about 1.5-fold, 2-fold, 2.5-fold, 3-fold, 3.5-fold, 4-fold, 4.5-fold, or 5-fold greater functionality than wtCNP22. CNP functionality can be evaluated in terms of, e.g., the level of one or more biomarkers (e.g., cGMP) associated with cartilage formation or growth in an in vitro or in vivo study, the prevention of osteoarthritic cartilage lose in an ex vivo or in vivo study, etc.

Natural substrates of NEP are small and natriuretic peptides (about 2.2 to about 3.2 kDa) are the largest of the natural substrates. According to X-ray crystallographic analyses, the NEP active-site is buried deep inside a central cavity, effectively restricting the size of substrate molecules to no more than about 3 kDa (Oefner et al., J. Mol. Biol., 296: 341-349 (2000)). Based on NPR-B signaling studies, variants of CNP-22, such as CNP-17 (retaining only the cyclic domain, Cys6-Cys22, of CNP22) and CNP-53 (CNP-22 with a 31-amino acid extension at the N-terminus), can still bind and activate NPR-B similarly to the 2.2 kDa wtCNP-22. Accordingly, the disclosure encompasses CNP variants conjugated to a natural (e.g., peptide) and/or synthetic (e.g., PEG) polymer at the N-terminus and/or C-terminus of CNP22 or variants thereof, which exhibit increased NEP resistance but retain the ability to bind and activate the NPR-B signaling receptor.

In one embodiment, the disclosure encompasses CNP variants represented by the general formula:

```
                                          SEQ ID NO: 129)
(x)-Cys6-Phe7-Gly8-Leu9-Lys10-Leu11-Asp12-Arg13-

Ile14-Gly15-Ser16-Met17-Ser18-Gly19-Leu20-Gly21-

Cys22-(z),
or
                                          SEQ ID NO: 130)
(x)-Gly1-Leu2-Ser3-Lys4-Gly5-Cys6-Phe7-Gly8-Leu9-

Lys10-Leu11-Asp12-Arg13-Ile14-Gly15-Ser16-Met17-

Ser18-Gly19-Leu20-Gly21-Cys22-(z),
``` wherein:
(x) and (z) each independently are a natural polymer (e.g., a peptide sequence containing at least one amino acid) and/or a synthetic polymer (e.g., PEG) as described herein, such that the total mass of the CNP variant is characterized by the ranges described generally herein, e.g., in the range from about 2.6 kDa or 2.8 kDa to about 6 or 7 kDa. In one embodiment, the residues from Cys6 to Cys22 form a cyclic portion. In an embodiment, (x) and/or (z) comprise an amino acid extension derived from NPPC or a non-CNP polypeptide (e.g., ANP, BNP, IgG, etc.), wherein the extension contains 1 to 40, 1 to 35, 1 to 31, 5 to 35, 5 to 31 or 5 to 15 amino acids. In another embodiment, the CNP variants comprise one or more modifications and/or substitutions with another natural amino acid, an unnatural amino acid, a peptidomimetic and/or a peptide bond isostere at one or more of the following positions of CNP22: Gly1, Lys4, Gly5, Cys6, Phe7, Gly8, Leu9, Lys10, Leu11, Ile14, Gly15, Ser16, Met17, Gly19, Leu20, and Gly21.

In another embodiment, CNP variants having a total mass characterized by the ranges described generally herein, e.g., from about 2.6 kDa or 2.8 kDa to about 6 or 7 kDa, designed for increased resistance to NEP degradation, are represented by the general formula:

```
                                          (SEQ ID NO: 131)
(x)-Cys6-Phe7-Gly8-Leu9-Lys10-Leu11-Asp12-Arg13-

Ile14-Gly15-Ser16-Met17-Ser18-Gly19-Leu20-Gly21-

Cys22-(z),
or
                                          (SEQ ID NO: 132)
(x)-Gly1-Leu2-Ser3-(b)4-Gly5-Cys6-Phe7-Gly8-Leu9-

(h)10-Leu11-Asp12-Arg13-Ile14-Gly15-Ser16-Met17-

Ser18-Gly19-Leu20-Gly21-Cys22-(z),
``` wherein:

(x) is a synthetic or natural polymeric group, or a combination thereof, wherein a non-limiting example of a synthetic polymeric group is PEG (or PEO), and a non-limiting example of a natural polymeric group is an amino acid sequence containing from 1 to 35 amino acids and derived from NPPC or variants thereof with substitutions and/or deletions, ANP, BNP, or other non-CNP (poly)peptides such as, e.g., serum albumin, IgG, histidine-rich glycoproteins, fibronectin, fibrinogen, zinc finger-containing polypeptides, osteocrin or fibroblast growth factor 2 (FGF2);

(z) may be absent or may be a synthetic or natural polymeric group, or a combination thereof, wherein a non-limiting example of a synthetic polymeric group is PEG, and a non-limiting example of a natural polymeric group is an amino acid sequence derived from a natriuretic polypeptide (e.g., NPPC, CNP, ANP or BNP) or non-natriuretic polypeptide (e.g., serum albumin or IgG); and (b) and (h) independently may be the wild type Lys at that position or may be replaced with a conservative amino acid substitution or any natural or unnatural amino acid or peptidomimetic that does not have a reactive primary amine on a side chain, including but not limited to Arg, Gly, 6-hydroxy-norleucine, citrulline (Cit), Gln, Glu, or Ser. In one embodiment, (b) is Arg. In another embodiment, for improved NEP resistance, (b) is not Gly.

In yet another embodiment, (h) is not Arg.

Non-limiting examples of amino acid sequences derived from NPPC or variants thereof include:

Arg,

Glu-Arg;

```
                                          (SEQ ID NO: 133)
Gly-Ala-Asn-Lys-Lys;

(SEQ ID NO: 134)
Gly-Ala-Asn-Arg-Arg;

(SEQ ID NO: 135)
Gly-Ala-Asn-Pro-Arg;

(SEQ ID NO: 136)
Gly-Ala-Asn-Gln-Gln;

(SEQ ID NO: 137)
Gly-Ala-Asn-Ser-Ser;

(SEQ ID NO: 138)
Gly-Ala-Asn-Arg-Gln;

(SEQ ID NO: 139)
Gly-Ala-Asn-Arg-Met;

(SEQ ID NO: 140)
Gly-Ala-Asn-Arg-Thr;

(SEQ ID NO: 141)
Gly-Ala-Asn-Arg-Ser;
```

-continued

```
                                        (SEQ ID NO: 142)
Ala-Ala-Trp-Ala-Arg-Leu-Leu-Gln-Glu-His-Pro-Asn-

Ala;

(SEQ ID NO: 143)
Ala-Ala-Trp-Ala-Arg-Leu-Leu-Gln-Glu-His-Pro-Asn-

Ala-Arg;

(SEQ ID NO: 144)
Asp-Leu-Arg-Val-Asp-Thr-Lys-Ser-Arg-Ala-Ala-Trp-

Ala-Arg;

(SEQ ID NO: 145)
Gln-Glu-His-Pro-Asn-Ala-Arg-Lys-Tyr-Lys-Gly-Ala-

Asn-Lys-Lys;

(SEQ ID NO: 146)
Gln-Glu-His-Pro-Asn-Ala-Arg-Lys-Tyr-Lys-Gly-Ala-

Asn-Arg-Arg;

(SEQ ID NO: 147)
Asp-Leu-Arg-Val-Asp-Thr-Lys-Ser-Arg-Ala-Ala-Trp-

Ala-Arg-Leu-Leu-Gln-Glu-His-Pro-Asn-Ala-Arg-Lys-

Tyr-Lys-Gly-Ala-Asn-Lys-Lys;
and (SEQ ID NO: 148)
Asp-Leu-Arg-Val-Asp-Thr-Lys-Ser-Arg-Ala-Ala-Trp- Ala-Arg-Leu-Leu-Gln-Glu-His-Pro-Asn-Ala-Arg-Lys- Tyr-Lys-Gly-Ala-Asn-Arg-Arg.
```

Non-limiting examples of amino acid sequences derived from non-CNP polypeptides such as, e.g., ANP, BNP, serum albumin and IgG include:

```
                                        (SEQ ID NO: 149)
Ser-Leu-Arg-Arg-Ser-Ser;

(SEQ ID NO: 150)
Asn-Ser-Phe-Arg-Tyr;

(SEQ ID NO: 151)
Ser-Pro-Lys-Met-Val-Gln-Gly-Ser-Gly;

(SEQ ID NO: 152)
Met-Val-Gln-Gly-Ser-Gly;

(SEQ ID NO: 153)
Lys-Val-Leu-Arg-Arg-Tyr;

(SEQ ID NO: 154)
Lys-Val-Leu-Arg-Arg-His;

(SEQ ID NO: 155)
Gly-Gln-His-Lys-Asp-Asp-Asn-Pro-Asn-Leu-Pro-Arg;

(SEQ ID NO: 156)
Gly-Val-Pro-Gln-Val-Ser-Thr-Ser-Thr;

(SEQ ID NO: 157)
Gly-Glu-Arg-Ala-Phe-Lys-Ala-Trp-Ala-Val-Ala-Arg-

Leu-Ser-Gln;
and (SEQ ID NO: 158)
Gly-Gln-Pro-Arg-Glu-Pro-Gln-Val-Tyr-Thr-Leu-Pro- Pro-Ser.
```

In an embodiment, the N-terminal (x) group and/or the C-terminal (z) group of any of the CNP variants having an (x) and/or (z) group, as described herein, independently comprise an amino acid sequence that contains a small number of, if any, acidic natural or unnatural amino acids (e.g., Asp or Glu). In another embodiment, (x) and/or (z) are enriched in basic natural or unnatural amino acids (e.g., Lys, Arg, or His) to maintain an alkaline pI similar to the pI of CNP22 (pI 8.9). In one embodiment, the pI of the CNP variants is in the range from about 8 to about 10.5, designed so that the CNP variants can diffuse more readily through the extracellular matrix surrounding chondrocytes of osteoarthritic joints. In narrower embodiments, the pI of the CNP variants is from about 8.5 to about 10.5, or from about 8.5 to about 10, or from about 9 to about 10.

In yet another embodiment, (x) and/or (z) are enriched in polar natural or unnatural amino acids, designed for increased aqueous solubility. In still another embodiment, (x) and/or (z) contain a small number of, if any, hydrophobic natural or unnatural amino acids (e.g., Ala, Val, Leu, Ile, or Met).

In a further embodiment, the N-terminus of the CNP variants terminates in at least one glycine residue, designed for increased serum half-life. In a related embodiment, to prevent pyroglutamine formation, the N-terminus of CNP variants terminates in a glycine residue if it would otherwise terminate in glutamine. In one embodiment, the (x) group contains an amino acid extension whose N-terminus terminates in at least one glycine residue. In another embodiment, (x) and/or (z) do not contain two adjacent basic natural or unnatural amino acids (e.g., Lys-Lys or Arg-Arg), designed to reduce susceptibility to cleavage by the protease furin. In an embodiment, (x) does not contain two adjacent basic amino acids immediately preceding the position corresponding to Gly1 of CNP22.

In still another embodiment, the (x) group and/or the (z) group of the CNP variants comprise an amino acid sequence derived from NPPC (e.g., derived from CNP53). In an embodiment, (x) comprises an amino acid sequence derived from the N-terminal tail of ANP or BNP. In another embodiment, (z) comprises an amino acid sequence derived from the C-terminal tail of ANP or BNP. In a further embodiment, (x) and/or (z) comprise an amino acid sequence derived from a non-natriuretic polypeptide such as, e.g., IgG, human serum albumin (HSA), histidine-rich glycoproteins, fibronectin, fibrinogen, zinc finger-containing polypeptides, FGF-2, and bone-targeting proteins (e.g., osteocrin, osteopontin, osteocalcin, and sialoprotein).

In any embodiment described herein in which CNP22 or a variant thereof can have an N-terminal (x) group and/or a C-terminal (z) group, (x) and/or (z) independently can contain an amino acid sequence derived from the functional domain of a bone morphogenetic protein (BMP). An N-terminal and/or C-terminal amino acid extension derived from the functional domain of a BMP can increase the NEP resistance, and hence the serum half-life of the CNP variant, by increasing the total mass of the CNP variant to characterized by the ranges described generally herein, e.g., a range from about 2.6 kDa or 2.8 kDa to about 6 or 7 kDa. In addition, since certain BMPs are growth factors and cytokines that induce the formation of bone and cartilage, a fragment derived from the functional domain of a BMP can promote chondrocyte, cartilage or bone growth by a mechanism distinct from activation of the guanylyl cyclase function of NPR-B by the cyclic domain of CNP22 or a variant thereof. Non-limiting examples of BMPs that promote bone formation and development, cartilage formation and development, and/or osteoblast differentiation include BMP1, BMP2, BMP3, BMP5, BMP7, and BMP8a. In an embodiment, the N-terminus and/or C-terminus of CNP22 or a variant thereof independently are conjugated to an amino acid sequence derived from the last 140 amino acids in the C-terminal portion of BMP1, BMP2, BMP3, BMP5, BMP7, or BMP8a.

In one embodiment, the CNP variants contain an amino acid extension at the N-terminus and/or C-terminus of CNP22 or CNP17, including but not limited to:

```
(CNP-53)
                                                (SEQ ID NO: 6)
DLRVDTKSRAAWARLLQEHPNARKYKGANKKGLSKGCFGLKLDRIGSM

SG LGC;

(CNP-37, Analog BL)
                                                (SEQ ID NO: 22)
QEHPNARKYKGANKKGLSKGCFGLKLDRIGSMSGLGC;

(Analog CA)
                                                (SEQ ID NO: 68)
AAWARLLQEHPNAGLSKGCFGLKLDRIGSMSGLGC;

(Analog CB)
                                                (SEQ ID NO: 69)
AAWARLLQEHPNARGLSKGCFGLKLDRIGSMSGLGC;

(Analog CC)
                                                (SEQ ID NO: 70)
DLRVDTKSRAAWARGLSKGCFGLKLDRIGSMSGLGC;

(SEQ ID NO: 71)
RGLSKGCFGLKLDRIGSMSGLGC;

(SEQ ID NO: 72)
ERGLSKGCFGLKLDRIGSMSGLGC;

(SEQ ID NO: 73)
GANQQGLSKGCFGLKLDRIGSMSGLGC;

(SEQ ID NO: 74)
GANRRGLSKGCFGLKLDRIGSMSGLGC;

(SEQ ID NO: 75)
GANPRGLSKGCFGLKLDRIGSMSGLGC;

(SEQ ID NO: 76)
GANSSGLSKGCFGLKLDRIGSMSGLGC;

(SEQ ID NO: 48)
GHKSEVAHRFKGANKKGLSKGCFGLKLDRIGSMSGLGC;
and (Analog CD) (CNP17 having N-terminal and
C-terminal tails derived from BNP)
                                                (SEQ ID NO: 77)
SPKMVQGSG-CNP17-KVLRRH.
```

In another embodiment, the CNP variants have a K4R substitution at position 4 of CNP22. Non-limiting examples of CNP(K4R) variants include:

```
            (Analog AY)
                                                (SEQ ID NO: 52)
            GANRRGLSRGCFGLKLDRIGSMSGLGC;

(Analog CI)
                                                (SEQ ID NO: 78)
            GANPRGLSRGCFGLKLDRIGSMSGLGC;

(Analog AZ)
                                                (SEQ ID NO: 79)
            RGLSRGCFGLKLDRIGSMSGLGC;
```

```
-continued
(Analog BA)
                                                (SEQ ID NO: 80)
ERGLSRGCFGLKLDRIGSMSGLGC;

(Analog CH)
                                                (SEQ ID NO: 81)
GANQQGLSRGCFGLKLDRIGSMSGLGC;
and (Analog CG)
                                                (SEQ ID NO: 82)
GANSSGLSRGCFGLKLDRIGSMSGLGC.
```

In further embodiments, the CNP variants are chimeras comprising CNP22, or a variant thereof having amino acid addition(s), deletion(s), and/or substitution(s), and a peptide fragment derived from a polypeptide or protein other than CNP, or the whole non-CNP polypeptide or protein, to the N-terminus of the CNP peptide, wherein CNP22 or the variant thereof may optionally have an N-terminal amino acid extension of one or more amino acid residues. In certain embodiments, the CNP chimeras comprise CNP22 or a variant thereof that has an N-terminal amino acid extension of one or more amino acid residues. In certain embodiments, the CNP chimeras contain lysine-lysine (KK) residues or GANKK residues immediately preceding the first position of CNP22 (Gly in the case of CNP22) or a variant thereof. In other embodiments, the CNP chimeras contain one or two residues different from lysine-lysine immediately preceding the first position of CNP22 or a variant thereof. Non-limiting examples of residues that can immediately precede the first position of CNP22 or a variant thereof include KP, PK, PR, PQ, QK, QQ, RR, SS, GANKP (SEQ ID NO: 159), GANPK (SEQ ID NO: 160), GANPR (SEQ ID NO:135), GANPQ (SEQ ID NO: 161), GANQK (SEQ ID NO: 162), GANQQ (SEQ ID NO: 136), GANRR (SEQ ID NO: 134), and GANSS (SEQ ID NO: 137).

In another embodiment, the CNP variants are chimera comprising CNP22 and an N-terminal peptide fragment, including but not limited to:

```
(Analog CQ) (histidine-rich glycoprotein
(HRGP) fragment-CNP22 chimera)
                                                (SEQ ID NO: 83)
GHHSHEQHPHGANQQGLSKGCFGLKLDRIGSMSGLGC;

(Analog CR) (HRGP fragment-CNP22 chimera)
                                                (SEQ ID NO: 84)
GAHHPHEHDTHGANQQGLSKGCFGLKLDRIGSMSGLGC;

(Analog CX) (HRGP fragment-CNP22 chimera)
                                                (SEQ ID NO: 85)
GHHSHEQHPHGANPRGLSKGCFGLKLDRIGSMSGLGC;

(Analog CF) (IgG₁(Fc) fragment-CNP22 chimera)
                                                (SEQ ID NO: 86)
GQPREPQVYTLPPSGLSKGCFGLKLDRIGSMSGLGC;

(Analog CY) (human serum albumin (HSA)
fragment-CNP22 chimera)
                                                (SEQ ID NO: 87)
GQHKDDNPNLPRGANPRGLSKGCFGLKLDRIGSMSGLGC;

(Analog CE) (HSA fragment-CNP22 chimera)
                                                (SEQ ID NO: 88)
GERAFKAWAVARLSQGLSKGCFGLKLDRIGSMSGLGC;

(Analog CZ) (osteocrin "NPR C inhibitor"
fragment-CNP22 chimera)
                                                (SEQ ID NO: 89)
FGIPMDRIGRNPRGLSKGCFGLKLDRIGSMSGLGC;
and
```

```
(Analog DA) (FGF2 "heparin-binding domain"
fragment-CNP22 chimera)
                                    (SEQ ID NO: 90)
GKRTGQYKLGSKTGPGPKGLSKGCFGLKLDRIGSMSGLGC.
```

In yet another embodiment, the CNP variants are chimera comprising an N-terminal peptide fragment and CNP22 in which arginine is substituted for Lys4 of CNP22 ("CNP22 (K4R)"), including but not limited to:

```
(Analog CK) (IgG₁(Fc) fragment-CNP22(K4R)
chimera)
                                    (SEQ ID NO: 91)
GQPREPQVYTGANQQGLSRGCFGLKLDRIGSMSGLGC;

(Analog CL) (HSA fragment-CNP22(K4R) chimera)
                                    (SEQ ID NO: 92)
GVPQVSTSTGANQQGLSRGCFGLKLDRIGSMSGLGC;

(Analog CM) (fibronectin fragment-CNP22(K4R)
chimera)
                                    (SEQ ID NO: 93)
GQPSSSSQSTGANQQGLSRGCFGLKLDRIGSMSGLGC;

(Analog CN) (fibrinogen fragment-CNP22(K4R)
chimera)
                                    (SEQ ID NO: 94)
GQTHSSGTQSGANQQGLSRGCFGLKLDRIGSMSGLGC;

(Analog CO) (fibrinogen fragment-CNP22(K4R)
chimera)
                                    (SEQ ID NO: 95)
GSTGQWHSESGANQQGLSRGCFGLKLDRIGSMSGLGC;
and (Analog CP) (zinc finger fragment-CNP22(K4R)
chimera)
                                    (SEQ ID NO: 96)
GSSSSSSSSSGANQQGLSRGCFGLKLDRIGSMSGLGC.
```

Chimera comprising IgG and CNP22 or a variant thereof are designed for, inter alia, increased resistance to NEP degradation and reduced binding to serum albumin. CNP chimera comprising a surface fragment of HSA are designed for, inter alia, reduced immunogenicity and reduced binding to serum albumin. HRGP-CNP22 and HRGP-CNP22(K4R) chimera containing a cationic, histidine-rich, non-lysine, non-arginine sequence at the N-terminus are designed for, inter alia, increased stability to proteases. Chimera containing an osteocrin fragment are designed to release, upon protease (e.g., furin) cleavage, the osteocrin fragment at bone growth plates, where the fragment would inhibit the clearance receptor NPR-C. With respect to chimera comprising an FGF2 heparin-binding fragment, heparin binding to the fragment is designed to protect the chimera from degradation, thereby providing a longer serum half-life. Chimera containing a fibronectin, fibrinogen, or zinc-finger fragment are designed for reduced binding to serum albumin, among other features.

Not intending to be bound by theory, a CNP variant of molecular weight from about 2.6 or 2.8 kDa to about 6 or 7 kDa which has increased resistance to NEP degradation and has similar or improved functionality (e.g., binding to NPR-B and stimulation of cGMP signaling) as compared to wtCNP22, may be more effective if it does not bind tightly to plasma proteins such as serum albumin. A CNP variant that does not bind tightly to plasma proteins (e.g., serum albumin) may be more effective in diffusing through cartilage, getting to chondrocytes of osteoarthritic joints, and binding to and activating NPR-B for cGMP signaling. In one embodiment, CNP variants designed for reduced binding to plasma proteins (e.g., serum albumin) are chimeras comprising CNP22 or a variant thereof and a peptide fragment from IgG. In another embodiment, CNP variants designed for reduced binding to plasma proteins are chimeras comprising CNP22 or CNP22(K4R) and a fragment from a polypeptide (e.g., IgG, HSA, fibronectin, fibrinogen, a zinc finger-containing polypeptide, etc.). In yet another embodiment, CNP variants designed for reduced binding to plasma proteins comprise CNP22 or a variant thereof conjugated to a hydrophilic or water-soluble polymer. In one embodiment, the hydrophilic or water-soluble polymer is PEG (or PEO). In another embodiment, the hydrophilic or water-soluble polymer (e.g., PEG) is functionalized with one or more functional groups that impart a negative charge to the polymer under physiological conditions, such as, e.g., carboxyl, sulfate or phosphate groups, or a combination thereof.

In a further embodiment, CNP variants of the disclosure include truncated CNP peptides ranging from human CNP-17 (hCNP-17) to human CNP-53 (hCNP-53), and having wild-type amino acid sequences derived from hCNP-53. Such truncated CNP peptides include:

```
(CNP-53)
                                    (SEQ ID NO: 6)
DLRVDTKSRAAWARLLQEHPNARKYKGANKKGLSKGCFGLKLDRIGSMSGL
GC;

(CNP-52)
                                    (SEQ ID NO: 7)
LRVDTKSRAAWARLLQEHPNARKYKGANKKGLSKGCFGLKLDRIGSMSGL
GC;

(CNP-51)
                                    (SEQ ID NO: 8)
RVDTKSRAAWARLLQEHPNARKYKGANKKGLSKGCFGLKLDRIGSMSGLG
C;

(CNP-50)
                                    (SEQ ID NO: 9)
VDTKSRAAWARLLQEHPNARKYKGANKKGLSKGCFGLKLDRIGSMSGLGC;

(CNP-49)
                                    (SEQ ID NO: 10)
DTKSRAAWARLLQEHPNARKYKGANKKGLSKGCFGLKLDRIGSMSGLGC;

(CNP-48)
                                    (SEQ ID NO: 11)
TKSRAAWARLLQEHPNARKYKGANKKGLSKGCFGLKLDRIGSMSGLGC;

(CNP-47)
                                    (SEQ ID NO: 12)
KSRAAWARLLQEHPNARKYKGANKKGLSKGCFGLKLDRIGSMSGLGC;

(CNP-46)
                                    (SEQ ID NO: 13)
SRAAWARLLQEHPNARKYKGANKKGLSKGCFGLKLDRIGSMSGLGC;

(CNP-45)
                                    (SEQ ID NO: 14)
RAAWARLLQEHPNARKYKGANKKGLSKGCFGLKLDRIGSMSGLGC;

(CNP-44)
                                    (SEQ ID NO: 15)
AAWARLLQEHPNARKYKGANKKGLSKGCFGLKLDRIGSMSGLGC;

(CNP-43)
                                    (SEQ ID NO: 16)
AWARLLQEHPNARKYKGANKKGLSKGCFGLKLDRIGSMSGLGC;

(CNP-42)
                                    (SEQ ID NO: 17)
WARLLQEHPNARKYKGANKKGLSKGCFGLKLDRIGSMSGLGC;
```

(CNP-41)
ARLLQEHPNARKYKGANKKGLSKGCFGLKLDRIGSMSGLGC; (SEQ ID NO: 18)

(CNP-40)
RLLQEHPNARKYKGANKKGLSKGCFGLKLDRIGSMSGLGC; (SEQ ID NO: 19)

(CNP-39)
LLQEHPNARKYKGANKKGLSKGCFGLKLDRIGSMSGLGC; (SEQ ID NO: 20)

(CNP-38)
LQEHPNARKYKGANKKGLSKGCFGLKLDRIGSMSGLGC; (SEQ ID NO: 21)

(CNP-37)
QEHPNARKYKGANKKGLSKGCFGLKLDRIGSMSGLGC; (SEQ ID NO: 22)

(CNP-36)
EHPNARKYKGANKKGLSKGCFGLKLDRIGSMSGLGC; (SEQ ID NO: 23)

(CNP-35)
HPNARKYKGANKKGLSKGCFGLKLDRIGSMSGLGC; (SEQ ID NO: 24)

(CNP-34)
PNARKYKGANKKGLSKGCFGLKLDRIGSMSGLGC; (SEQ ID NO: 25)

(CNP-33)
NARKYKGANKKGLSKGCFGLKLDRIGSMSGLGC; (SEQ ID NO: 26)

(CNP-32)
ARKYKGANKKGLSKGCFGLKLDRIGSMSGLGC; (SEQ ID NO: 27)

(CNP-31)
RKYKGANKKGLSKGCFGLKLDRIGSMSGLGC; (SEQ ID NO: 28)

(CNP-30)
KYKGANKKGLSKGCFGLKLDRIGSMSGLGC; (SEQ ID NO: 29)

(CNP-29)
YKGANKKGLSKGCFGLKLDRIGSMSGLGC; (SEQ ID NO: 30)

(CNP-28)
KGANKKGLSKGCFGLKLDRIGSMSGLGC; (SEQ ID NO: 31)

(CNP-27)
GANKKGLSKGCFGLKLDRIGSMSGLGC; (SEQ ID NO: 32)

(CNP-26)
ANKKGLSKGCFGLKLDRIGSMSGLGC; (SEQ ID NO: 33)

(CNP-25)
NKKGLSKGCFGLKLDRIGSMSGLGC; (SEQ ID NO: 34)

(CNP-24)
KKGLSKGCFGLKLDRIGSMSGLGC; (SEQ ID NO: 35)

(CNP-23)
KGLSKGCFGLKLDRIGSMSGLGC; (SEQ ID NO: 36)

(CNP-22)
GLSKGCFGLKLDRIGSMSGLGC; (SEQ ID NO: 37)

(CNP-21)
LSKGCFGLKLDRIGSMSGLGC; (SEQ ID NO: 38)

(CNP-20)
SKGCFGLKLDRIGSMSGLGC; (SEQ ID NO: 39)

(CNP-19)
KGCFGLKLDRIGSMSGLGC; (SEQ ID NO: 40)

(CNP-18)
GCFGLKLDRIGSMSGLGC; (SEQ ID NO: 41)
and (CNP-17)
CFGLKLDRIGSMSGLGC. (SEQ ID NO: 42)

In certain embodiments, CNP variants do not include CNP-17, CNP-22 or CNP-53.

In another embodiment, the truncated CNP peptides ranging from hCNP-17 to hCNP-53 can contain amino acid addition(s), deletion(s), and/or substitution(s) with natural or unnatural amino acid(s) or peptidomimetic(s) (e.g., peptide bond isostere(s)), as described herein, at any one or more of the amino acid positions of the particular truncated CNP peptides. In yet another embodiment, the truncated CNP peptides having wild-type sequences or amino acid addition(s), deletion(s) and/or substitution(s), can be conjugated at the N-terminus, C-terminus and/or internal site(s) to any of the moieties described herein, including but not limited to synovium- or cartilage-targeting moieties (e.g., bisphosphonates, bone- or cartilage-targeting peptide sequences (e.g., polyAsp, polyGlu), peptide sequences derived from bone-targeting domains of bone proteins (e.g., osteopontin, osteocalcin, sialoprotein)), peptide sequences derived from the functional domains of bone morphogenetic proteins (e.g., BMP2, BMP3, BMP5, BMP7, BMP8a), peptide sequences derived from natriuretic polypeptides (e.g., NPPC, ANP, BNP), peptide sequences derived from polypeptides of non-natriuretic origin (e.g., serum albumin, IgG, histidine-rich glycoproteins, fibronectin, fibrinogen, zinc finger-containing polypeptides, FGF-2, osteocrin), moieties that reduce renal clearance (e.g., negatively charged PEG moieties), hydrophilic polymers (e.g., PEG), carbohydrates (e.g., carbohydrates recognized by receptors on the surface of cells within osteoarthritic joints), hydrophobic acids (e.g., $C_5$-$C_{12}$ carboxylic acids, natural fatty acids), phospholipids, and combinations thereof. In an embodiment, the truncated CNP peptides having wild-type sequences or amino acid addition(s), deletion(s) and/or substitution(s), and optionally conjugated to one or more moieties at the N-terminus, C-terminus and/or internal site(s), have a total mass characterized by the ranges described generally herein, e.g., from about 2.6 kDa or 2.8 kDa to about 6 or 7 kDa.

In a further embodiment, the CNP variants are derivatives of CNP37, which is QEHPNARKYKGANKK-CNP22 (SEQ ID NO: 22). The CNP37 variants can contain amino acid addition(s), deletion(s), and/or substitution(s) with natural or unnatural amino acid(s) or peptidomimetic(s) (e.g., peptide bond isostere(s)) at any one or more of the 37 positions of CNP37. Non-limiting examples of substitutions that can be made in CNP37, based on the numbering of CNP22, include K4R, G5S, G5R, G8S, K10R, G15S, S16Q, M17N, G19R, and combinations thereof. In an embodiment, the CNP37 derivatives contain a substitution of Met17 to a natural (e.g., asparagine) or unnatural amino acid or peptidomimetic, designed in part to avoid oxidation of the sulfur atom of methionine. In another embodiment, the CNP37 variants contain substitution(s) of Lys8, Lys10, Lys14 and/or Lys15 (based on numbering from the N-terminus of CNP37) to non-basic natural or unnatural amino acid(s) or peptiomimetic(s), designed in part to reduce albumin binding.

In addition or alternatively to amino acid addition(s), deletion(s), and/or substitution(s), the CNP37 derivatives can be conjugated at the N-terminus, C-terminus, and/or an internal site to any of the moieties described herein, including but not limited to bone- or cartilage-targeting moieties (e.g., bone-targeting peptide domains), moieties that reduce renal clearance (e.g., negatively charged PEG moieties), hydrophilic polymers (e.g., PEG), amino acid sequences comprising one or more amino acids (e.g., osteocrin "NPR-C inhibitor" fragment), carbohydrates (e.g., carbohydrates recognized by receptors on the surface of cells at bone growth plates), hydrophobic acids (e.g., $C_5$-$C_{12}$ carboxylic acids and natural fatty acids), and combinations thereof.

In one embodiment, the CNP variants are modified CNP37 peptides having mutation(s)/substitution(s) at the furin cleavage site (underlined), designed to improve in vivo resistance to the furin protease, and/or containing glycine (underlined) at the N-terminus, designed to improve plasma stability and prevent pyroglutamine formation. Such CNP37 variants include but are not limited to:

```
(An. CS)
                                           (SEQ ID NO: 97)
GQEHPNARKYKGANPKGLSKGCFGLKLDRIGSMSGLGC;

(An. CT)
                                           (SEQ ID NO: 98)
GQEHPNARKYKGANQKGLSKGCFGLKLDRIGSMSGLGC;

(An. CU)
                                           (SEQ ID NO: 99)
GQEHPNARKYKGANQQGLSKGCFGLKLDRIGSMSGLGC;

(An. CW)
                                          (SEQ ID NO: 100)
GQEHPNARKYKGANKPGLSKGCFGLKLDRIGSMSGLGC;

(Gly-CNP37, An. DB)
                                            (SEQ ID NO: 2)
GQEHPNARKYKGANKKGLSKGCFGLKLDRIGSMSGLGC;;
and (Pro-Gly-CNP37)
                                            (SEQ ID NO: 1)
PGQEHPNARKYKGANKKGLSKGCFGLKLDRIGSMSGLGC
```

In a further embodiment, the CNP variants of the disclosure include CNP peptides and variants thereof that can be produced by the fusion protein process described herein. Non-limiting examples of CNP variants that can be produced by the fusion protein process described herein, using chemical or proteolytic cleavage or protein self-cleavage, include:

```
(Gly-wtCNP53)
                                            (SEQ ID NO: 3)
GDLRVDTKSRAAWARLLQEHPNARKYKGANKKGLSKGCFGLKLDRIGSMSG
LGC;

(Gly-wtCNP37)
                                            (SEQ ID NO: 2)
GQEHPNARKYKGANKKGLSKGCFGLKLDRIGSMSGLGC;

(wtCNP37)
                                           (SEQ ID NO: 22)
QEHPNARKYKGANKKGLSKGCFGLKLDRIGSMSGLGC;

(HSA fragment-wtCNP27)
                                           (SEQ ID NO: 48)
GHKSEVAHRFKGANKKGLSKGCFGLKLDRIGSMSGLGC;

[CNP27(K4,5,9R)]
                                           (SEQ ID NO: 52)
GANRRGLSRGCFGLKLDRIGSMSGLGC;

[CNP53(M48N)]
                                            (SEQ ID NO: 6)
DLRVDTKSRAAWARLLQEHPNARKYKGANKKGLSKGCFGLKLDRIGSNSGL
GC;

[Gly-CNP37(M32N)]
                                           (SEQ IS NO: 46)
GQEHPNARKYKGANKKGLSKGCFGLKLDRIGSNSGLGC;

[CNP37(M32N)]
                                           (SEQ ID NO: 43)
QEHPNARKYKGANKKGLSKGCFGLKLDRIGSNSGLGC;

[HSA-CNP27(M22N)]
                                           (SEQ ID NO: 49)
GHKSEVAHRFK-GANKKGLSKGCFGLKLDRIGSNSGLGC;

[CNP27(K4,5,9R, M22N)]
                                           (SEQ ID NO: 53)
GANRRGLSRGCFGLKLDRIGSNSGLGC;

(Pro-wtCNP53)
                                            (SEQ ID NO: 4)
PDLRVDTKSRAAWARLLQEHPNARKYKGANKKGLSKGCFGLKLDRIGSMSG
LGC;

(Pro-Gly-wtCNP37)
                                            (SEQ ID NO: 1)
PGQEHPNARKYKGANKKGLSKGCFGLKLDRIGSMSGLGC;

(Pro-wtCNP37)
                                           (SEQ ID NO: 44)
PQEHPNARKYKGANKKGLSKGCFGLKLDRIGSMSGLGC;

(wtCNP34)
                                           (SEQ ID NO: 25)
PNARKYKGANKKGLSKGCFGLKLDRIGSMSGLGC;

(Pro-HSA-wtCNP27)
                                           (SEQ ID NO: 50)
P-GHKSEVAHRFK-GANKKGLSKGCFGLKLDRIGSMSGLGC;

[Pro-CNP27(K4,5,9R)]
                                           (SEQ ID NO: 54)
PGANRRGLSRGCFGLKLDRIGSMSGLGC;

(Met-wtCNP53)
                                            (SEQ ID NO: 5)
MDLRVDTKSRAAWARLLQEHPNARKYKGANKKGLSKGCFGLKLDRIGSMSG
LGC;

(Met-Gly-wtCNP37)
                                           (SEQ ID NO: 47)
MGQEHPNARKYKGANKKGLSKGCFGLKLDRIGSMSGLGC;

(Met-wtCNP37)
                                           (SEQ ID NO: 45)
MQEHPNARKYKGANKKGLSKGCFGLKLDRIGSMSGLGC;

(Met-HSA-wtCNP27)
                                           (SEQ ID NO: 51)
M-GHKSEVAHRFK-GANKKGLSKGCFGLKLDRIGSMSGLGC;
```

-continued

[Met-CNP27(K4,5,9R)]
(SEQ ID NO: 55)
MGANRRGLSRGCFGLKLDRIGSMSGLGC.

Other CNP variants, including truncated CNP peptides ranging from hCNP-17 to hCNP-53 and having wild-type sequences or amino acid addition(s), deletion(s), and/or substitution(s), can also be produced by the fusion protein process described herein, so long as the intended site of chemical or proteolytic cleavage of the fusion protein is not present within the amino acid sequence of the target CNP variant itself. As a non-limiting example, the fusion protein process described herein can be employed to produce truncated wtCNP34 using formic acid cleavage.

In additional embodiments, for any of the CNP peptides and CNP variants described herein that have asparagine (Asn/N) residue(s) and/or glutamine (Gln/Q) residue(s), whether they have a wild-type sequence or a non-natural amino acid sequence, any Asn residue(s) and/or any Gln residue(s) can independently be substituted with any other natural or unnatural amino acids, including conservative substitutions such as Asn to Gln. Such substitution(s) are designed in part to minimize or avoid any potential deamidation of asparagine and/or glutamine. Non-limiting examples of CNP peptides and variants in which any Asn residue(s) and/or any Gln residue(s) can independently be substituted with any other natural or unnatural amino acids, including conservative substitutions such as Asn to Gln, include wtCNP34, wtCNP37, Gly-wtCNP37, Pro-wtCNP37, Pro-Gly-wtCNP37, GHKSEVAHRFK-wtCNP27 (SEQ ID NO: 48), Pro-GHKSEVAHRFK-wtCNP27 (SEQ ID NO: 50), PEO12-GANRR-CNP22(K4R) (SEQ ID NO: 101), and PE024-GANRR-CNP22(K4R) (SEQ ID NO: 102). In certain embodiments, an asparagine residue of the CNP peptides and CNP variants described herein is not substituted with glutamine, aspartic acid or glutamic acid. In certain embodiments, a glutamine residue of the CNP peptides and CNP variants described herein is not substituted with asparagine, aspartic acid, or glutamic acid.

As a non-limiting example, asparagine residues 7 and/or 15 of Pro-Gly-wtCNP37 (PGQEHPNARKYKGANKKGL-SKGCFGLKLDRIGSMSGLGC) (SEQ ID NO: 1) can independently be substituted with any other natural or unnatural amino acids, including glutamine, to avoid any potential deamidation of the asparagine residue(s) to aspartic acid or isoaspartic acid. In certain embodiments, asparagine residues 7 and/or 15 of Pro-Gly-wtCNP37 are not substituted with glutamine, aspartic acid, or glutamic acid.

It is understood, however, that the present disclosure encompasses CNP variants in which any one or more, up to all, residues susceptible to deamidation or a deamidation-like reaction (e.g., isomerization) may be converted to other residue(s) via deamidation or a deamidation-like reaction to any extent, up to 100% conversion per converted residue. In certain embodiments, the disclosure encompasses CNP variants in which: (1) any one or more, up to all, asparagine (Asn/N) residues may be converted to aspartic acid or aspartate, and/or to isoaspartic acid or isoaspartate, via deamidation up to about 5%, 10%, 20%, 30%, 40%, 50%, 60%, 70%, 80%, 90% or 100% conversion per converted residue; (2) any one or more, up to all, glutamine (Gln/Q) residues may be converted to glutamic acid or glutamate, and/or to isoglutamic acid or isoglutamate, via deamidation up to about 5%, 10%, 20%, 30%, 40%, 50%, 60%, 70%, 80%, 90% or 100% conversion per converted residue; (3) any one or more, up to all, aspartic acid or aspartate (Asp/D) residues may be converted to isoaspartic acid or isoaspartate via a deamidation-like reaction (also called isomerization) up to about 5%, 10%, 20%, 30%, 40%, 50%, 60%, 70%, 80%, 90% or 100% conversion per converted residue; (4) any one or more, up to all, glutamic acid or glutamate (Glu/E) residues may be converted to isoglutamic acid or isoglutamate via a deamidation-like reaction (also called isomerization) up to about 5%, 10%, 20%, 30%, 40%, 50%, 60%, 70%, 80%, 90% or 100% conversion per converted residue; or (5) a combination of the above.

As a non-limiting example, the disclosure encompasses CNP variants in which any one or more, up to all, asparagine, glutamine, aspartic acid, and/or glutamic acid residues of Pro-Gly-wtCNP37 [PGQEHPNARKYKGANKKGL-SKGCFGLKLDRIGSMSGLGC] (SEQ ID NO: 1) may be converted to (1) aspartic acid/aspartate and/or isoaspartic acid/isoaspartate, (2) glutamic acid/glutamate and/or isoglutamic acid/isoglutamate, (3) isoaspartic acid/isoaspartate, and/or (4) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue, as described above.

As a further example, the disclosure encompasses CNP variants in which any one or more, up to all, asparagine and/or aspartic acid residues of Pro-Gly-wtCNP37 [PGQEHPNARKYKGANKKGLSKGCFGLKLDRI-GSMSGLGC] (SEQ ID NO: 1) may be converted to (1) aspartic acid/aspartate and/or isoaspartic acid/isoaspartate, and/or (2) isoaspartic acid/isoaspartate, respectively, via deamidation or a deamidation-like reaction up to about 5%, 10%, 20%, 30%, 40%, 50%, 60%, 70%, 80%, 90% or 100% conversion per converted residue.

As another example, the present disclosure encompasses CNP variants in which any one or more, up to all, asparagine, glutamine, aspartic acid, and/or glutamic acid residues of Gly-wtCNP37 [GQEHPNARKYKGANKKGL-SKGCFGLKLDRIGSMSGLGC] (SEQ ID NO: 2) may be converted to (1) aspartic acid/aspartate and/or isoaspartic acid/isoaspartate, (2) glutamic acid/glutamate and/or isoglutamic acid/isoglutamate, (3) isoaspartic acid/isoaspartate, and/or (4) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue.

As yet another example, the disclosure encompasses CNP variants in which any one or more, up to all, asparagine, glutamine, aspartic acid, and/or glutamic acid residues of wtCNP37 [QEHPNARKYKGANKKGLSKGCFGLKL-DRIGSMSGLGC] (SEQ ID NO: 22) may be converted to (1) aspartic acid/aspartate and/or isoaspartic acid/isoaspartate, (2) glutamic acid/glutamate and/or isoglutamic acid/isoglutamate, (3) isoaspartic acid/isoaspartate, and/or (4) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue.

As a further example, the present disclosure encompasses CNP variants in which any one or more, up to all, asparagine, aspartic acid, and/or glutamic acid residues of an HSA-wtCNP27 chimera, GHKSEVAHRFKGANKKGL-SKGCFGLKLDRIGSMSGLGC (SEQ ID NO: 48), may be converted to (1) aspartic acid/aspartate and/or isoaspartic acid/isoaspartate, (2) isoaspartic acid/isoaspartate, and/or (3) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue.

As a still further example, the disclosure encompasses CNP variants in which any one or more, up to all, asparagine, aspartic acid, and/or glutamic acid residues of a Pro-HSA-wtCNP27 chimera, PGHKSEVAHRFK-GANKKGLSKGCFGLKLDRIGSMSGLGC (SEQ ID NO: 50), may be converted to (1) aspartic acid/aspartate and/or isoaspartic acid/isoaspartate, (2) isoaspartic acid/isoaspartate, and/or (3) isoglutamic acid/isoglutamate, respectively, via deamidation or a deamidation-like reaction up to about 5%, 10%, 20%, 30%, 40%, 50%, 60%, 70%, 80%, 90% or 100% conversion per converted residue.

In addition, the present disclosure encompasses CNP variants in which any one or more, up to all, methionine (Met/M) residues may be oxidized to any chemically feasible oxidized form (e.g., sulfoxide and/or sulfone) up to about 5%, 10%, 20%, 30%, 40%, 50%, 60%, 70%, 80%, 90% or 100% transformation per oxidized residue.

In another embodiment, the CNP variants comprise CNP22 or variants thereof conjugated at the N-terminus and/or C-terminus to moiet(ies) that facilitate translocation of the variants across a cell membrane or cell barrier. In one embodiment, the CNP variants are conjugated at the N-terminus and/or C-terminus to peptide sequence(s) that facilitate transport of the variants across a cell membrane or cell barrier, including via active peptide transporters.

In a further embodiment, the N-terminus and/or C-terminus of CNP22 or a variant thereof are conjugated to chemical moieties such as, e.g., natural and/or synthetic polymers, to increase the total mass of the modified CNP peptide to the ranges described generally herein, e.g., a range from about 2.6 or 2.8 kDa to about 6 or 7 kDa. In one embodiment, the chemical moieties are biocompatible hydrophilic or water-soluble natural (e.g., peptides, carbohydrates) or synthetic (e.g., PEG (or PEO)) polymers.

In a particular embodiment, the N-terminus and/or C-terminus of CNP22 or a variant thereof are conjugated to PEG (or PEO) polymers to result in a total mass characterized by the ranges described generally herein, e.g., from about 2.6 or 2.8 kDa to about 6 or 7 kDa. Pegylation of CNP22 or a variant thereof is designed, inter alia, to reduce immunogenicity and improve half-life by reducing renal clearance and increasing protease resistance. A PEG moiety can be attached to the N- and/or C-terminus of CNP22 or any variant described herein, including but not limited to CNP-17 (the Cys6-Cys22 cyclized portion of CNP22), CNP37, and variants of CNP17, CNP22, or CNP37 having N- and/or C-terminal amino acid extension(s), amino acid substitution(s) and/or amino acid deletion(s). In an embodiment, the Lys4 and/or Lys10 residues of CNP17, CNP22, or CNP37, or variants thereof, are substituted with a natural or unnatural amino acid (e.g., Arg, Gly, Ser, Gln, Glu, or Cit) or peptidomimetic that does not contain a reactive primary amine on a side chain, to preclude any potential PEGylation of these lysine residues. In one embodiment, the Lys4 and/or Lys10 residues of the CNP peptides are substituted with Arg. In another embodiment, the Lys10 residue is not substituted with Arg.

In a further embodiment, CNP variants (including CNP22 and variants thereof) having a PEG (or PEO) moiety and an amino acid extension at the N-terminus contain arginine at the position immediately preceding the position corresponding to Gly1 of CNP22. Such PEGylated CNP variants are designed for increased resistance to NEP degradation, reduced binding to serum albumin, and enhanced CNP functional activity (e.g., activation of cGMP signaling). Non-limiting examples of PEGylated CNP variants include PE024-GANRR-CNP22(K4R) (SEQ ID NO: 102), PEO12-GANRR-CNP22(K4R) (SEQ ID NO: 101), PE024-GANRR-CNP22 (SEQ ID NO: 103), PEO12-GANRR-CNP22 (SEQ ID NO: 104), PE024-GANPR-CNP22(K4R) (SEQ ID NO: 105), PEO12-GANPR-CNP22(K4R) (SEQ ID NO: 106), PE024-GANPR-CNP22 (SEQ ID NO: 107), PEO12-GANPR-CNP22 (SEQ ID NO: 108), PE024-GANQQ-CNP22 (SEQ ID NO: 109), PEO12-GANQQ-CNP22 (SEQ ID NO: 110), PE024-ER-CNP22(K4R) (SEQ ID NO: 111), PEO12-ER-CNP22(K4R) (SEQ ID NO: 112), PE024-ER-CNP22 (SEQ ID NO: 113), PEO12-ER-CNP22 (SEQ ID NO: 114), PE024-R-CNP22(K4R) (SEQ ID NO: 115), PEO12-R-CNP22(K4R) (SEQ ID NO: 116), PE024-R-CNP22 (SEQ ID NO: 117), and PEO12-R-CNP22 (SEQ ID NO: 118), wherein PE024 is a monodispersed 1.2 kDa PEG polymer and PEO12 is a monodispersed 0.6 kDa PEG polymer. In one embodiment, the PEG (or PEO) polymer is conjugated to the N-terminus of the CNP variants.

The disclosure contemplates use of hydrophilic or water soluble polymers (e.g., PEG) that can vary in type (e.g., homopolymer or copolymer; random, alternating or block copolymer; linear or branched; monodispersed or polydispersed), linkage (e.g., hydrolysable or stable linkage such as, e.g., amide, imine, aminal, alkylene, or ester bond), conjugation site (e.g., at the N-terminus and/or C-terminus, preferably not at any of the residues in the cyclized region of CNP (corresponding to residues 6-22 of CNP22)), and length (e.g., from about 0.2, 0.4 or 0.6 kDa to about 2, 3, 4 or 5 kDa). The hydrophilic or water-soluble polymer can be conjugated to the CNP peptide by means of N-hydroxy succinimide (NHS)- or aldehyde-based chemistry or other chemistry, as is known in the art. Such CNP variants can be generated using, e.g., wtCNP22 (2.2 kDa), CNP17 retaining only the cyclized region (residues 6-22) of wtCNP22, CNP variants having an amino acid extension at the N-terminus and/or C-terminus of CNP22 or CNP17, or variants having amino acid substitutions, additions and/or deletions such as, e.g., GANRR-CNP22(K4R) (SEQ ID NO: 119), GANPR-CNP22(K4R) (SEQ ID NO: 78), R-CNP22 (SEQ ID NO: 71), R-CNP22(K4R) (SEQ ID NO: 79), ER-CNP22 (SEQ ID NO: 72), and ER-CNP22(K4R) (SEQ ID NO: 80). In an embodiment, the PEG-CNP variants having a total mass characterized by the ranges described generally herein, e.g., from about 2.6 or 2.8 kDa to about 6 or 7 kDa, contain a monodispersed, linear PEG (or PEO) moiety conjugated at the N-terminus and/or C-terminus via NHS- or aldehyde-based chemistry, or a two-arm or three-arm branched PEG moiety conjugated at the N-terminus and/or C-terminus via NHS-based chemistry. The disclosure also encompasses negatively charged PEG-CNP variants designed for reduced renal clearance, including but not limited to carboxylated, sulfated and phosphorylated compounds (Caliceti, Adv. Drug Deliv. Rev., 55: 1261-77 (2003); Perlman, J. Clin. Endo. Metab., 88: 3227-35 (2003); Pitkin, Antimicrob. Ag. Chemo., 29: 440-444 (1986); Vehaskari, Kidney Intl, 22: 127-135 (1982)). In one embodiment, the PEG (or PEO) moiety contains carboxyl group(s), sulfate group(s), and/or phosphate group(s).

In another embodiment, the PEG (or PEO) moieties conjugated to the N-terminus, C-terminus and/or internal site(s) of CNP variants described herein contain one or more functional groups that are positively charged under physiological conditions. Such PEG moieties are designed, inter alia, to improve distribution of such PEGylated CNP variants to cartilage tissues. In one embodiment, such PEG moieties contain one or more primary, secondary or tertiary amino groups, quaternary ammonium groups, and/or other amine-containing (e.g., urea) groups.

In an embodiment, the disclosure encompasses CNP22 or variants thereof conjugated via NHS— or aldehyde-based chemistry to PEG (or PEO) of the formula $(CH_2CH_2O)_n$, wherein n is an integer from about 6 to about 100, and the PEG polymer is from about 0.3 kDa to about 5 kDa. In another embodiment, n is an integer from about 12 to about 50, and the PEG polymer is from about 0.6 kDa to about 2.5 kDa. In yet another embodiment, n is from about 12 to about 24, and the PEG polymer is from about 0.6 kDa to about 1.2 kDa. In still another embodiment, the terminal hydroxyl group of the PEG polymer is capped with a non-reactive group. In a particular embodiment, the end-capping group is an alkyl group, e.g., a lower alkyl group such as methyl.

In a further embodiment, the disclosure provides CNP variants having one or more peptide bonds or peptide bond isosteres that have reduced susceptibility to cleavage by peptidases including neutral endopeptidase (NEP). NEP is a membrane-bound zinc-dependent endopeptidase that cleaves a substrate peptide bond at the amino end of large hydrophobic residues. Thus, modification of a peptide bond at a cleavage site for NEP to an unnatural peptide or non-peptide bond may preclude or decrease the efficiency of NEP cleavage.

For ANP and CNP, NEP cleavage is reported to occur first at the Cys6-Phe7 bond within the cyclized region, then elsewhere throughout the remainder of the structures. For BNP, cleavage is reported to occur first at the peptide N-terminus, then within the cyclic structure. Although the primary NEP cleavage site on CNP is reported to be the Cys6-Phe7 bond, when wtCNP22 was exposed to NEP digestion for 2.5 minutes in vitro, all possible sites were unexpectedly hydrolyzed, with the Cys6-Phe7 and Gly8-Leu9 peptide bonds being slightly most labile.

Substrate specificity of NEP is primarily determined by two substrate-binding substitutes, S1' and S2' (Oefner et al., J. Mol. Biol. 296:341-349 (2000)). The S1' site accepts a large hydrophobic P1' residue of which the N-terminal peptide bond is subjected to hydrolysis (e.g., Phe, Leu, Be, and Met). The S2' site generally prefers a smaller residue, termed P2' (e.g., Gly or Ser). In the case of CNP, Phe7 is reported to be the preferred P1' residue for the NEP S1' site, while Gly8 is the preferred P2' residue for the S2' site. Because these two substitutes can together accommodate only a certain total side chain size, any increase in the total size of the P1'-P2' residues of CNP can potentially disrupt NEP binding. For example, addition of a chloride atom at the 3-position of the P1' Phe7 aromatic ring (i.e., 3-Cl-Phe7) can potentially modify (e.g., destabilize) interactions between CNP and the NEP cleavage sites, for example at the S1' subsite. Addition of a tertiary butyl group to the smaller P2' residue Gly8 (i.e., tBu-Gly8) can potentially disrupt the interaction between CNP and the S2' subsite.

Accordingly, in one embodiment, CNP variants of the disclosure include CNP having an increase in the size of the P1'-P2' residues, such as Phe7-Gly8, to interfere with substrate recognition at the active site, thereby reducing susceptibility to NEP cleavage. Natural amino acids, unnatural amino acids and/or peptidomimetic moieties are substituted for one or more large P1' hydrophobic residues, including but not limited to Phe7, Leu9, Leu11, Ile14, Met17 and Leu20, and/or for one or more smaller P2' residues, including but not limited to Cys6, Gly8, Gly15, Ser16 and Gly19.

The disclosure encompasses CNP variants comprising at least one modified amino acid and/or at least one modified peptide bond, at least one residue involved in substrate recognition and/or cleavage by NEP, wherein the modified amino acids and modified peptide bonds can be natural amino acids, unnatural amino acids, peptidomimetics and/or peptide bond isosteres. In one embodiment, the NEP cleavage site on CNP between Cys6 and Phe7 is modified. In a related embodiment, the peptide bond (—C(=O)—NH—) between Cys6 and Phe7 is replaced with one of the following peptide bond isosteres:
- —CH$_2$—NH—,
- —C(=O)—N(R)—, where the amide group is alkylated with any of the following R groups: methyl, ethyl, n-propyl, isopropyl, cyclopropyl, n-butyl, isobutyl, sec-butyl, or tert-butyl,
- —C(=O)—NH—CH$_2$—,
- —CH$_2$—S—,
- —CH$_2$—S(O)$_n$—, where n is 1 or 2,
- —CH$_2$—CH$_2$—,
- —CH=CH—,
- —C(=O)—CH$_2$—,
- —CH(CN)—NH—,
- —CH(OH)—CH$_2$—,
- —O—C(=O)—NH—, or
- —NHC(=O)NH—.

In another embodiment, the CNP variants are represented by the formula: (x)-Gly$_1$-Leu$_2$-Ser$_3$-Lys$_4$-Gly$_5$-(b)$_6$-(c)$_7$-(d)$_8$-Leu$_9$-Lys$_{10}$-Leu$_{11}$-Asp$_{12}$-Arg$_{13}$-Ile$_{14}$-Gly$_{15}$-Ser$_{16}$-Met$_{17}$-Ser$_{18}$-Gly$_{19}$-Leu$_{20}$-Gly$_{21}$-Cys22-(z) (SEQ ID NO: 120), wherein:
- (x) and (z) independently may be absent or may be selected from the group consisting of synthetic bone-targeting compounds such as, e.g., bisphosphonates; amino acid sequences useful in joint or cartilage targeting such as, e.g., polyAsp and polyGlu; amino acid sequences derived from bone-targeting domains of bone proteins such as, e.g., osteopontin, osteocalcin, and sialoprotein (Wang et al., Adv. Drug Delivery Rev., 57: 1049-76 (2005)); polymeric and non-polymeric molecules that reduce renal clearance such as, e.g., negatively charged PEGs; and natural polymers (e.g., those containing amino acids, fatty acids and/or carbohydrates) and synthetic polymers (e.g., PEGs) that increase resistance of the CNP variant to NEP degradation by increasing the total mass of the CNP variant to the ranges described generally herein, e.g., from about 2.6 or 2.8 kDa to about 6 or 7 kDa;
- (b) and (c) may be the wild-type Cys6 and Phe7, another natural amino acid or an unnatural amino acid, or may contain a peptide bond isostere as described herein to increase resistance to NEP cleavage; and
- (d) may be the wild-type Gly8, or may be a larger natural or unnatural (e.g., t-Bu-Gly) amino acid or peptidomimetic to reduce binding to NEP.

In one embodiment, such CNP variants contain at least one modified amino acid at (b), (c) and/or (d).

Other peptide bonds within CNP may be cleaved even if CNP22 or a variant thereof has an NEP-resistant peptide bond or peptide bond isostere at Cys6-Phe7, including the Gly8-Leu9, Lys10-Leu11, Arg13-Ile14, Ser16-Met17, and Gly19-Leu20 bonds. Therefore, the disclosure encompasses CNP variants having peptide bond isostere(s) at one or more other NEP cleavages sites in addition to the Cys6-Phe7 bond, wherein the peptide bond isosteres include those described herein.

In another embodiment, the disclosure encompasses CNP variants having a cysteine analog at Cys6 and/or Cys22, including but not limited to homocysteine, penicillamine, 2-mercaptopropionic acid, and 3-mercaptopropionic acid. In an embodiment, such CNP variants have a cyclic domain formed by a disulfide bond between the wild-type Cys6 or analog and Cys22 or analog. In yet another embodiment, one or more residues of CNP22 or a variant thereof, up to all the residues, are substituted with a D-amino acid. Substitution of an L-amino acid with a D-amino acid essentially moves the side chain about 120 degrees from its original position, thereby potentially disrupting the binding of the CNP peptide to NEP. In a specific embodiment, L-Phe at Phe7 is substituted with its D-enantiomer, D-Phe.

In still another embodiment, a beta amino acid such as, e.g., 3-amino-2-phenylpropionic acid (or 2-phenyl-beta-alanine), replaces the wild-type alpha-amino acid Phe7. Use of a beta-amino acid effectively increases the peptide backbone length by one methylene unit. Protease resistance can result from the change in substrate conformation or the increased distance between amino acid side chains.

Non-limiting examples of variants of CNP22 having an unnatural alpha-amino acid, a beta-amino acid or a peptide bond isostere include:

(Analog A)
                                            (SEQ ID NO: 121)
GLSKGC(CH₂NH)FGLKLDRIGSMSGLGC;

(Analog B)
                                            (SEQ ID NO: 122)
GLSKGC-(N-Me-Phe)-GLKLDRIGSMSGLGC;

(Analog E)
                                            (SEQ ID NO: 123)
GLSKGC-(D-Phe)-GLKLDRIGSMSGLGC;

(Analog F)
                                            (SEQ ID NO: 124)
GLSKGCF-(tBu-Gly)-LKLDRIGSMSGLGC;

(Analog G)
                                            (SEQ ID NO: 125)
GLSKGC-(3-Cl-Phe)-GLKLDRIGSMSGLGC;
and (Analog H, formed using 3-amino-2-phenylpropionic
acid)
                                            (SEQ ID NO: 126)
GLSKGC-[NHCH₂CH(Ph)CO]-GLKLDRIGSMSGLGC.

In a further embodiment, the CNP variants have a total mass characterized by the ranges described generally herein, e.g., from about 2.6 or 2.8 kDa to about 6 or 7 kDa, designed for increased resistance to NEP degradation, and are represented by the formula: $(x)\text{-Gly}_1\text{-Leu2-Ser}_3\text{-(a)}_4\text{-Gly}_5\text{-(b)}_6\text{-(c)}_7\text{-(d)}_8\text{-(e)}_9\text{-(f)}_{10}\text{-(g)}_{11}\text{-Asp}_{12}\text{-Arg}_{13}\text{-(h)}_{14}\text{-Gly}_{15}\text{-Ser}_{16}\text{-(i)}_{17}\text{-Ser}_{18}\text{-Gly19-(j)}_{20}\text{-Gly}_{21}\text{-Cys}_{22}\text{-(z)}$ (SEQ ID NO: 127), wherein:

(x) and (z) independently may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone-targeting domains of bone proteins such as, e.g., osteopontin, osteocalcin, and sialoprotein; polymeric and non-polymeric moieties that reduce renal clearance such as, e.g., negatively charged PEGs; polymers containing, e.g., amino acids, hydrophobic acids, and/or carbohydrates; and synthetic hydrophilic polymers such as, e.g., PEGs;

(a) may be the wild-type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser, or Glu, wherein in one embodiment (a) is Arg; (b) is selected from the group consisting of Cys and peptide-bond isosteres between Cys6 and Phe7 such as, e.g., Cys-CH₂—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl, or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched $C_{1-6}$ alkyl, straight or branched $C_{1-6}$ alkoxy, straight or branched halo-$C_{1-6}$ alkyl, $C_{3-10}$ cycloalkyl, heterocyclyl, $C_{6-14}$ aryl and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly (tBu-Gly), Thr, Ser, Val, and Asn;

(e) is selected from the group consisting of Leu, Ser, Thr, and peptide-bond isosteres such as, e.g., N-Me-Leu;

(f) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser, or Glu, wherein in one embodiment (f) is not Arg;

(g) is selected from the group consisting of Leu and peptide-bond isosteres such as, e.g., N-Me-Leu;

(h) is selected from the group consisting of Ile, tBu-Gly, and peptide-bond isosteres such as, e.g., N-Me-Ile;

(i) is selected from the group consisting of Met, Val, Asn, beta-Cl-Ala, 2-aminobutyric acid (Abu), and 2-amino-isobutyric acid (Aib); and (j) is selected from the group consisting of Leu, norleucine (Nle), homoleucine (Hleu), Val, tert-butyl-Ala (tBu-Ala), Ser, Thr, Arg, and peptide-bond isosteres such as, e.g., N-Me-Leu.

In another embodiment, the CNP variants have a total mass characterized by the ranges described generally herein, e.g., from about 2.6 or 2.8 kDa to about 6 or 7 kDa, designed for increased resistance to NEP cleavage, and are represented by the formula: $(x)\text{-Gly}_1\text{-Leu}_2\text{-Ser}_3\text{-(a)}_4\text{-Gly}_5\text{-(b)}_6\text{-(c)}_7\text{-(d)}_8\text{-(e)}_9\text{-(f)}_{10}\text{-(g)}_{11}\text{-Asp}_{12}\text{-Arg}_{13}\text{-(h)}_{14}\text{-(i)}_{15}\text{-Ser}_{16}\text{-(j)}_{17}\text{-Ser}_{18}\text{-Gly19-(k)}_{20}\text{-Gly}_{21}\text{-Cys}_{22}\text{-(z)}$ (SEQ ID NO: 128), wherein:

(x) and (z) independently may be absent or may be selected from the group consisting of synthetic bone-targeting compounds such as, e.g., bisphosphonates; amino acid sequences useful in bone or cartilage targeting such as, e.g., polyAsp and polyGlu; amino acid sequences derived from bone-targeting domains of bone proteins and derivatives thereof, such as, e.g., fusion proteins or peptide sequences of osteopontin, osteocalcin, sialoprotein, etc.; moieties that reduce renal clearance, including but not limited to hydrophilic or water-soluble polymers such as, e.g., charged PEG molecules; and moieties comprising, e.g., PEGs, amino acids, carbohydrates, and/or hydrophobic acids;

(a) may be the wild type Lys at that position or may be replaced with a conservative amino acid substitution or a natural or unnatural amino acid or peptidomimetic that does not have a reactive primary amine on a side chain, including but not limited to Arg, Gly, 6-hydroxy-norleucine, citrulline (Cit), Gln, Ser, or Glu, wherein in one embodiment (a) is Arg;

(b) is selected from the group consisting of Cys and peptide bond isosteres between Cys6 and Phe7 such as, e.g., Cys-CH$_2$—NH;

(c) is selected from the group consisting of L-Phe; D-Phe; 3-amino-2-phenylpropionic acid; N-alkylated derivatives of Phe, wherein the N-alkyl group is methyl, ethyl, n-propyl, isopropyl, cyclopropyl, n-butyl, isobutyl, sec-butyl or tert-butyl; and Phe analogs, wherein one or more ortho-, meta-, and/or para-positions of the benzene ring of the Phe analog are substituted with one or more substituents selected from the group consisting of halogen, hydroxyl, cyano, straight or branched $C_{1-6}$ alkyl, straight or branched $C_{1-6}$ alkoxy, straight or branched halo-$C_{1-6}$ alkyl, $C_{3-10}$ cycloalkyl, $C_{6-14}$ aryl, heterocyclyl, and heteroaryl (examples include, but are not limited to, tyrosine, 3-chlorophenylalanine, 2,3-chloro-phenylalanine, 3-chloro-5-fluoro-phenylalanine, 2-chloro-6-fluoro-3-methyl-phenylalanine), or wherein the benzene ring of the Phe analog can be replaced with another aryl group (non-limiting examples include 1- and 2-naphthylalanine) or with a heteroaryl group (non-limiting examples include pyridylalanine, thienylalanine and furylalanine);

(d) is selected from the group consisting of Gly, tert-butyl-Gly, Thr, Ser, Val, and Asn;

(e) is selected from the group consisting of Leu, Ser, Thr, and peptide bond isosteres such as, e.g., N-Me-Leu;

(f) is selected from the group consisting of Lys, Arg, Gly, 6-hydroxy-norleucine, citrulline (Cit), Gln, and Ser;

(g) is selected from the group consisting of Leu, Asn, and peptide bond isosteres such as, e.g., N-Me-Leu;

(h) is selected from the group consisting of Ile, tert-butyl-Gly (tBu-Gly), Asn, and peptide bond isosteres such as, e.g., N-Me-Ile;

(i) is selected from the group consisting of Gly, Arg, Ser, and Asn;

(j) is selected from the group consisting of Met, Val, Asn, beta-Cl-Ala, 2-aminobutyric acid (Abu), and 2-amino-isobutyric acid (Aib); and (k) is selected from the group consisting of Leu, norleucine (Nle), homoleucine (Hleu), Val, tert-butyl-Ala (tBu-Ala), Arg, Thr, Ser, and peptide bond isosteres such as, e.g., N-Me-Leu.

To improve the delivery of the CNP variants to the target sites of joint-related disorders (e.g., osteoarthritis), the CNP variants can be attached (e.g., at the N-terminus and/or C-terminus) to bone- or cartilage-targeting moieties. Non-limiting examples of bone- or cartilage-targeting moieties include bisphosphonates; hydroxyapatite; glucosamine; collagen (e.g., collagen type X); polyAsp; polyGlu; and amino acid sequences derived from bone-targeting domains of bone proteins such as, e.g., osteocrin, osteopontin, osteocalcin, and sialoprotein.

In addition to being less susceptible to NEP cleavage, the CNP variants potentially have reduced affinity to the NPR-C clearance receptor, while retaining CNP functionality. Besides NEP-mediated degradation, the half-life of CNP22 is influenced by the clearance receptor, NPR-C, which shares 58% sequence homology with the extracellular peptide-binding domain of NPR-B. CNP22 binds tightly to not only NPR-B (7-30 pM affinity), but also NPR-C(11-140 pM) (Bennett, B. D. et al., J. Biol. Chem., 266: 23060-67 (1991); Koller, K. J. & Goeddel, D. V., Circulation, 86: 1081-88 (1992); Suga, S. et al., Endocrinology, 130: 229-39 (1992)). Even though the NPR-B crystal structure has yet to be reported, sequence homology as well as similarities between the NPR-C and NPR-A crystal structures (He, X.-L. et al., Science, 293(5535): 1657-62 (2001); Ogawa, H. et al., J. Biol. Chem., 279(27): 28625-31 (2004); He, X.-L., J. Mol. Biol., 361(4): 698-714 (2006)) suggest that NPR-B likely assumes a similar overall structural fold.

Therefore, an NPR-B homology model was built based on structure-based sequence alignment and crystallographic structures of the following related systems: CNP bound to NPR-C, ANP bound to NPR-A, and ANP bound to NPR-C (He, X.-L. et al., Science, 293(5535): 1657-62 (2001); Ogawa, H. et al., J. Biol. Chem., 279(27): 28625-31 (2004); He, X.-L., J. Mol. Biol., 361(4): 698-714 (2006)). Based on observations that the receptor appears to determine the bound peptide conformation, and that NPR-B most closely resembles NPR-A with respect to primary structure and functional properties, the NPR-B/CNP homology model was built with the NPR-A/ANP crystal structure as a model. Published signaling data of CNP variants (U.S. Pat. No. 5,434,133 and US Patent Application Publication No. 2004/0138134 A1), and of functional ANP variants that no longer bind to NPR-C (Cunningham, EMBO 13(11) 2508-15, 1994) were used to refine and interpret the NPR-B/CNP model.

The present disclosure encompasses CNP variants designed for improved NPR-B selectivity based on a homology-based structural model of the NPR-B/CNP complex. Combining the experimental and computational structure data of natriuretic peptides bound to the various receptors with the published functional data, CNP variants were generated that continue to bind to NPR-B, but can potentially have reduced affinity to the NPR-C clearance receptor. For example, NPR-C has a unique insertion in a loop structure in the peptide-binding site, placing its loop residues closer to such peptide residues as CNP Gly8 (or ANP Gly9), compared to respective loop residues in NPR-A and NPR-B. Earlier studies indicated that the G9T mutation in ANP contributes to reduce affinity to NPR-C, thereby improving NPR-A selectivity (Cunningham, EMBO J., 13(11): 2508-15 (1994)). Accordingly, CNP variants were generated to replace the corresponding Gly8 residue with a larger residue (Ser, Val, Thr, or Asn) to disrupt the CNP binding to NPR-C without affecting its binding to NPR-B. Further, one or more mutations were introduced at the C-terminal end of CNP, encompassing Gly15 to Gly21, which is predicted to interact with receptor-specific residues, based on the detailed structural analyses of the receptor/peptide complexes. For example, a G19R mutation in CNP22 does not result in a significant loss of NPR-B signaling activity. This mutation, however, cannot be modeled into the available crystal structure of NPR-C/CNP without altering the conformations of neighboring residues. These observations suggest that the G19R mutation may selectively disrupt the binding of CNP to a particular receptor, such as NPR-C.

In an embodiment, the CNP variants have substitution(s) at one or more Gly sites at positions 1, 5, 8, 15, 19 and 21, to reduce conformational flexibility and thereby increase receptor specificity. Comparative analyses of crystal structures of ANP bound to NPR-C and NPR-A (Ogawa, H. et al., J. Biol. Chem., 279: 28625-31 (2004); He, X.-L., J. Mol.

Biol., 361: 698-714 (2006)) indicate that the conformational flexibility of ANP may play an important role in determining the receptor selectivity.

In one embodiment, functional CNP variants with potentially reduced affinity to NPR-C have one or more of the following amino acid substitutions: G1R, G1E, GSR, G5Q, G5S, F7Y, G8T, GBS, G8V, G8N, L9S, L9T, K10Cit, K10Q, K10S, I14N, G15R, G15S, G15N, G15Cit, S16Q, M17V, M17N, G19S, G19R, G19N, L20V, L20R, L20T, L20S, G21S, G21T, and G21R. In an embodiment, the CNP variants have multipoint substitutions at positions 1, 5, 7, 8, 9, 10, 14, 15, 16, 17, 19, 20, and/or 21, and may optionally have modifications at any of the other positions in the peptide sequence of the variant.

In a further embodiment, the CNP variants described herein may be conjugated to moieties, up to a total mass characterized by the ranges described generally herein, e.g., from about 2.6 or 2.8 kDa to about 6 or 7 kDa, at the N-terminus, the C-terminus and/or an internal site, to facilitate joint/cartilage targeting, reduce NPR-C and renal clearance, increase resistance to NEP degradation, and/or improve CNP functionality. In one embodiment, the CNP variants are not conjugated to a polymeric moiety at a site within the cyclic region (corresponding to Cys6 to Cys22 of CNP22). Non-limiting examples of polymeric or non-polymeric moieties that can be conjugated to the CNP variants include synthetic bone-targeting compounds such as, e.g., bisphosphonates; bone/cartilage targeting peptide sequences such as, e.g., polyAsp and polyGlu; peptide sequences derived from bone-targeting domains of bone proteins such as, e.g., osteopontin, osteocalcin and sialoprotein; peptide sequences derived from the functional domains of bone morphogenetic proteins such as, e.g., BMP2, BMP3, BMPS, BMP7, and BMP8a; peptide sequences derived from polypeptides of natriuretic origin such as, e.g., NPPC, ANP, and BNP; other natural polymeric or non-polymeric moieties such as, e.g., carbohydrates, fatty acids and phospholipids; biocompatible synthetic hydrophilic polymers such as, e.g., PEG (or PEO); hydrophobic polymeric or non-polymeric moieties such as, e.g., heptanoic acid and pentanoic acid; and combinations thereof.

The CNP variants described herein can have substantially similar or better functional activity than CNP22, e.g., with respect to stimulation of cGMP production and signaling. In one embodiment, the CNP variants in vitro or in vivo stimulate the production of at least about 50% of the cGMP level produced under the same concentration of wtCNP22 (e.g., 1 µM). In certain embodiments, the CNP variants retain at least about 50%, 60%, 70%, 80%, 90%, 95%, or 100% of the cGMP-stimulation activity of wild-type CNP22 in vitro or in vivo. In another embodiment, the CNP variants have improved cGMP-stimulation activity compared to CNP22. In certain embodiments, the CNP variants in vitro or in vivo stimulate the production of at least about 110%, 120%, 130%, 140%, 150%, 200%, 250%, 300%, 350%, 400%, 450%, 500% or more of the cGMP level produced under the same concentration of wtCNP22 (e.g., 1 µM).

C. SYNTHESIS AND PURIFICATION OF CNP VARIANTS

In some embodiments, the CNP variants useful herein are produced by recombinant expression, using certain techniques known in the art in certain embodiments. See, e.g., Sambrook, Fritsch & Maniatis, Molecular Cloning: A Laboratory Manual, Second Edition. Cold Spring Harbor Laboratory Press (Cold Spring Harbor, N.Y. (1989)); DNA Cloning: A Practical Approach, Volumes I and II, D. N. Glover, Ed. (1985); and Current Protocols in Molecular Biology, John Wiley & Sons, Inc. (1994).

In certain embodiments, the CNP variants are produced by a recombinant process that comprises culturing in a medium a host cell comprising a first polynucleotide encoding a CNP variant polypeptide linked to a second polynucleotide encoding a cleavable peptide or protein under conditions that result in expression of a fusion polypeptide encoded by the polynucleotides, wherein the fusion polypeptide comprises the CNP variant polypeptide directly linked to the cleavable peptide or protein or indirectly linked thereto via a linker. In some embodiments, the host cell is transformed with an expression vector comprising the polynucleotide encoding the CNP variant polypeptide linked to the polynucleotide encoding the cleavable peptide or protein. In certain embodiments, the fusion polypeptide is expressed as a soluble protein or as an inclusion body. The expressed fusion polypeptide can be isolated from the host cell or culture medium, and the isolated fusion polypeptide can be contacted with a cleaving agent to release the CNP variant.

Methods of producing CNP variants are described in U.S. Pat. Nos. 8,198,242, 8,377,884 and 8,598,121, herein incorporated by reference.

D. CHEMICALLY MODIFIED CNP VARIANTS

Chemical modification of CNP variants can potentially impart advantageous properties to the modified CNP peptides, such as increased stability and half-life and reduced immunogenicity (for a general discussion of chemical modification of therapeutic proteins, see Pharmazie, 57(1): 5-29 (2002)). In addition to PEGylation, glycosylation and other chemical derivatization procedures, e.g., modification by phosphorylation, amidation, carboxylation, acetylation, methylation, and creation of acid-addition salts, amides, esters and N-acyl derivatives, may also mask potentially immunogenic regions and/or proteolytically sensitive regions (Science, 303: 480-482 (2004)).

Examples of chemical modifications include, without limitation, the polymer addition method of Bednarsaki and the cross-linking method of Altus Corporation for improving stability and protease resistance and reducing immunogenicity. Bednarsaki showed that polymer addition can improve protein temperature stability (J. Am. Chem. Soc., 114(1): 378-380 (1992)), and Altus Corporation found that glutaraldehyde cross-linking can improve enzyme stability.

Chemical modification of polypeptides can be performed in a non-specific fashion (leading to mixtures of derivatized species) or in a site-specific fashion (e.g., based on wild-type macromolecule reactivity-directed derivatization and/or site-selective modification using a combination of site-directed mutagenesis and chemical modification) or, alternatively, using expressed protein ligation methods (Curr. Opin. Biotechnol., 13(4): 297-303 (2002)).

Pegylated CNP Variants

In one embodiment, for increased stability CNP variants (including those having amino acid additions, substitutions and/or deletions) are conjugated to hydrophilic, natural or synthetic polymers. In an embodiment, the hydrophilic polymers are water-soluble so that the CNP peptides conjugated thereto do not precipitate out in an aqueous (e.g., physiological) environment. Further, the hydrophilic polymers are biocompatible, i.e., do not cause injury, toxicity or an immunological reaction in vivo. The hydrophilic polymers can be branched or unbranched. In one embodiment, the hydrophilic polymers are not branched.

Various sites of conjugation of a CNP variant to a hydrophilic polymer are possible, including but not limited to: (1) only at the N-terminus; (2) only at the C-terminus; (3) only at an internal site (e.g., Lys4); (4) at both the N-terminus and the C-terminus; (5) at the N-terminus and an internal site; and (6) at the C-terminus and an internal site. In one embodiment, CNP variants are conjugated to a hydrophilic polymer only at the N-terminus. In another embodiment, conjugation is only at an internal site (e.g., Lys4). In yet another embodiment, conjugation is at the N-terminus and an internal site (e.g., Lys4). In still another embodiment, for better functionality the CNP variants are not conjugated to a hydrophilic polymer at a site (e.g., Lys10) within the cyclic domain (corresponding to Cys6 to Cys22 of CNP-22). If conjugation to a hydrophilic polymer is based on bond formation with a reactive primary amino group on the CNP variant, conjugation at an internal site (e.g., Lys4 and/or Lys10) can be prevented by substitution of Lys4 and/or Lys10 with a natural or unnatural amino acid or peptidomimetic that does not contain a reactive primary amino group on a side chain, such as, e.g., Gly, Ser, Arg, Asn, Gln, Asp, Glu or citrulline (Cit). In a particular embodiment, Lys4 and/or Lys10 are replaced with Arg. In another embodiment, Lys10 is not replaced with Arg.

Non-limiting examples of hydrophilic polymers include polymers formed from carboxylic acid-bearing monomers (e.g., methacrylic acid (MA) and acrylic acid (AA)), polyvinyl alcohols, polymers formed from hydroxyl-bearing monomers (e.g., hydroxyethyl methacrylate (HEMA), hydroxypropyl methacrylate (HPMA), hydroxypropyl methacrylamide, and 3-trimethylsilylpropyl methacrylate (TMSPMA)), polyalkylene oxides, polyoxyethylated polyols (e.g., glycerol), poly(ethylene glycol) (PEG), poly(propylene glycol), mono-$C_1$-$C_{10}$ alkoxy-PEGs (e.g., monomethoxy-PEG), tresyl monomethoxy-PEG, aryloxy-PEGs, PEG acrylate (PEGA), PEG methacrylate, PEG propionaldehyde, bis-succinimidyl carbonate PEG, copolymers of 2-methacryloyloxyethyl-phosphorylcholine (MPC) and N-vinyl pyrrolidone (VP), hydroxy functional poly(N-vinyl pyrrolidone) (PVP), SIS-PEG (SIS is polystyrene-polyisobutylene-polystyrene block copolymer), polystyrene-PEG, polyisobutylene-PEG, PCL-PEG (PCL is polycaprolactone), PLA-PEG (PLA is polylactic acid), PMMA-PEG (PMMA is poly(methyl methacrylate)), PDMS-PEG (PDMS is polydimethyloxanone), PVDF-PEG (PVDF is polyvinylidene fluoride), PLURONIC™ surfactants (polypropylene oxide-co-polyethylene glycol), poly(tetramethylene glycol), poly(L-lysine-g-ethylene glycol) (PLL-g-PEG), poly (L-lysine-g-hyaluronic acid) (PLL-g-HA), poly(L-lysine-g-phosphoryl choline) (PLL-g-PC), poly(L-lysine-g-vinyl pyrrolidone) (PLL-g-PVP), poly(ethylimine-g-ethylene glycol) (PEI-g-PEG), poly(ethylimine-g-hyaluronic acid) (PEI-g-HA), poly(ethylimine-g-phosphoryl choline) (PEI-g-PC), poly(ethylimine-g-vinyl pyrrolidone) (PEI-g-PVP), PLL-co-HA, PLL-co-PC, PLL-co-PVP, PEI-co-PEG, PEI-co-HA, PEI-co-PC, PEI-co-PVP, cellulose and derivatives thereof (e.g., hydroxyethyl cellulose), dextran, dextrins, hyaluronic acid and derivatives thereof (e.g., sodium hyaluronate), elastin, chitosan, acrylic sulfate, acrylic sulfonate, acrylic sulfamate, methacrylic sulfate, methacrylic sulfonate, methacrylic sulfamate, polymers and copolymers thereof, and polymers and copolymers of combinations thereof.

In a particular embodiment, the hydrophilic polymer is poly(ethylene glycol) (PEG), also called poly(ethylene oxide) (PEO). As used herein, the term "PEG" or "PEO" encompasses all the forms of PEG, branched and unbranched, which can be used to derivatize polypeptides, including without limitation mono-($C_1$-$C_{10}$) alkoxy-PEGs and aryloxy-PEGs.

In one embodiment, the PEG-CNP conjugates comprise a PEG (or PEO) polymer of the formula $(CH_2CH_2O)_n$, wherein n is an integer from about 6 to about 100, and the PEG polymer is from about 0.3 kDa to about 5 kDa. In another embodiment, n is an integer from about 12 to about 50, and the PEG polymer is from about 0.6 kDa to about 2.5 kDa. In yet another embodiment, n is from about 12 to about 24, and the PEG polymer is from about 0.6 kDa to about 1.2 kDa. In a further embodiment, the terminal hydroxyl group of the PEG polymer is capped with a non-reactive group. In a particular embodiment, the end-capping group is an alkyl group, e.g., a lower alkyl group such as methyl, so that the PEG polymer terminates in an alkoxy group. In an embodiment, the PEG polymer is not branched. In another embodiment, CNP-22 or variants thereof are conjugated to a PEG polymer only at the N-terminus.

PEGs and PEOs potentially include molecules with a distribution of molecular weights, i.e., they are potentially polydispersed, depending on the manner in which they are prepared. The size/mass distribution of a polymeric preparation can be characterized statistically by its weight average molecular weight ($M_w$) and its number average molecular weight ($M_n$), the ratio of which is called the polydispersity index ($M_w/M_n$). $M_w$ and $M_n$ can be measured by mass spectroscopy. PEG-CNP variants conjugated to a PEG moiety larger than 1.5 kDa may exhibit a range of molecular weights due to the polydispersed nature of the parent PEG molecule. For example, in the case of mPEG2K (Sunbright ME-020HS, NOF Co.), the molecular masses of the PEG molecules are distributed over a range from about 1.5 kDa to about 3 kDa, with a polydispersity index of 1.036. By contrast, the PEGs conjugated to CNP-22 or variants thereof using MS(PEG)$_n$ reagents (n=4, 8, 12 or 24, denoted as, e.g., "PEO12" or "PEO24") from Pierce Biotechnology (Rockford, Illinois) are monodispersed, having discrete chain length and defined molecular weight.

Methods for generating polypeptides comprising a PEG moiety are known in the art (see, e.g., U.S. Pat. No. 5,824,784). Methods for preparing PEGylated CNP peptides generally comprise the steps of (a) reacting CNP-22 or a variant thereof with a PEGylation reagent under conditions suitable for attaching PEG to the CNP peptide (e.g., at the N-terminus), and (b) obtaining the reaction product(s). Because PEGylating a CNP peptide might significantly alter its binding to NPR-B, depending on the size of the PEG moiety and the location of PEGylation, different kinds of PEG and PEGylation reaction conditions can be explored. The chemistry that can be used for PEGylation of a CNP peptide includes acylation of reactive primary amine(s) of the peptide using the NHS-ester of methoxy-PEG (O—[(N-Succinimidyloxycarbonyl)-methyl]-O'-methylpolyethylene glycol). Acylation with methoxy-PEG-NHS or methoxy-PEG-SPA results in an amide linkage that eliminates any charge of the original primary amine. PEG-CNP variants designated with the symbol "PEO12" or "PEO24", as well as those designated with the symbol "PEG1K", "PEG2K", "PEG5K" or "PEG20K", are PEGylated via reaction of a primary amino group on the peptide with an NHS ester-activated, methoxy-end capped PEG reagent. PEG-CNP variants can also be prepared by other methods, e.g., via reductive amination involving a primary amino group on the peptide and a PEG aldehyde, such as, e.g., PEG-propionaldehyde, or mono-$C_1$-$C_{10}$ alkoxy or aryloxy derivatives thereof (see U.S. Pat. No. 5,252,714).

Unlike ribosome protein synthesis, synthetic peptide synthesis proceeds from the C-terminus to the N-terminus. Accordingly, Boc-PEG (containing tert-butyloxycarbonyl (Boc)) is one method to attach PEG to the C-terminus of a peptide (R. B. Merrifield, J. Am. Chem. Soc., 85(14): 2149-2154 (1963)). Alternatively, Fmoc (fluorenylmethoxycarbonyl) chemistry can be employed (E. Atherton and R. C. Sheppard, *Solid Phase Peptide Synthesis: a Practical Approach*, IRL Press (Oxford, England (1989)).

Methods for preparing PEG-CNP variants provide a substantially homogenous mixture of polymer-protein conjugates. After purification, discrete PEG-CNP preparations are sufficiently pure for in vitro and in vivo testing of biological properties. The nature and extent of PEGylation can be determined using, e.g., PAGE and HPLC analysis. In certain embodiments, at least about 50%, 60%, 70%, 80%, 90%, 95% or 99% of CNP variant are mono-PEGylated at the N-terminus. To optimize the beneficial effects of PEGylation on the biological properties of a CNP, the polymer length, conformation (e.g., branched or linear), and/or functionalization (e.g., adding a negatively charged group) of a PEG moiety can be varied. PEGylated CNP variants are tested for NEP resistance, pharmacokinetics and bioactivity (e.g., the ability to bind to NPR-B and stimulate the generation of cGMP). PEGylated CNP variants that show improved NEP resistance and at least about 50% of the cGMP-stimulating activity of CNP-22 can be further tested, e.g., in vitro in a rat chondrosarcoma cell-based achondroplasia model and in vivo in a murine achondroplasia animal model.

E. METHODS OF USING CNP VARIANTS, PHARMACEUTICAL COMPOSITIONS OF CNP VARIANTS, AND ROUTES OF ADMINISTRATION

Methods of Using CNP Variants

As described in the Examples below, the experiments reported here provide evidence that the CNP variants disclosed herein are useful in the treatment of osteoarthritis. Accordingly, an embodiment of the invention comprises administering the CNP variant to a subject diagnosed with osteoarthritis. As a result the rate of cartilage degeneration in the subject can be decreased, and in some cases, may be reversed (i.e., cartilage can be induced to regenerate). Accordingly, the various symptoms and biomarkers associated with osteoarthritis can be improved. The Examples illustrate the utility of Gly-CNP-37 and Pro-Gly-CNP-37, though other variants disclosed herein can also be tested for efficacy and used in a similar fashion. Notably, Gly-CNP-37 and Pro-Gly-CNP-37, show indications of dramatically improved cartilage growth, mobility, and motor skills and significantly decreased cartilage degeneration.

Osteoarthritis can be diagnosed based on reporting of signs and symptoms from patients as described above, as well medical imaging to determine cartilage damage in a particular joint. Methods of imaging include radiography, magnetic resonance imaging (MRI), optical coherence tomography (OCT), and ultrasound (US) (Gold et al., Bone J. 51:278-88, 2012). Imaging can often detect joint narrowing, osteophytes and subchondral cysts in the joint area, thinning of the articular cartilage, degenerative subchondral marrow changes and bone fusion. In various embodiments, administration of CNP variants as contemplated herein improves one or more symptoms of osteoarthritis as described herein, including cartilage degeneration, cartilage growth, mobility of the patient, joint narrowing, osteophytes and subchondral cysts in the joint area, thinning of the articular cartilage, degenerative subchondral marrow changes and bone fusion, as well as others known in the field to those of skill in the art.

In certain instances, osteoarthritis has been divided into primary and secondary osteoarthritis (Stacy et al., Primary Osteoarthritis Imaging, 2012). Primary arthritis refers to an idiopathic phenomenon, often occurring in older individuals and in previously intact joints, with no apparent initiating factor. Secondary osteoarthritis can refer to degenerative disease of the synovial joints that results from some predisposing condition, usually trauma that has negatively affected the articular cartilage and/or subchondral bone of the affected joints. Secondary osteoarthritis can occurs in relatively young individuals. Treatment of both primary and secondary osteoarthritis is contemplated herein.

Severity of arthritis can be scored on the Western Ontario and McMaster Universities Osteoarthritis Index (WOMAC) (Kirkley et al., N Engl J Med 359:1097-1107, 2008), the Short Form-36 (SF-36) Physical Component Summary (Ware et al., Med Care 30:473-483, 1992) and Arthritis Self-Efficacy Scale (ASES) (Lorig et al., Arthritis Rheum 32:37-44, 1989). Radiographic severity can be assessed by the modified Kellgren-Lawrence classification (Kellgren et al., Ann Rheum Dis 1957; 16:494-502; Blackburn et al., J Rheumatol; 21:675-679, 1994).

Osteoarthritis can affect cartilage in the joints, including, but not limited to, the knee, shoulder, elbow, finger, hand, wrist, hips, ankle, neck, spine and/or lower back. Symptoms of osteoarthritis include joint pain, joint stiffness, joint swelling, decreased range of motion, and weakness or numbness of the arms and legs if there is arthritis in the back. There is currently an unmet need for novel efficacious treatments of osteoarthritis. By promoting matrix production and the growth and differentiation of chondrocytes, the CNP variants described herein are shown to be useful for countering the undesired effects of FGF-2 and increasing matrix synthesis in subjects suffering from arthritis, including osteoarthritis, thereby treating arthritis, including osteoarthritis.

In various embodiments, cartilage damage or growth is analyzed by chondrocyte death/loss, proteoglycan (PG) loss, and collagen loss or fibrillation. Cartilage damage and improvement after treatment can also be assessed by measuring the levels of at least one cartilage-specific biomarker as described herein. Mobility improvement can be monitored by any of the mobility and assessment scales described herein and known in the art.

Treatment of osteoarthritis often includes pain management using anti-inflammatories such as aspirin, NSAIDS, including naproxen or ibuprofen, acetaminophen, glucocorticoids, steroids and hyaluronic acid. Moderate to severe forms of arthritis can also be treated with surgery to replace the affected joint or remove some cartilage that may be causing the pain (Kirkey et al., N Engl J Med 359:1097-1107, 2008). A CNP variant herein can be administered with another treatment commonly used to treat osteoarthritis as described herein or known to a treating physician.

Pharmaceutical Compositions of CNP Variants

In additional embodiments, the disclosure contemplates use of pharmaceutical compositions comprising a CNP variant, and one or more pharmaceutically acceptable excipients, carriers and/or diluents. In certain embodiments, the compositions further comprise one or more other biologically active agents (e.g., inhibitors of proteases, receptor tyrosine kinases, and/or the clearance receptor NPR-C).

In some embodiments, the compositions comprise the desired CNP variant in at least about 70%, 75%, 80%, 85%, 90%, 95%, 96%, 97%, 98% or 99% purity. In certain embodiments, the compositions contain less than about 10%, 5%, 4%, 3%, 2%, 1% or 0.5% of macromolecular contaminants, such as other mammalian (e.g., human) proteins and other CNP variants.

Non-limiting examples of excipients, carriers and diluents include vehicles, liquids, buffers, isotonicity agents, additives, stabilizers, preservatives, solubilizers, surfactants, emulsifiers, wetting agents, adjuvants, and so on. The compositions can contain liquids (e.g., water, ethanol); diluents of various buffer content (e.g., Tris-HCl, phosphate, acetate buffers, citrate buffers), pH and ionic strength; detergents and solubilizing agents (e.g., Polysorbate 20, Polysorbate 80); anti-oxidants (e.g., methionine, ascorbic acid, sodium metabisulfite); preservatives (e.g., Thimerosol, benzyl alcohol, m-cresol); and bulking substances (e.g., lactose, mannitol, sucrose). The use of excipients, diluents and carriers in the formulation of pharmaceutical compositions is known in the art; see, e.g., Remington's Pharmaceutical Sciences, 18$^{th}$ Edition, pages 1435-1712, Mack Publishing Co. (Easton, Pennsylvania (1990)), which is incorporated herein by reference in its entirety.

For example, carriers include without limitation diluents, vehicles and adjuvants, as well as implant carriers, and inert, non-toxic solid or liquid fillers and encapsulating materials that do not react with the active ingredient(s). Non-limiting examples of carriers include phosphate buffered saline, physiological saline, water, and emulsions (e.g., oil/water emulsions). A carrier can be a solvent or dispersing medium containing, e.g., ethanol, a polyol (e.g., glycerol, propylene glycol, liquid polyethylene glycol, and the like), a vegetable oil, and mixtures thereof.

In some embodiments, the compositions are liquid formulations. In certain embodiments, the formulations comprise a CNP variant in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

In further embodiments, the compositions comprise a buffer solution or buffering agent to maintain the pH of a CNP-containing solution or suspension within a desired range. Non-limiting examples of buffer solutions include phosphate buffered saline, Tris buffered saline, and Hank's buffered saline. Buffering agents include without limitation sodium acetate, sodium phosphate, and sodium citrate. Mixtures of buffering agents can also be used. In certain embodiments, the buffering agent is acetic acid/acetate or citric acid/citrate. The amount of buffering agent suitable in a composition depends in part on the particular buffer used and the desired pH of the solution or suspension. For example, acetate is a more efficient pH buffer at pH 5 than pH 6, so less acetate may be used in a solution at pH 5 than at pH 6. In some embodiments, the buffering agent has a concentration of about 10 mM±5 mM. In certain embodiments, the pH of a composition is from about pH 3 to about pH 7.5, or from about pH 3.5 to about pH 7, or from about pH 3.5 to about pH 6.5, or from about pH 4 to about pH 6, or from about pH 4 to about pH 5, or is at about pH 5.0±1.0.

In other embodiments, the compositions contain an isotonicity-adjusting agent to render the solution or suspension isotonic and more compatible for injection. Non-limiting examples of isotonicity agents include NaCl, dextrose, glucose, glycerin, sorbitol, xylitol, and ethanol. In certain embodiments, the isotonicity agent is NaCl. In certain embodiments, NaCl is in a concentration of about 160±20 mM, or about 140 mM±20 mM, or about 120±20 mM, or about 100 mM±20 mM, or about 80 mM±20 mM, or about 60 mM±20 mM.

In various embodiments, the compositions comprise a preservative. Preservatives include, but are not limited to, m-cresol and benzyl alcohol. In certain embodiments, the preservative is in a concentration of about 0.4%±0.2%, or about 1%±0.5%, or about 1.5%±0.5%, or about 2.0%±0.5%.

In various embodiments, the compositions contain an anti-adsorbent (e.g., to mitigate adsorption of a CNP variant to glass or plastic). Anti-adsorbents include without limitation benzyl alcohol, Polysorbate 20, and Polysorbate 80. In certain embodiments, the anti-adsorbent is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%.

In various embodiments, the compositions comprise a stabilizer. Non-limiting examples of stabilizers include glycerin, glycerol, thioglycerol, methionine, and ascorbic acid and salts thereof. In some embodiments, when the stabilizer is thioglycerol or ascorbic acid or a salt thereof, the stabilizer is in a concentration from about 0.1% to about 1%. In other embodiments, when the stabilizer is methionine, the stabilizer is in a concentration from about 0.01% to about 0.5%, or from about 0.01% to about 0.2%. In still other embodiments, when the stabilizer is glycerin, the stabilizer is in a concentration from about 5% to about 100% (neat).

In various embodiments, the compositions contain an antioxidant. Exemplary anti-oxidants include without limitation methionine and ascorbic acid. In certain embodiments, the molar ratio of antioxidant to CNP variant is from about 0.1:1 to about 15:1, or from about 1:1 to about 15:1, or from about 0.5:1 to about 10:1, or from about 1:1 to about 10:1 or from about 3:1 to about 10:1.

Pharmaceutically acceptable salts can be used in the compositions, including without limitation mineral acid salts (e.g., hydrochloride, hydrobromide, phosphate, sulfate), salts of organic acids (e.g., acetate, propionate, malonate, benzoate, mesylate, tosylate), and salts of amines (e.g., isopropylamine, trimethylamine, dicyclohexylamine, diethanolamine). A thorough discussion of pharmaceutically acceptable salts is found in *Remington's Pharmaceutical Sciences*, 18$^{th}$ Edition, Mack Publishing Company, (Easton, Pennsylvania (1990)).

The pharmaceutical compositions can be administered in various forms, such as tablets, capsules, granules, powders, solutions, suspensions, emulsions, ointments, and transdermal patches. The dosage forms of the compositions can be tailored to the desired mode of administration of the compositions. For oral administration, the compositions can take the form of, e.g., a tablet or capsule (including softgel capsule), or can be, e.g., an aqueous or nonaqueous solution, suspension or syrup. Tablets and capsules for oral administration can include one or more commonly used excipients, diluents and carriers, such as mannitol, lactose, glucose, sucrose, starch, corn starch, sodium saccharin, talc, cellulose, magnesium carbonate, and lubricating agents (e.g., magnesium stearate, sodium stearyl fumarate). If desired, flavoring, coloring and/or sweetening agents can be added to the solid and liquid formulations. Other optional ingredients for oral formulations include without limitation preservatives, suspending agents, and thickening agents. Oral formulations can also have an enteric coating to protect the CNP variant from the acidic environment of the stomach. Methods of preparing solid and liquid dosage forms are known, or will be apparent, to those skilled in this art (see, e.g., Remington's Pharmaceutical Sciences, referenced above).

Formulations for parenteral administration can be prepared, e.g., as liquid solutions or suspensions, as solid forms suitable for solubilization or suspension in a liquid medium prior to injection, or as emulsions. For example, sterile injectable solutions and suspensions can be formulated according to techniques known in the art using suitable diluents, carriers, solvents (e.g., buffered aqueous solution, Ringer's solution, isotonic sodium chloride solution), dispersing agents, wetting agents, emulsifying agents, suspending agents, and the like. In addition, sterile fixed oils, fatty esters, polyols and/or other inactive ingredients can be used. As further examples, formulations for parenteral administration include aqueous sterile injectable solutions, which can contain antioxidants, buffers, bacteriostats, and solutes that render the formulation isotonic with the blood of the intended recipient; and aqueous and nonaqueous sterile suspensions, which can contain suspending agents and thickening agents.

Exemplary CNP formulations are described in U.S. Pat. Nos. 8,198,242 and 8,598,121. Use of CNP formulations having a pH in the range from about 4 to about 6 is contemplated.

In various embodiments, CNP variants can be formulated in pharmaceutical carriers for administration to subjects affected by osteoarthritis or osteoarthritis symptoms. In some embodiments, liquid formulations of CNP variants are formulated according to any combinations of the ingredients and their amounts or concentrations are described below:

| Ingredient Class | Ingredient | Concentration Range |
| --- | --- | --- |
| Active ingredient | CNP variant | 10 mg/mL ± 9.9 mg/mL |
| Buffering agent | Acetic acid/acetate | 10 mM ± 5 mM, or pH 5 ± 1 |
| Buffering agent | Citric acid/citrate | 10 mM ± 5 mM, or pH 5 ± 1 |
| Isotonicity-adjusting agent | NaCl | 140 mM ± 20 mM |
| Isotonicity-adjusting agent | Sucrose | 10% ± 5% |
| Preservative | m-Cresol | 0.4% ± 0.1% or 0.2% |
| Preservative/anti-adsorbent | Benzyl alcohol | 1.5% ± 0.5% |
| Stabilizer | Glycerin (glycerol) | 5%-100% (neat)[1] |
| Stabilizer | Methionine | 0.01%-0.2% |
| Stabilizer | Ascorbic acid/ascorbate salt | 0.1%-1% |
| Stabilizer | Thioglycerol | 0.1%-1% |
| Anti-adsorbent | Polysorbate 20 | 0.001%-0.5% |
| | Polysorbate 80 | 0.001%-0.5% |
| | Benzyl alcohol | 0.5%-1.5% |

[1]Glycerin is used to minimize or prevent water-driven hydrolysis, deamidation, isomerization or cleavage of CNP variants. For lyophilized formulations, 4-6% or 6-20% mannitol or sucrose can be substituted for NaCl.

Compositions comprising a CNP variant can also be lyophilized formulations. In certain embodiments, the lyophilized formulations comprise a buffer and bulking agent, and optionally an antioxidant. Exemplary buffers include without limitation acetate buffers and citrate buffers. Exemplary bulking agents include without limitation mannitol, sucrose, dextran, lactose, trehalose, and povidone (PVP K24). In certain embodiments, mannitol is in an amount from about 3% to about 10%, or from about 4% to about 8%, or from about 4% to about 6%. In certain embodiments, sucrose is in an amount from about 6% to about 20%, or from about 6% to about 15%, or from about 8% to about 12%.

In various embodiments, lyophilized formulations of CNP variants are prepared from formulations formulated according to any combinations of the ingredients and their amounts or concentrations described below:

| Ingredient Class | Ingredient | Concentration Range |
| --- | --- | --- |
| Active ingredient | CNP variant | 10 mg/mL ± 9.9 mg/mL |
| Buffering agent | Acetic acid/acetate | 10 mM ± 5 mM, or pH 5 ± 1 |
| Buffering agent | Citric acid/citrate | 10 mM ± 5 mM, or pH 5 ± 1 |
| Isotonicity-adjusting agent/bulking agent | Sorbitol | 5% ± 3% |
| Isotonicity-adjusting agent/bulking agent | Mannitol | 5% ± 3% |
| Isotonicity-adjusting agent/bulking agent | Sucrose | 10% ± 5% |
| Preservative | m-Cresol | 0.4% ± 0.2% |
| Preservative/anti-adsorbent | Benzyl alcohol | 1.5% ± 0.5% |
| Stabilizer | Glycerin (glycerol) | 5%-100% (neat)[1] |
| Stabilizer | Methionine | 0.01%-0.2% |
| Stabilizer | Ascorbic acid/ascorbate salt | 0.1%-1% |
| Stabilizer | Thioglycerol | 0.1%-1% |
| Anti-adsorbent | Polysorbate 20 | 0.001%-0.5% |
| | Polysorbate 80 | 0.001%-0.5% |
| | Benzyl alcohol | 0.5%-1.5% |

[1]Glycerin is used to minimize or prevent water-driven hydrolysis, deamidation, isomerization or cleavage of CNP variants.

In various embodiments, a formulation comprising a CNP variant has a pH of about 3-7, or about 3-6, or about 3.5-6.5, or about 4-6, or about 4-5, or about 4.5-5.5. In some embodiments, for pH 4-5.5 a suitable buffering agent is acetic acid/acetate (e.g., sodium acetate), and for pH 5.5-6 a suitable buffering agent is citric acid/citrate. Citric acid/citrate (e.g., sodium citrate) is also a suitable buffering agent in the range of pH 3-6 or pH 4-6. In certain embodiments, the buffering agent has a concentration in the formulation of about 2-50 mM, or about 2-40 mM, or about 2-30 mM, or about 5-30 mM, or about 2-20 mM, or about 5-20 mM, or about 5-15 mM.

To minimize or avoid deamidation of a CNP variant, the variant can be formulated in pharmaceutically acceptable organic cosolvents, such as glycerin, ethanol, and propylene glycol. Because deamidation occurs by hydrolysis, substitution of an organic cosolvent for water minimizes contact of the CNP variant with water. The concentration of one or more organic solvents in an organic-aqueous solvent system can be, e.g., from about 10% to about 99%, or about 100% if water is not used.

Also to minimize or avoid deamidation of a CNP variant, water can be removed from the formulation by lyophilization. In some embodiments, lyophilized formulations contain any combinations of the following components: buffer: sodium acetate and acetic acid, or sodium citrate and citric acid; isotonicity/bulking agent: mannitol (e.g., 3-10%, 2-8% or 4-6%); sucrose (e.g., 6-20%, 5-15% or 8-12%); antioxidants: methionine and/or ascorbic acid with molal ratio of each antioxidant to CNP variant from about 0.1:1 to about 1:1, or from about 0.5:1 to about 5:1, or from about 1:1 to about 15:1, or from about 1:1 to about 10:1, or from about 3:1 to about 10:1.

Deamidation can also be minimized or avoided by storing a CNP composition (e.g., a liquid formulation or a lyophilized formulation) at lower temperature, such as at about 5° C., 0° C., −10° C., −20° C., −30° C., −40° C., −50° C., −60° C., −70° C., −80° C., −90° C., or −100° C.

To minimize or avoid oxidation of oxidizable residues (e.g., methionine) in a CNP variant, the variant can be formulated with one or more antioxidants. Exemplary antioxidants include, but are not limited to, methionine, ascorbic acid, and thioglycerol. Oxidation of, e.g., methionine residues can also be minimized or prevented by purging oxygen from a liquid medium (if a liquid formulation) with nitrogen or argon, and/or by purging oxygen from a container or packaging with nitrogen or argon.

In some embodiments, to minimize or prevent adsorption (e.g., adsorption of a CNP variant to plastic or glass), Polysorbate 20, Polysorbate 80 or benzyl alcohol, or a combination thereof, is added to a CNP formulation. In certain embodiments, each of the anti-adsorbent(s) is in a concentration from about 0.001% to about 0.5%, or from about 0.01% to about 0.5%, or from about 0.1% to about 1%, or from about 0.5% to about 1%, or from about 0.5% to about 1.5%, or from about 0.5% to about 2%, or from about 1% to about 2%. Exemplary range(s) of anti-adsorbent(s) in the formulation include without limitation from about 0.001% to about 0.5% of Polysorbate 20, from about 0.001% to about 0.5% of Polysorbate 80, and/or from about 0.5% to about 1.5% of benzyl alcohol.

In certain embodiments, a liquid CNP formulation comprises, or a lyophilized CNP formulation is prepared from a formulation that comprises, (1) an acetic acid/acetate (e.g., sodium acetate) buffer having a concentration of about 30 mM±5 or 10 mM buffering agent and a pH of about 4±0.5 or 1, and (2) benzyl alcohol (e.g., as a preservative and/or anti-adsorbent) at a concentration of about 1%±0.5%, and optionally (3) sucrose at a concentration of about 10%±5%.

The disclosure also provides kits containing, e.g., bottles, vials, ampoules, tubes, cartridges and/or syringes that comprise a liquid (e.g., sterile injectable) formulation or a solid (e.g., lyophilized) formulation. The kits can also contain pharmaceutically acceptable vehicles or carriers (e.g., solvents, solutions and/or buffers) for reconstituting a solid (e.g., lyophilized) formulation into a solution or suspension for administration (e.g., by injection), including without limitation reconstituting a lyophilized formulation in a syringe for injection or for diluting concentrate to a lower concentration. Furthermore, extemporaneous injection solutions and suspensions can be prepared from, e.g., sterile powder, granules, or tablets comprising a CNP-containing composition. The kits can also include dispensing devices, such as aerosol or injection dispensing devices, pen injectors, autoinjectors, needleless injectors, syringes, and/or needles.

As a non-limiting example, a kit can include syringes having a single chamber or dual chambers. For single-chamber syringes, the single chamber can contain a liquid CNP formulation ready for injection, or a solid (e.g., lyophilized) CNP formulation or a liquid formulation of a CNP variant in a relatively small amount of a suitable solvent system (e.g., glycerin) that can be reconstituted into a solution or suspension for injection. For dual-chamber syringes, one chamber can contain a pharmaceutically acceptable vehicle or carrier (e.g., solvent system, solution or buffer), and the other chamber can contain a solid (e.g., lyophilized) CNP formulation or a liquid formulation of a CNP variant in a relatively small amount of a suitable solvent system (e.g., glycerin) which can be reconstituted into a solution or suspension, using the vehicle or carrier from the first chamber, for injection.

As a further example, a kit can include one or more pen injector or autoinjector devices, and dual-chamber cartridges. One chamber of a cartridge can contain a pharmaceutically acceptable vehicle or carrier (e.g., solvent system, solution or buffer), and the other chamber can contain a solid (e.g., lyophilized) CNP formulation or a liquid formulation of a CNP variant in a relatively small amount of a suitable solvent system (e.g., glycerin) which can be reconstituted into a solution or suspension, using the vehicle or carrier from the first chamber, for injection. A cartridge can comprise an amount of the CNP variant that is sufficient for dosing over a desired time period (e.g., 1 day, 2 days, 3 days, 1 week, 2 weeks, 3 weeks, 4 weeks, etc.). The pen injector or autoinjector can be adjusted to administer a desired amount of the CNP formulation from a cartridge.

In addition, pharmaceutical compositions comprising a CNP variant can be formulated as a slow release, controlled release or sustained release system for maintaining a relatively constant level of dosage over a desired time period, such as 1 week, 2 weeks, 3 weeks, 1 month, 2 months, or 3 months. Slow release, controlled release and sustained release formulations can be prepared using, e.g., biodegradable polymeric systems {which can comprise, e.g., hydrophilic polymers [e.g., polylactide, polyglycolide, poly(lactide-glycolide)]}, and can take the form of, e.g., microparticles, microspheres or liposomes, as is known in the art.

Dosages and Frequency of Dosing

As used herein, the term "therapeutically effective amount" of an active agent (e.g., a CNP variant) refers to an amount that provides therapeutic benefit to a patient. The amount may vary from one individual to another and may depend upon a number of factors, including the overall physical condition of the patient. A therapeutically effective amount of a CNP variant can be readily ascertained by one skilled in the art, using publicly available materials and procedures. For example, the amount of a CNP variant used for therapy should give an acceptable rate of growth based on growth charts for children ages 0-17 years with achondroplasia (214 females and 189 males), which list height for age, head circumference, and segmental growth (Horton WA et al., Standard growth curves for achondroplasia, J. Pediatr., 93: 435-8 (1978)). CDC charts can be used to assess weight for age and weight for height or BMI for age. Secondary outcomes with courses that are more chronic in nature can also be measured.

The dosing frequency for a particular individual may vary depending upon various factors, including the disorder being treated and the condition and response of the individual to the therapy. In certain embodiments, a pharmaceutical composition containing a CNP variant is administered to a subject about one time per day, one time per two days, one time per three days, or one time per week, twice per week, three times per week, once every two weeks, or monthly.

The CNP variants contemplated for use herein can be administered to patients at therapeutically effective doses to treat, ameliorate or prevent osteoarthritis and other conditions having an osteoarthritis-associated symptom. The safety and therapeutic efficacy of the CNP variants can be determined by standard pharmacological procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Active agents exhibiting a large therapeutic index are normally preferred.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The therapeutically effective dose can be determined from cell culture assays and animal studies.

In certain embodiments, the CNP variants described herein are administered at a dose in the range from about 5 or 10 nmol/kg to about 300 nmol/kg, or from about 20 nmol/kg to about 200 nmol/kg. In some embodiments, the CNP variants are administered at a dose of about 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg or other dose deemed appropriate by the treating physician. In other embodiments, the CNP variants are administered at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 µg/kg, or about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. The doses of CNP variants described herein can be administered according to the dosing frequency/frequency of administration described herein, including without limitation daily, 2 or 3 times per week, weekly, every 2 weeks, every 3 weeks, monthly, etc.

The frequency of dosing/administration of a CNP variant for a particular subject may vary depending upon various factors, including the disorder being treated and the condition and response of the subject to the therapy. The CNP variant can be administered in a single dose or in multiple doses per dosing. In certain embodiments, the CNP variant is administered, in a single dose or in multiple doses, daily, every other day, every 3 days, 2 times per week, 3 times per week, weekly, bi-weekly, every 3 weeks, monthly, every 6 weeks, every 2 months, every 3 months, or as deemed appropriate by the treating physician.

In some embodiments, a CNP variant is administered so as to allow for periods of growth (e.g., chondrogenesis), followed by a recovery period. For example, the CNP variant may be administered intravenously, subcutaneously, intraarticularly or by another mode daily or multiple times per week for a period of time, followed by a period of no treatment, then the cycle is repeated. In some embodiments, the initial period of treatment (e.g., administration of the CNP variant daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the CNP variant is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

Modes of Administration

The CNP variants, or pharmaceutical compositions comprising them, can be administered to subjects in various ways such as, e.g., by injection subcutaneously, intraarticularly, intravenously, intra-arterially, intraperitoneally, intramuscularly, intradermally, or intrathecally. In one embodiment, the CNP variants are administered by a single subcutaneous, intraarticular, intravenous, intra-arterial, intraperitoneal, intramuscular, intradermal or intrathecal injection once a day, one every other day, once every three days, or once a week.

The CNP variants can also be administered by direct injection at or near the site of disease. Further, the CNP variants can be administered by implantation of a depot at the target site of action (e.g., an abnormal or degenerated joint or cartilage area). Alternatively, the CNP variants can be administered sublingually under the tongue (e.g., sublingual tablet) or by inhalation into the lungs (e.g., inhaler or aerosol spray), by delivery into the nasal cavity (e.g., intranasal spray), by delivery into the eye (e.g., eye drop), or by transdermal delivery (e.g., by means of a patch on the skin). The CNP variants may also be administered orally in the form of microspheres, microcapsules, liposomes (uncharged or charged (e.g., cationic)), polymeric microparticles (e.g., polyamides, polylactide, polyglycolide, poly (lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the CNP variant or pharmaceutical composition over a pre-determined period. The osmotic pump or mini-pump can be implanted subcutaneously, or near the target site (e.g., the long bones of limbs, the epiphyses, etc.).

It will be apparent to one skilled in the art that the CNP variants or compositions thereof can also be administered by other modes. Determination of the most effective mode of administration of the CNP variants or compositions thereof is within the skill of the skilled artisan.

The CNP variants can be administered as pharmaceutical formulations suitable for, e.g., oral (including buccal and sub-lingual), rectal, nasal, topical, pulmonary, vaginal or parenteral (including intramuscular, intraarterial, intrathecal, subcutaneous and intravenous) administration, or in a form suitable for administration by inhalation or insufflation. Depending on the intended mode of administration, the pharmaceutical formulations can be in the form of solid, semi-solid or liquid dosage forms, such as tablets, suppositories, pills, capsules, powders, liquids, suspensions, emulsions, creams, ointments, lotions, and the like. The formulations can be provided in unit dosage form suitable for single administration of a precise dosage. The formulations comprise an effective amount of a CNP variant, and one or more pharmaceutically acceptable excipients, carriers and/ or diluents, and optionally one or more other biologically active agents.

Combination Therapy

In one embodiment, a CNP variant can be used in combination with one or more other active agents useful for treating, ameliorating or preventing osteoarthritis. The other active agent(s) can enhance the effects of the CNP variant and/or exert other pharmacological effects in addition to those of the CNP variant. Non-limiting examples of active agents that can be used in combination with the CNP variants described herein are other natriuretic peptides (e.g., BNP) and inhibitors (e.g., antagonists) of peptidases and proteases (e.g., NEP and furin), NPR-C and tyrosine kinases (e.g., FGFR-3). Examples of NEP inhibitors include, without limitation, thiorphan and candoxatril. Co-use of an NPR-C inhibitor can also prolong the half-life of the CNP variant via inhibition of the variant's clearance by NPR-C.

The CNP variant can be administered in combination with anti-inflammatories or pain relievers such as an anti-inflammatory agent, an NSAID, a corticosteroid, and hyaluronic acid.

To achieve the appropriate therapeutic outcome in the combination therapies, one would generally administer to the subject the CNP composition and other therapeutic(s) in a combined amount effective to produce the desired therapeutic outcome (e.g., restored bone growth). This process may involve administering the CNP composition and other therapeutic agent(s) at the same time. Simultaneous administration can be achieved by administering a single composition or pharmacological protein formulation that includes both the CNP variant and other therapeutic agent(s). Alternatively, the other therapeutic agent(s) can be taken separately at about the same time as a pharmacological formulation (e.g., tablet, injection or drink) of the CNP variant. The CNP variant can also be formulated into a foodstuff such as brownies, pancakes, or cake, suitable for ingestion.

In other alternatives, administration of the CNP variant can precede or follow administration of the other therapeutic agent(s) by intervals ranging from minutes to hours. In embodiments where the other therapeutic agent(s) and the CNP composition are administered separately, one would generally ensure that the CNP variant and the other therapeutic agent(s) are administered within an appropriate time of one another so that both the CNP variant and the other therapeutic agent(s) can exert, synergistically or additively, a beneficial effect on the patient. For example, one can administer the CNP composition within about 0.5-6 hours (before or after) of the other therapeutic agent(s). In one embodiment, the CNP composition is administered within about 1 hour (before or after) of the other therapeutic agent(s).

Identifying and Monitoring Patient Populations

Protocols can be established to identify subjects suitable for CNP therapy. For example, suitable patients can be identified using joint aspiration/synovial fluid analysis, X-ray, and/or MRI techniques. Protocols can also be established to determine whether a given patient is responsive to CNP therapy. For example, for treatment of osteoarthritis, indicators of growth can be measured, such as cartilage growth measurements and mobility assessments.

One CNP signaling marker is cGMP (guanosine 3',5' cyclic monophosphate). The level of this intracellular signaling molecule increases after CNP binds to and activates its cognate receptor NPR-B. Elevated levels of cGMP can be measured from cell culture extracts (in vitro) after CNP exposure, conditioned media from bone ex-plant studies (ex vivo) after CNP exposure, and in the plasma (in vivo) within minutes of CNP administration subcutaneously, intravenously, or via other routes of administration known in the art.

Cartilage-specific analytes (or cartilage-associated markers) can also be measured to assess CNP efficacy. For example, fragments of cleaved collagen type II are a cartilage-specific marker for cartilage turnover. Type II collagen is the major organic constituent of cartilage and fragments of type II collagen (cleaved collagen) are released into circulation, and subsequently secreted into the urine, following cartilage turnover. Cartilage turnover precedes new bone formation.

Other potential biomarkers for cartilage formation and growth or degeneration include aggrecan chondroitin sulfate (cartilage-specific marker for cartilage turnover), propeptides of type II collagen (cartilage-specific marker for cartilage formation, proliferating cell nuclear antigen (PCNA), aggrecan chondroitin sulfate, syndecan-3 and annexin VI. Cartilage-associated biomarkers can be measured, e.g., in serum from efficacy/pharmacodynamic in vivo studies and from the conditioned media of ex vivo studies, using commercially available kits.

In one embodiment, the level of at least one cartilage-associated biomarker is assayed or measured in a subject that has been administered a CNP variant in order to monitor the effects of the CNP variant on bone and cartilage formation and growth in vivo. For example, an increase in the level of at least one bone- or cartilage-associated biomarker may indicate that administration of a CNP variant has a positive effect on bone growth and is a useful treatment for skeletal dysplasias and other bone- or cartilage-related diseases or disorders associated with decreased CNP activity. Exemplary cartilage-associated biomarkers include, but are not limited to, CNP (e.g., endogenous levels of CNP), cGMP, propeptides of collagen type II and fragments thereof, collagen type II and fragments thereof, propeptides of collagen type I and fragments thereof, collagen type I and fragments thereof, proliferating cell nuclear antigen (PCNA), aggrecan chondroitin sulfate, syndecan-3 and annexin VI.

In various embodiments, biomarkers are measured by obtaining a biological sample from a subject who will be administered, is being administered or has been administered a CNP variant. Biomarkers can be measured using techniques known in the art, including, but not limited to, Western Blot, enzyme linked immunosorbent assay (ELISA), and enzymatic activity assay. The biological sample can be blood, serum, urine, or other biological fluids.

Additional aspects and details of the disclosure will be apparent from the following examples, which are intended to be illustrative rather than limiting.

F. EXAMPLES

Example 1

Rat Osteoarthritis Model

A unilateral medial meniscal tear in 275-300 gram rats will result in rapidly progressive cartilage degeneration—characterized by chondrocyte and proteoglycan loss, fibrillation, osteophyte formation, and chondrocyte cloning. This model is performed by transection of the medial collateral ligament just below its attachment to the meniscus so that when the joint space opens, the meniscus is reflected toward the femur. The meniscus is cut at its narrowest point (away from the ossicles) taking care not to damage the tibial surface and making sure that the resulting transection produces separate, freely movable anterior and posterior meniscus halves.

Progressive cartilage degenerative changes occur and by 3-6 weeks post-surgery, tibial cartilage degeneration may be focally severe on the outer ⅓ of the tibia with degenerative changes of lesser severity in the middle and inner ⅓. Osteophytes are ultimately quite large (medial tibia) and progressively increase in size. The model is progressive and results in total cartilage loss (to eburnated bone) in 12 months in virtually all rats, with lesions that are reasonably consistent. Rats resume weight bearing immediately post-surgery and gait analysis suggests little if any change in load bearing of the operated knee. Due to the rapid progression of cartilage degeneration, protective effects are not always apparent in the outer ⅓ of the tibial cartilage, although zonal analysis may reveal effects of treatment in the middle and inner ⅓. Substantial subchondral and epiphyseal bone changes occur in the medial tibia subjacent to the areas of greatest lesion severity. These range in magnitude and type from increased basophilia of the calcified cartilage layer with small fractures into subchondral bone to overt collapse of articular cartilage into areas of bone resorption in the epiphysis with surrounding sclerosis of bone. Therefore, this model offers the opportunity to evaluate not only chondroprotective effects of agents but also bone preserving activities. The model is of relatively short duration and animals are very consistent in their response to the surgery.

This rat model was used to determine the effect of CNP variants on slowing or repairing cartilage damage in osteoarthritis, where the CNP is delivered in response to joint injury or trauma. In this model a tear was introduced into the meniscus to provoke joint injury which results in cartilage degeneration and osteoarthritis (Janusz et al., Osteoarthritis Cartilage, 10:785-791, 2002). Male Lewis rats received a unilateral medial meniscectomy on Day 0; administration of control vehicle or the CNP variant Gly-CNP-37 began on Day 7; and the animals were euthanized on Day 29 for histopathological analysis of the affected joints. Gly-CNP-37 (provided at 0.71 or 2.2 mg/mL in control vehicle) or control vehicle alone was administered through intra-articular (IA) injections three times per week (M, W, F) for 3 weeks. Therapeutic efficacy was evaluated by gait analysis and histopathological examination of chondrocyte death/cartilage degeneration in the knee.

Surgery

In particular, surgery animals were anesthetized with isoflurane and the right knee and lower leg area were prepared for surgery. For the meniscal tear, a skin incision was made over the medial aspect of the knee and the medial collateral ligament was transected after being exposed by blunt dissection. The medial meniscus was cut through the full thickness to simulate a complete tear and the wound closed. Ninety minutes (90 min) post-surgery, animals were treated with a dose of Acetaminophen (100 mg/kg, PO) in 1% CMC (2 mL/kg, 50 mg/mL). A follow-on dose was given 24 hours post-surgery (as needed).

Histopathology

For histopathological analysis the operated joints were harvested from the euthanized rats. Following 4-6 days in 5% formic acid decalcifier, the operated joints are cut into two approximately equal halves in the frontal plane and embedded in paraffin. Sections were cut from each operated right knee at approximately 160 µm steps and stained with toluidine blue. To evaluate the effects of Gly-CNP-37 on osteoarthritis development the following parameters were measured or scored for each of the treated joints and compared to the vehicle treated control joints: cartilage degeneration, depth of lesion, width of lesion, damage to the calcified cartilage layer and subchondral bone, medial tibial subchondral/epiphyseal trabecular bone thickening/sclerosis, osteophyte thickness, collagen damage, growth plate thickness, and medial collateral ligament/synovial repair.

For some parameters (where noted), regional differences across the tibial plateau are taken into consideration by dividing each section into three zones (1-outside, 2-middle, 3-inside).

Data was analyzed using a Student's t-test or Mann-Whitney U test (non-parametric). If appropriate, data can also be further analyzed across all groups, using a one-way analysis of variance (1-way ANOVA) or Kruskal-Wallis test (non-parametric), along with the appropriate multiple comparison post-test. Statistical tests make certain assumptions regarding the data's normality and homogeneity of variance, and further analysis may be required if testing resulted in violations of these assumptions. Significance for all tests was set at $p<0.05$.

Medial Tibial and Femoral General Cartilage Degeneration

General cartilage degeneration was determined for each joint by an evaluation of chondrocyte death/loss, proteoglycan (PG) loss, and collagen loss or fibrillation, and was scored as provided in Table 1.

TABLE 1

Histopathologic Scoring Criteria for Cartilage Degeneration

| SCORE | SCORING CRITERIA |
|---|---|
| 0 | No degeneration. |
| 1 | Minimal degeneration, within the zone 5-10% of the matrix appears non-viable as a result of significant chondrocyte loss (greater than 50% of normal cell density). PG loss is usually present in these areas of cell loss and collagen matrix loss may be present. |
| 2 | Mild degeneration, within the zone 11-25% of the matrix appears non-viable as a result of significant chondrocyte loss (greater than 50% of normal cell density). PG loss is usually present in these areas of cell loss and collagen matrix loss may be present. |
| 3 | Moderate degeneration, within the zone 26-50% of the matrix appears non-viable as a result of significant chondrocyte loss (greater than 50% of normal cell density). PG loss is usually present in these areas of cell loss and collagen matrix loss may be present. |
| 4 | Marked degeneration, within the zone 51-75% of the matrix appears non-viable as a result of significant chondrocyte loss (greater than 50% of normal cell density). PG loss is usually present in these areas of cell loss and collagen matrix loss may be present. |
| 5 | Severe degeneration, within the zone 76-100% of the matrix appears non-viable as a result of significant chondrocyte loss (greater than 50% of normal cell density). PG loss is usually present in these areas of cell loss and collagen matrix loss may be present. |

A three-zone sum for cartilage degeneration was calculated in addition to expressing the data for each zone. Rats treated with Gly-CNP-37 at low (35.5 µg/dose) or high dose (110 µg/dose) showed significant reduction in cartilage degeneration in the tibia (FIG. 1) as compared to the untreated control rats.

Medial Tibial Lesion Depth and Width

Figure 2:
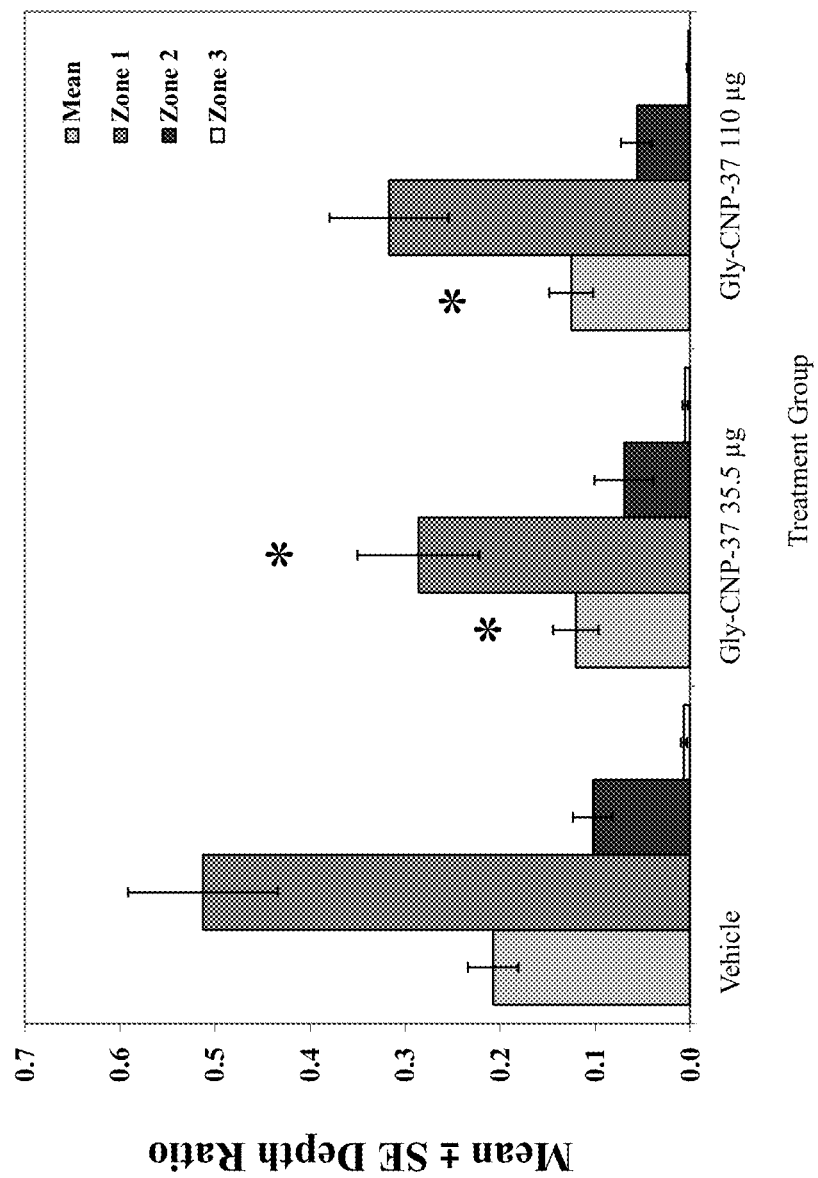
FIG. 2 shows that the depth ratio was improved in the Gly-CNP-37 treated groups. *$p \leq 0.05$ ANOVA to vehicle.
Figure 3:
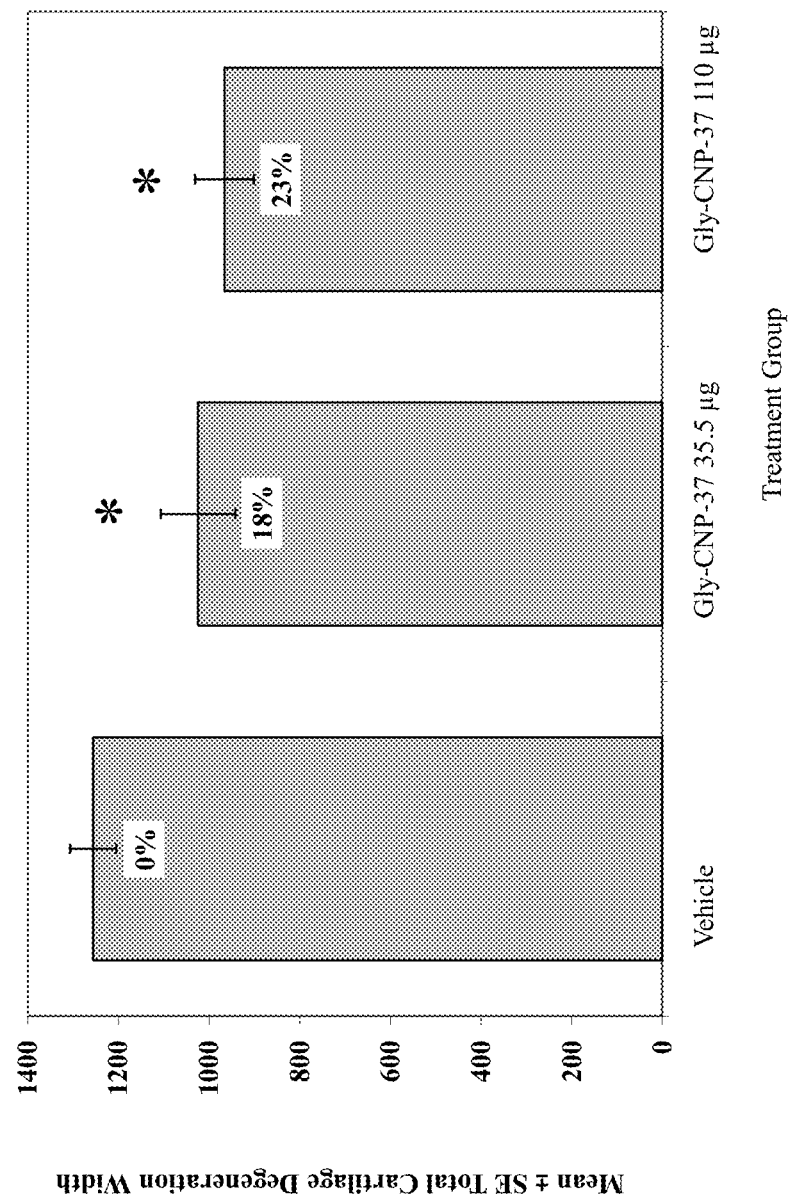
FIG. 3 is a graph showing that the width of the cartilage affected by any degeneration was improved in the Gly-CNP-37 treated groups. *$p \leq 0.05$ ANOVA to vehicle.

The depth of any type of lesion (lesion depth) and the depth to tidemark (total depth) were measured by ocular micrometer in the area of greatest lesion severity in each of the three zones of the tibial plateau. From these measurements, a depth ratio was calculated for each joint by dividing the lesion depth by the total depth. The total depth to tidemark can serve as an average measure of cartilage thickness in each of the three zones for comparison of anabolics when measures are taken at the midpoint of the zone. FIG. 2 shows that the depth ratio was improved in the Gly-CNP-37 treated groups as compared to the vehicle treated controls. The width of the cartilage affected by any degeneration (cell loss, proteoglycan loss, or collagen damage) as measured by ocular micrometer was also improved in the CNP treated groups (FIG. 3). This measurement extends from the origination of the osteophyte with adjacent cartilage degeneration (outside ⅓) across the surface to the point where tangential layer and underlying cartilage appear histologically normal.

Figure 4:
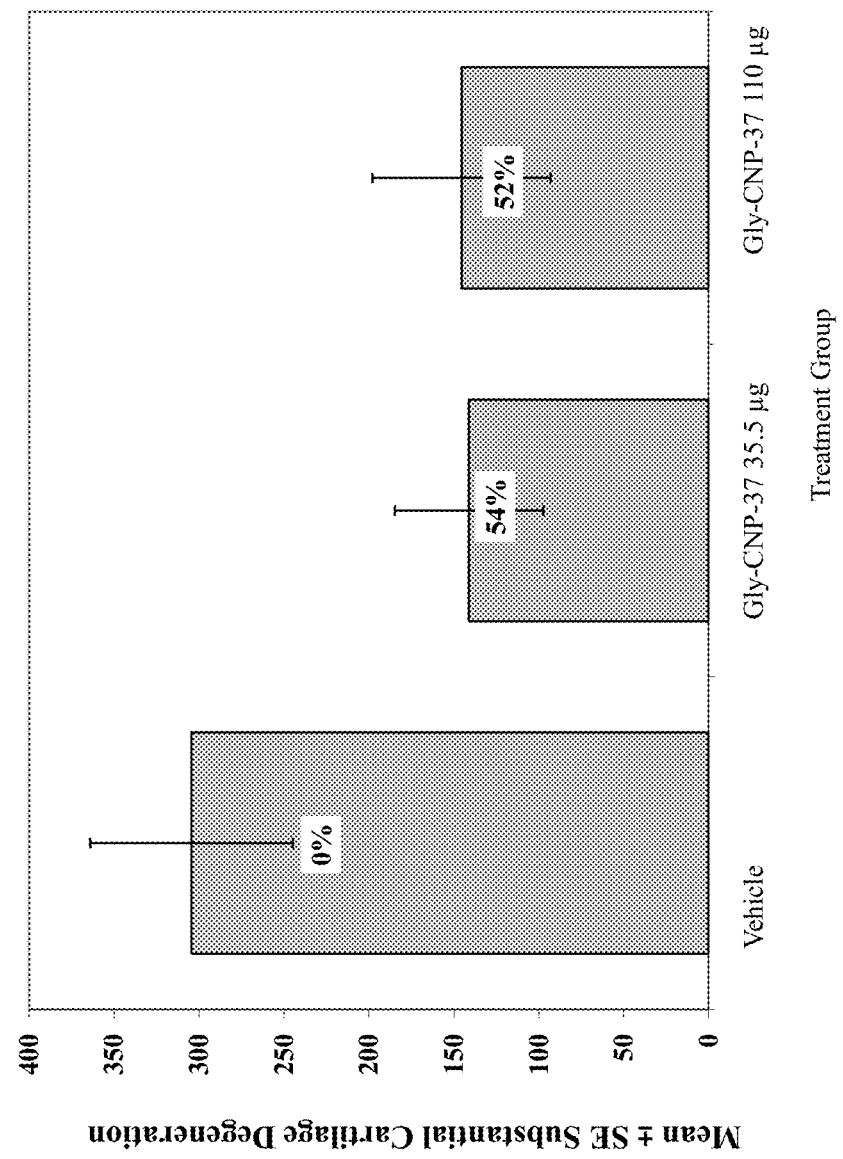
FIG. 4 illustrates that Gly-CNP-37 treated animals exhibited greater than 50% improvement in substantial tibial cartilage degeneration.

Substantial cartilage degeneration is defined as chondrocyte and proteoglycan loss extending through greater than 50% of the cartilage thickness as measured by ocular micrometer. Typically, in this model collagen damage is mild (defined as ~25% depth) or greater, however chondrocyte and proteoglycan loss is substantial and extends to at least 50% or greater of the cartilage depth, indicative of regions in which permanent structural changes have occurred. The width of the operated joints showing substantial cartilage degeneration was measured in Gly-CNP-37 treated animals and vehicle treated controls to assess the ability of CNP variants to reduce substantial degeneration. As shown in FIG. 4, vehicle treated controls showed little to no reduction in degeneration width while Gly-CNP-37 treated animals showed greater than 50% improvement in substantial tibial cartilage degeneration.

Calcified Cartilage Layer and Subcondral Bone Damage

Damage to the calcified cartilage layer and subchondral bone was scored using the criteria in Table 2.

TABLE 2

Histopathological Scoring Criteria for Cartilage Layer and Subchondral Bone Damage.

| SCORE | SCORING CRITERIA |
|---|---|
| 0 | No changes. |
| 1 | Increased basophilia at tidemark, no fragmentation of tidemark, no marrow changes or if present minimal and focal, affects less than 10% of linear width of tidemark. |
| 2 | Increased basophilia at tidemark, minimal to mild focal fragmentation of calcified cartilage of tidemark affects approximately 1-10% of the linear width of the tidemark, mesenchymal change in marrow involves up to ¼ of total area but generally is restricted to subchondral region under lesion, no collapse of cartilage into epiphyseal bone. |
| 3 | Increased basophilia at tidemark, mild to moderate focal or multifocal fragmentation or loss of calcified cartilage/subchondral bone (multifocal) affects 11-25% of linear width of tidemark, mesenchymal change in marrow is up to ¾ of total area, areas of marrow chondrogenesis may be evident with focal collapse of articular cartilage into epiphyseal bone less than 200 μm deep. |
| 4 | Increased basophilia at tidemark, marked to severe fragmentation and or loss of calcified cartilage/subchondral bone affects 26-50% of linear width of tidemark, marrow mesenchymal change involves up to ¾ of area and articular cartilage may have collapsed into the epiphysis to a depth of 200-350 μm or less from tidemark. |
| 5 | Increased basophilia at tidemark, marked to severe fragmentation and or loss of calcified cartilage/subchondral bone affects greater than 50% of the width of the tidemark, marrow mesenchymal change involves up to ¾ of area and articular cartilage may have collapsed into the epiphysis to a depth of greater than 350 μm from tidemark. |

Treatment with Gly-CNP-37 at the higher dose (110 μg/dose) reduced damage to the calcified cartilage and subchondral bone from a score of approximately 2.4 in vehicle treated animals to 1.3 in Gly-CNP-37 treated animals. Treatment with Gly-CNP-37 at the lower dose (35.5 μg/dose) also reduced damage to the calcified cartilage and subchondral bone, but to a lesser extent than the higher dose.

Tibial Bone Thickening, Osteophyte Thickness, and Total Joint Score

Medial tibial subchondral/epiphyseal trabecular bone thickening/sclerosis was scored based on the criteria shown in Table 3 using a comparison to the lateral tibia and/or normal left medial tibias.

TABLE 3

Histopathological Scoring of Bone Thickening

| SCORE | SCORING CRITERIA |
|---|---|
| 0 | Normal, no observable difference in subchondral or epiphyseal trabecular bone thickness in medial vs. lateral. |
| 1 | 5-10% increase in subchondral or epiphyseal trabecular bone thickness in medial vs. lateral. |
| 2 | 11-25% increase in subchondral or epiphyseal trabecular bone thickness in medial vs. lateral. |

TABLE 3-continued

Histopathological Scoring of Bone Thickening

| SCORE | SCORING CRITERIA |
|---|---|
| 3 | 26-50% increase in subchondral or epiphyseal trabecular bone thickness in medial vs. lateral, obvious reduction in marrow spaces in outer ¾ of medial tibia. |
| 4 | 51-75% increase in subchondral or epiphyseal trabecular bone thickness in medial vs. lateral, generally has very little marrow space in outer ¾ of medial tibia, marrow spaces remain adjacent to cruciates. |
| 5 | 76-100% increase in subchondral or epiphyseal trabecular bone thickness in medial vs. lateral, generally has very little marrow space remains in medial tibia. |

Treatment with Gly-CNP-37 at both doses showed an observable decrease in medial tibial subchondral/epiphyseal trabecular bone thickening/sclerosis as compared to the vehicle treated controls, although the results did not exhibit significance as set by the current study.

Osteophyte thickness (tidemark to furthest point extending toward synovium) was measured with an ocular micrometer. Scores were assigned to the largest osteophyte in each section (typically found on the tibia) according to the criteria in Table 4.

TABLE 4

Osteophyte Thickness Scoring

| SCORE | SCORING CRITERIA |
|---|---|
| 0 | Less than 200 µm. |
| 1 | Small 200-299 µm. |
| 2 | Medium 300-399 µm. |
| 3 | Large 400-499 µm. |
| 4 | Very large 500-599 µm. |
| 5 | Very large ≥600 µm. |

Treatment with Gly-CNP-37 at the high dose (110 µg/dose) reduced tibial osteophyte measurement by approximately 24% (p<0.05) and reduced tibial osteophyte score by approximately 34% (p<0.05).

Figure 5:
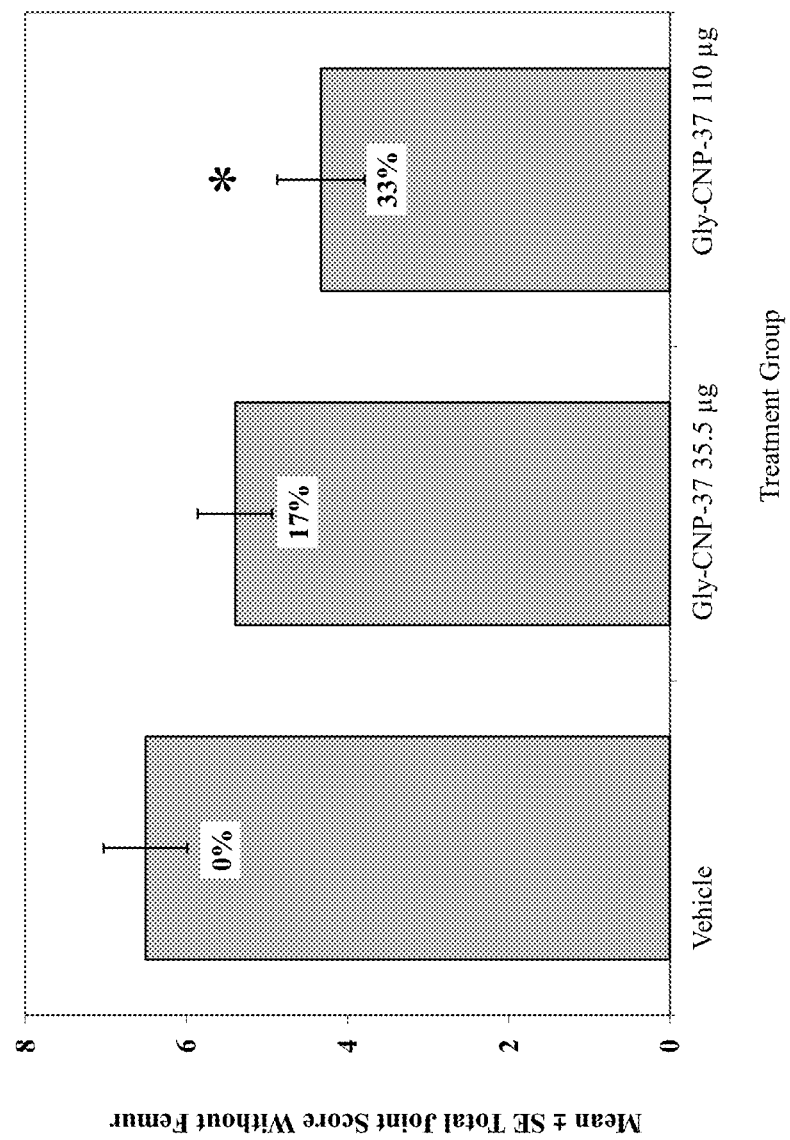
FIG. 5 shows that Gly-CNP-37 at 110 µg significantly reduced total joint score (w/o inclusion of femur). *$p \leq 0.05$ ANOVA to vehicle.
Figure 6:
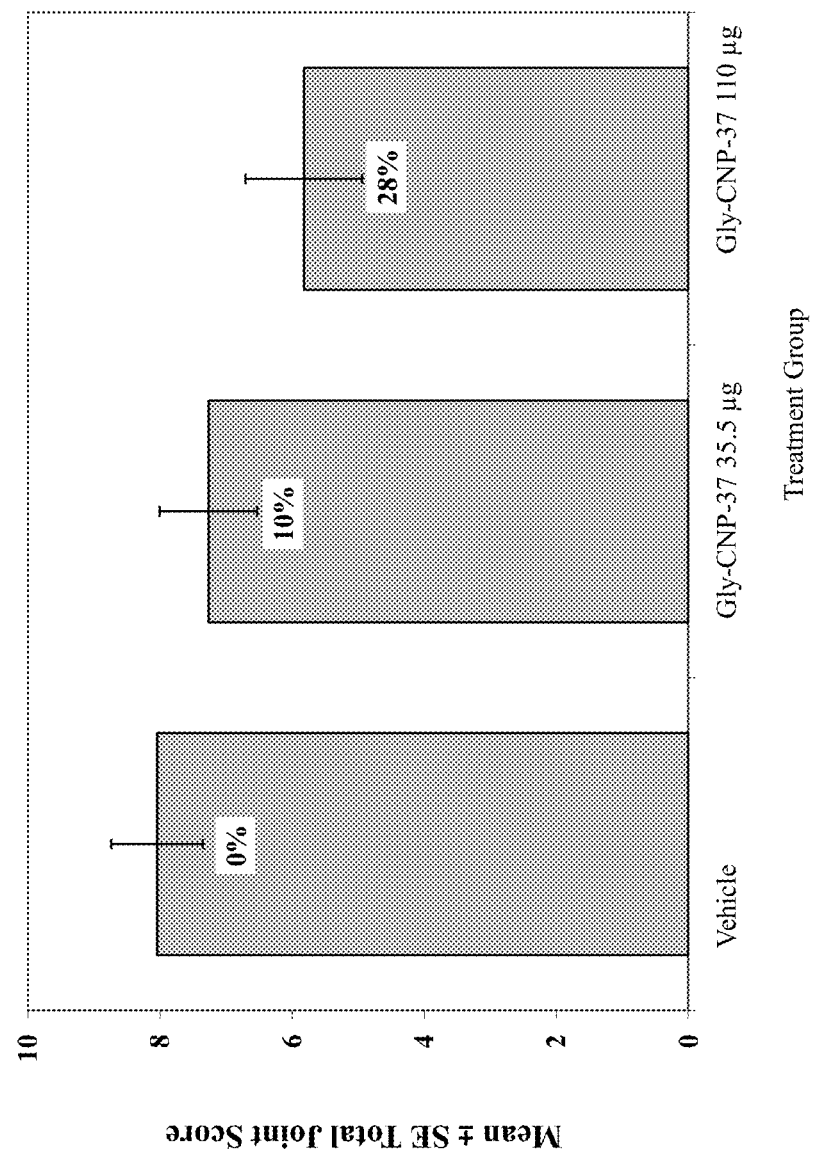
FIG. 6 is a graph representing total joint score for Gly-CNP-37 treated animals when the femur score is included in the calculation.

"Total Joint Scores" were calculated for each joint by summing each of the three-zone scores of the tibial and femoral cartilage degeneration and the osteophyte score (Total Joint Score with Femur), and by summing each of the three-zone scores of only the tibial cartilage degeneration and the osteophyte score (Total Joint Score without Femur). As shown in FIG. 5, Gly-CNP-37 at 110 µg/dose significantly reduced the Total Joint Score without Femur. Treatment with Gly-CNP-37 at the lower 35.5 µg/dose also exhibited and improved Total Joint Score without Femur, albeit to a lesser extent as compared to the higher dose. When the score for the femur is included (FIG. 6), the results show that Gly-CNP-37 decreases total joint score at both doses, but not to a significant level.

Collagen Damage, Growth Plate Thickness, and Ligament/Synovial Repair

Collagen damage across the medial tibial plateau (most severely affected section of the two halves) was assessed by measuring the total width of the following using an ocular micrometer and the following parameters: any damage (fibrillation ranging from superficial to full thickness loss); severe damage (total or near total loss of collagen to tidemark, >90% thickness); marked damage (extends through 61-90% of the cartilage thickness); moderate damage (extends thru 31-60% of the cartilage thickness); mild damage (extends through 11-30% of the cartilage thickness); and minimal damage (very superficial, affecting upper 10% only).

Treatment with Gly-CNP-37 at both the lower and higher doses resulted in fewer areas with severe, marked and moderate degeneration as compared to the untreated controls.

Figure 7:
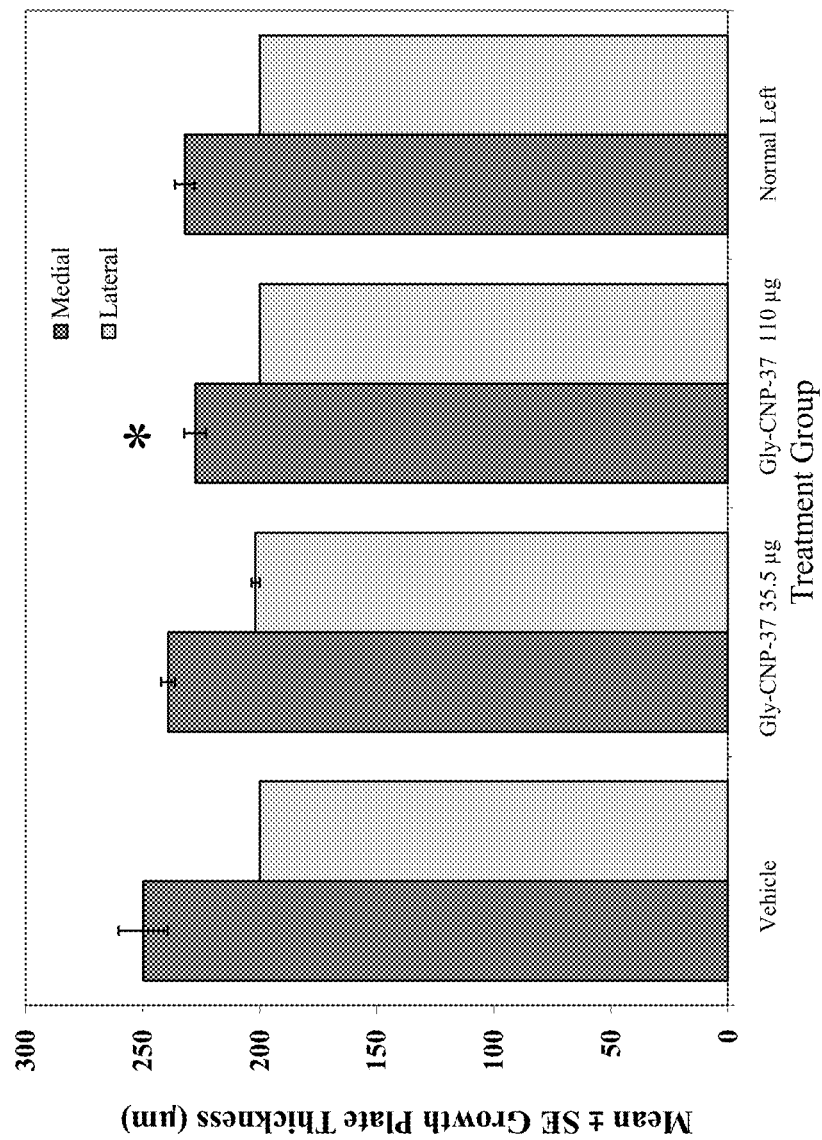
FIG. 7 is a graph illustrating the medial and lateral growth plate thickness in Gly-CNP-37 treated and untreated control animals. *$p \leq 0.05$ ANOVA to vehicle.
Figure 8:
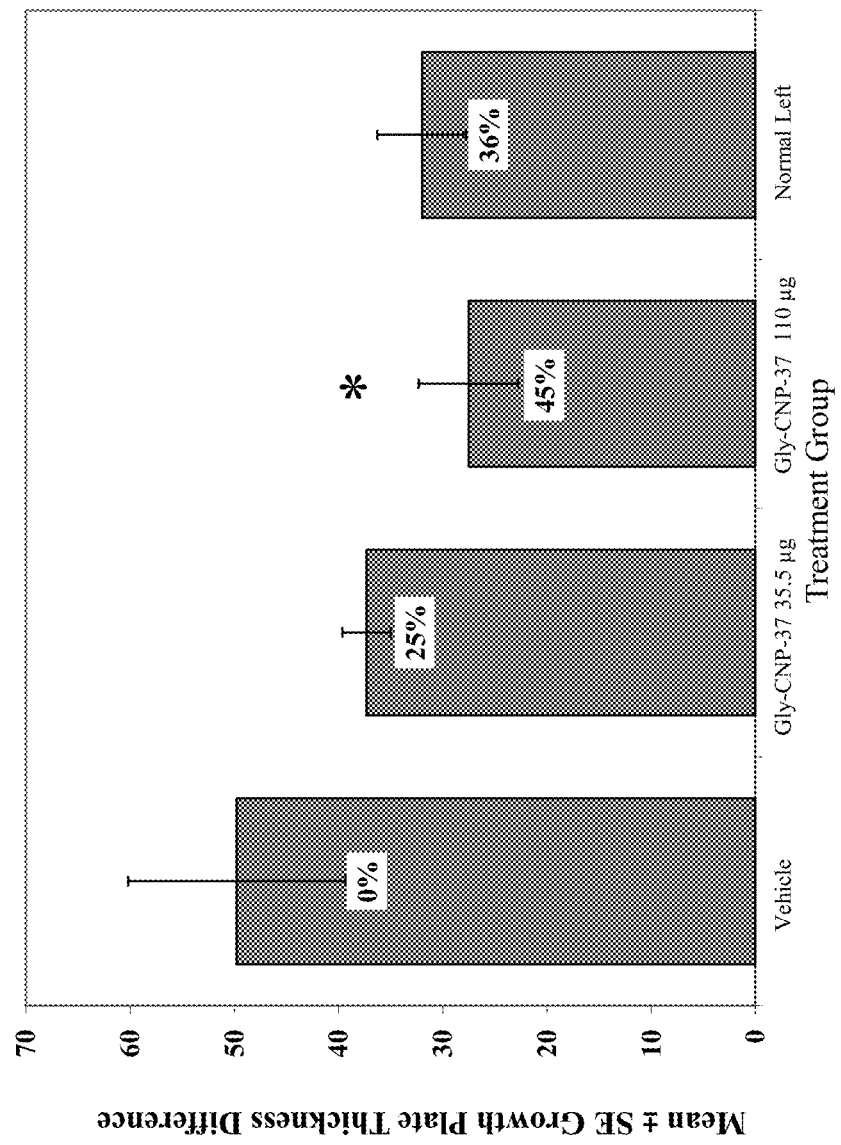
FIG. 8 is a graph representing the data in FIG. 7 in which the lateral thickness was subtracted from the medial to determine the difference between the two. *$p \leq 0.05$ ANOVA to vehicle.

Growth plate thickness was measured in all knees on medial and lateral sides (2 measures/joint) at the approximate midpoint of the medial and lateral physis (assuming a non-tangential area of the section) using an ocular micrometer. Administration of Gly-CNP-37 at a dose of 110 µg significantly reduced medial growth plate thickness. Gly-CNP-37 at a dose of 35.5 µg showed a reduction in medial thickness, but not a significant reduction via statistical analysis (FIG. 7). A differential analysis was also determined, in which the lateral thickness was subtracted from the medial to determine the difference between the two. FIG. 8 shows that using this analysis Gly-CNP-37 at the higher dose significantly reduced the growth plate thickness while the lower dose reduced thickness of the growth plate, but not to the same extent as the higher dose.

Medial Collateral Ligament/Synovial Repair was also analyzed by measuring thickness of the medial synovial/collateral ligament repair in a non-tangential area of the section using an ocular micrometer. These measurement did not show any difference between treatment groups.

Gait Analysis

Gait analysis was performed by applying ink to the ventral surface of the foot and documenting weight bearing during movement (footprints) across paper. Rear feet of rats were placed in ink and then rats were placed on paper and allowed to walk the full length. Gait was scored visually using the criteria in Table 5 (descriptions refer to diseased/affected leg).

TABLE 5

Gait Analysis Scoring Criteria

| SCORE | SCORING CRITERIA |
|---|---|
| 0 | Normal, approximately equal ink staining to normal paw. |
| 1 | Slight limp/pain = reduced inking area relative to the normal paw, but no full regions or structures are missing. |
| 2 | Mild limp/pain = Print extends to the end or near to the end of the "curlicue" structure. If normal paw has very little heel staining (rat walks mainly on toes/ball of foot), then slightly less staining. |
| 3 | Moderate limp/pain = toes and full ball of foot, extending to the top of the "curlicue" foot. If normal paw has very little heel staining (rat walks mainly on toes/ball of foot), then toes with small portion of ball of foot. |
| 4 | Marked limp/pain = toes and partial ball of foot, no heel or posterior foot. If normal paw has very little heel staining (rat walks mainly on toes/ball of foot), then toes only. |
| 5 | Severe limp/pain = toes only, no ball of foot, no heel. If normal paw has very little heel staining (rat walks mainly on toes/ball of foot), then partial toes or non-specific marks. |
| 6 | Hopping or carrying leg, no footprint is evident. |

Figure 9:
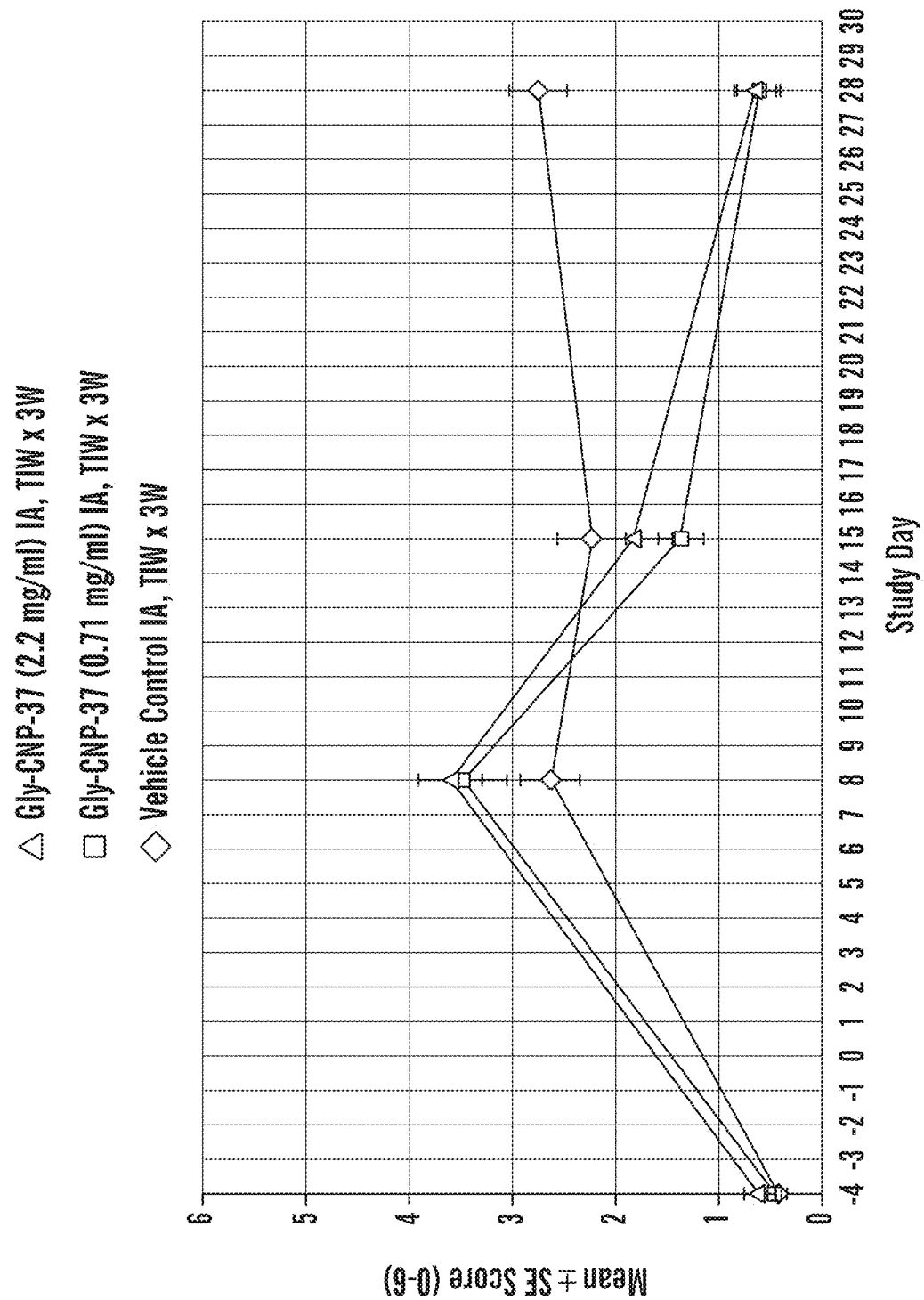
FIG. 9 represents the progression of gait score in Gly-CNP-37 treated or untreated control rats. *$p \leq 0.05$ ANOVA to vehicle.
Figure 10:
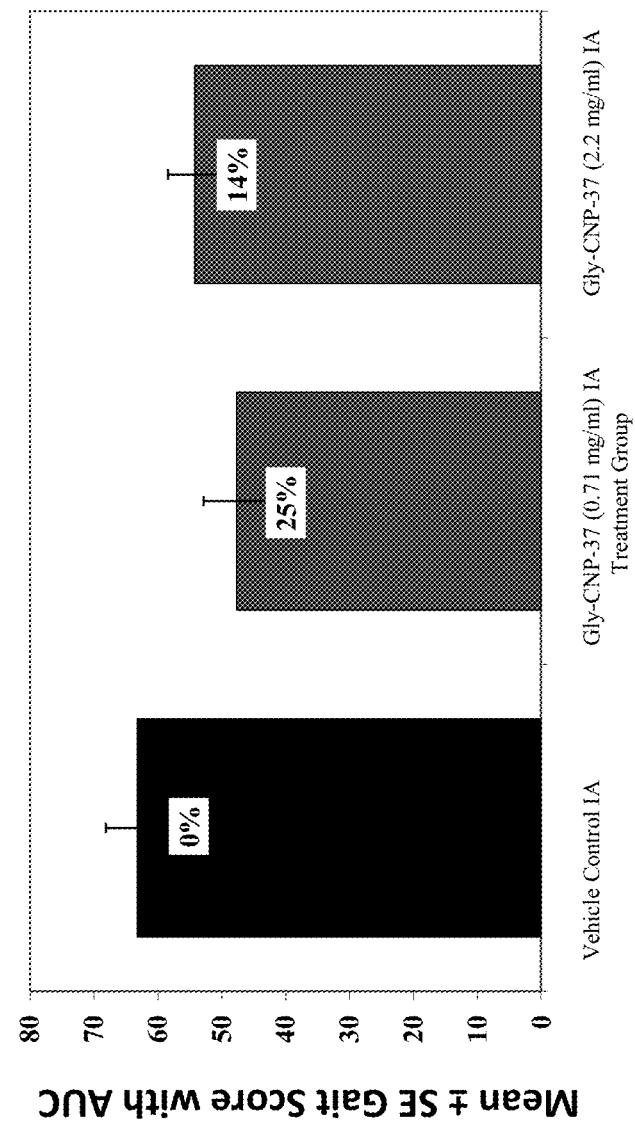
FIG. 10 is a graph representing the Area Under the Curve (AUC) of the gait score of FIG. 9. All values are $p \leq 0.05$ ANOVA to vehicle.

The Gly-CNP-37 treated animals, at either the higher or lower dose, showed an improvement in mobility and gait from approximately day 15 to day 28 of the study (FIG. 9). The Area Under the Curve (AUC) of the gait score was also calculated. FIG. 10 shows that Gly-CNP-37 at the lower dose decreased gait score to a greater extent than the higher CNP dose, with gait score being lower for both treated populations as compared to the untreated controls.

The results presented in this Example 1 indicate that treatment of osteoarthritis with CNP variants such as Gly-CNP-37 shortly after trauma has beneficial effects on symptoms of osteoarthritis, including cartilage degeneration and mobility of the affected subjects.

Example 2

Additional rat studies were performed using the rat model and experimental methodology of Example 1 in order to investigate the potential use of a second CNP variant, Pro-Gly-CNP-37, in treating osteoarthritis and to compare it to Gly-CNP-37.

TABLE 6

Study Desµgn and Groups

| Group Males | No. of Males | Treatment Route | Dose Regimen | Dose Level (mg/mL) | Dose | Concentration | Dose Volume |
|---|---|---|---|---|---|---|---|
| 1 | 12 | Vehicle | IA | TIWx3W | 0 µg | 0 | 50 µL |
| 2 | 12 | Pro-Gly-CNP-37 | IA | TIWx3W | 10.5 µg | 0.21 | 50 µL |
| 3 | 12 | Pro-Gly-CNP-37 | IA | TIWx3W | 35.5 µg | 0.71 | 50 µL |
| 4 | 12 | Pro-Gly-CNP-37 | IA | TIWx3W | 105µg | 2.1 | 50 µL |
| 5 | 12 | Gly-CNP-37 | IA | TIWx3W | 105µg | 2.1 | 50 µL |
| 6 | 15 | Vehicle | SC | QDx3W | 0 µg/kg | 0 | 0.83 mL/kg |
| 7 | 15 | Pro-Gly-CNP-37 | SC | QDx3W | 150 µg/kg | 0.18 | 0.83 mL/kg |

As summarized in Table 6, groups of rats were treated with vehicle, Pro-Gly-CNP-37, or Gly-CNP-37. The dose route was intraarticular (IA) or subcutaneous (SC). The dose scheduling was either intraarticular administration three times per week (M, W, F) for 3 weeks (TIW×3W) or subcutaneous administration once daily for approximately 3 weeks (QD×3W). Rats underwent surgery on Study Day 0; Groups 1-5 underwent surgery approximately 1 week before Groups 6-7 (i.e., the study was conducted in a staggered fashion). IA injections were given as a fixed dose whereas SC injections were given at a given dose per weight based on the most recently recorded body weight. For all rats, body weights were measured predose. For a 300-gram rat, the weekly IA dose regimen for the low, middle, and high levels was approximately equivalent to 15, 50, and 150 µg/kg/day, respectively. Rats were euthanized on day 25 after the final dose and their joints harvested for histopathological analysis and scoring.

Plasma Pharmacokinetics and Pharmacodynamics

The pharmacokinetic (PK) and pharmacodynamic (PD) properties of the CNP variants were evaluated. For the PK/PD analysis, timed blood collections were performed on 3 rats/group/time point as follows: 15, 30, 60, and 120 minutes post dosing for the IA groups and 5, 15, 30, 60, and 120 minutes post dosing for the SC groups. After blood collection, synovial lavage fluid (SLF, ~50 µL/knee) was collected from each rat's left (normal) and right (operated) knee.

Histopathology and Immunohistochemistry

The knees were preserved for histopathology and immunohistochemistry (IHC) analysis. The primary endpoint was histopathological examination of chondrocyte death and cartilage degeneration in the knee including IHC for Proliferating Cell Nuclear Antigen (PCNA). The various histopathological features were measured and scored as described above in Example 1, in particular see Tables 1-5 for scoring criteria.

Figure 11:
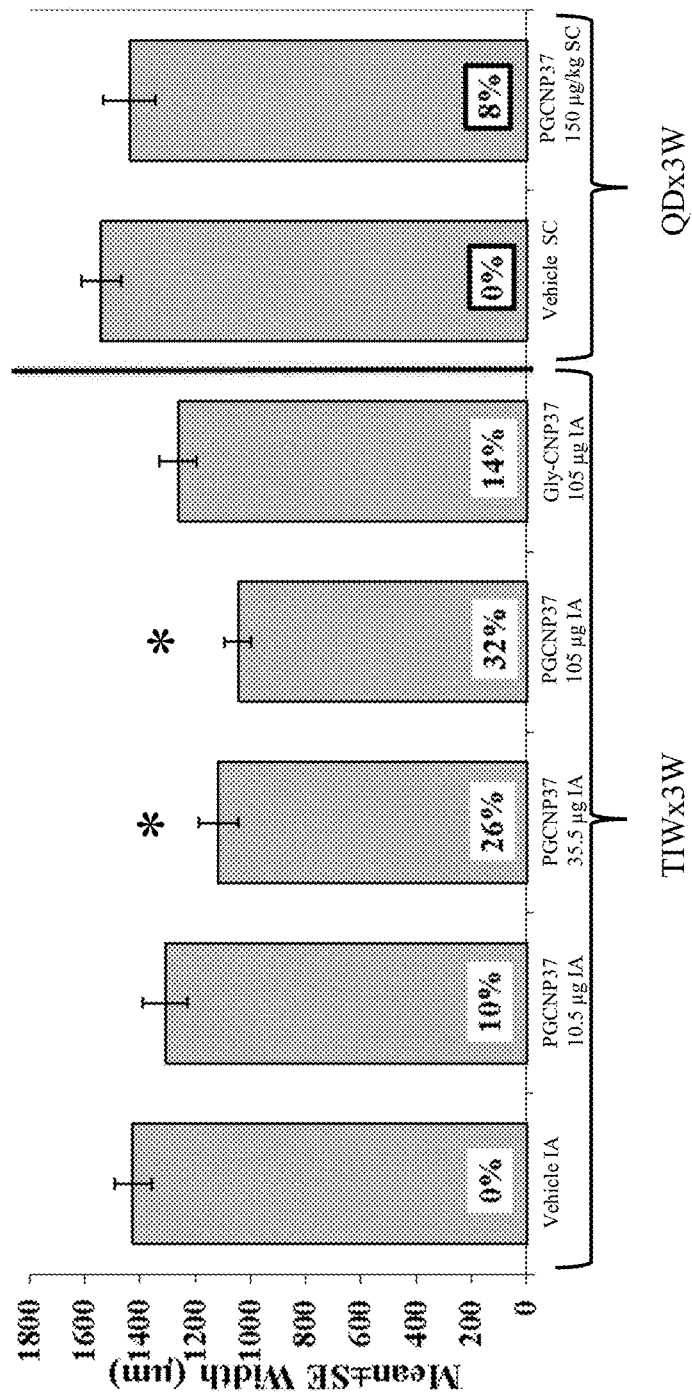
FIG. 11 shows measurements of total cartilage degeneration width for animals treated with Pro-Gly-CNP-37 or Gly-CNP-37. *$p \leq 0.05$ ANOVA to vehicle.

Total width of the tibial cartilage affected by any degeneration (cell loss, proteoglycan loss or collagen damage) was measured by ocular micrometer. As shown in FIG. 11, Pro-Gly-CNP-37 given IA at the middle and high doses significantly reduced total cartilage degeneration width by approximately 26% and 32% respectively. Thus, the IA 35.5 µg and 105 µg doses reached statistical significance for tibial cartilage degeneration width.

Figure 12:
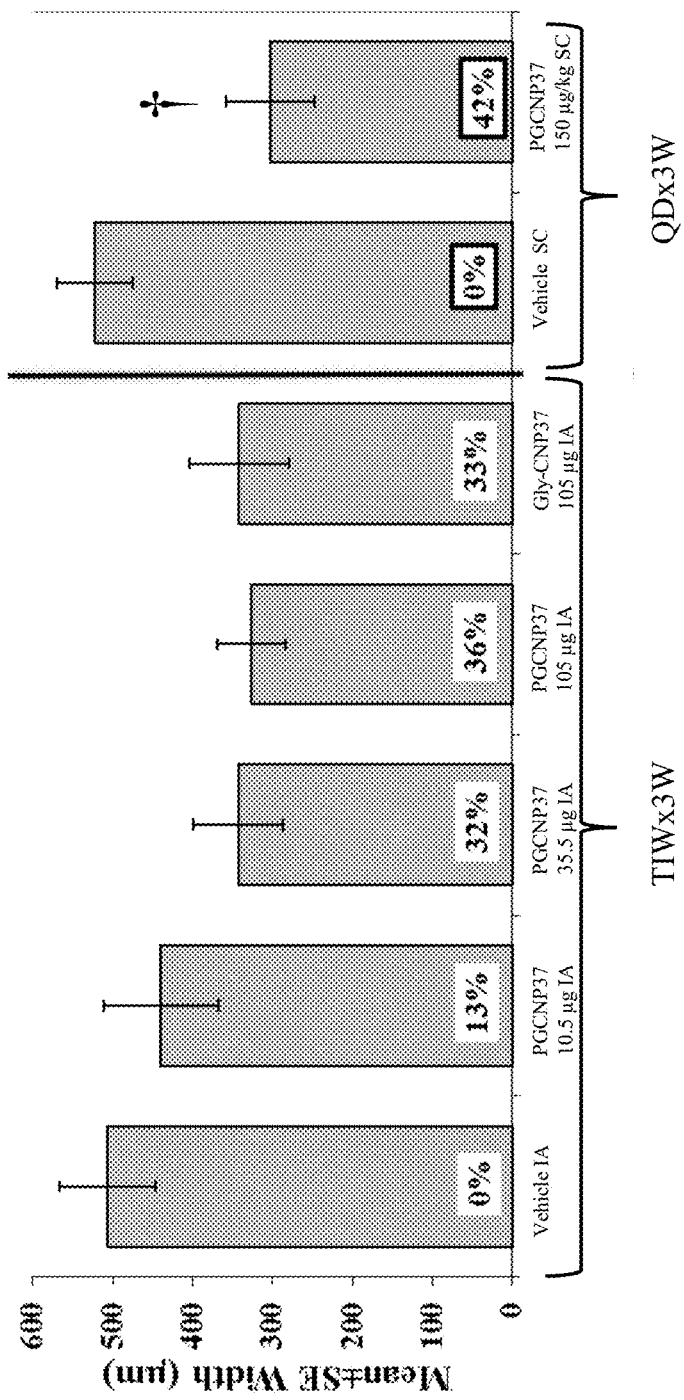
FIG. 12 shows measurements of substantial cartilage degeneration width for animals treated with Pro-Gly-CNP-37 or Gly-CNP-37. †$p < 0.05$ t-test to vehicle SC.

The effect of CNP variants on Substantial Cartilage Degeneration as defined by chondrocyte and proteoglycan loss extending through greater than 50% of the cartilage thickness was measured on the tibial plateau by ocular micrometer. A dose-responsive reduction in Substantial Cartilage Degeneration was observed for Pro-Gly-CNP-37 delivered by the intraarticular route (FIG. 12), with a 32% reduction in width seen with the 35.5 µg IA dose and 36% reduction seen with the 105 µg IA dose. A statistically significant reduction was observed for 150 µg/kg Pro-Gly-CNP-37 given subcutaneously daily for three weeks (a 42% reduction in width).

Figure 13:
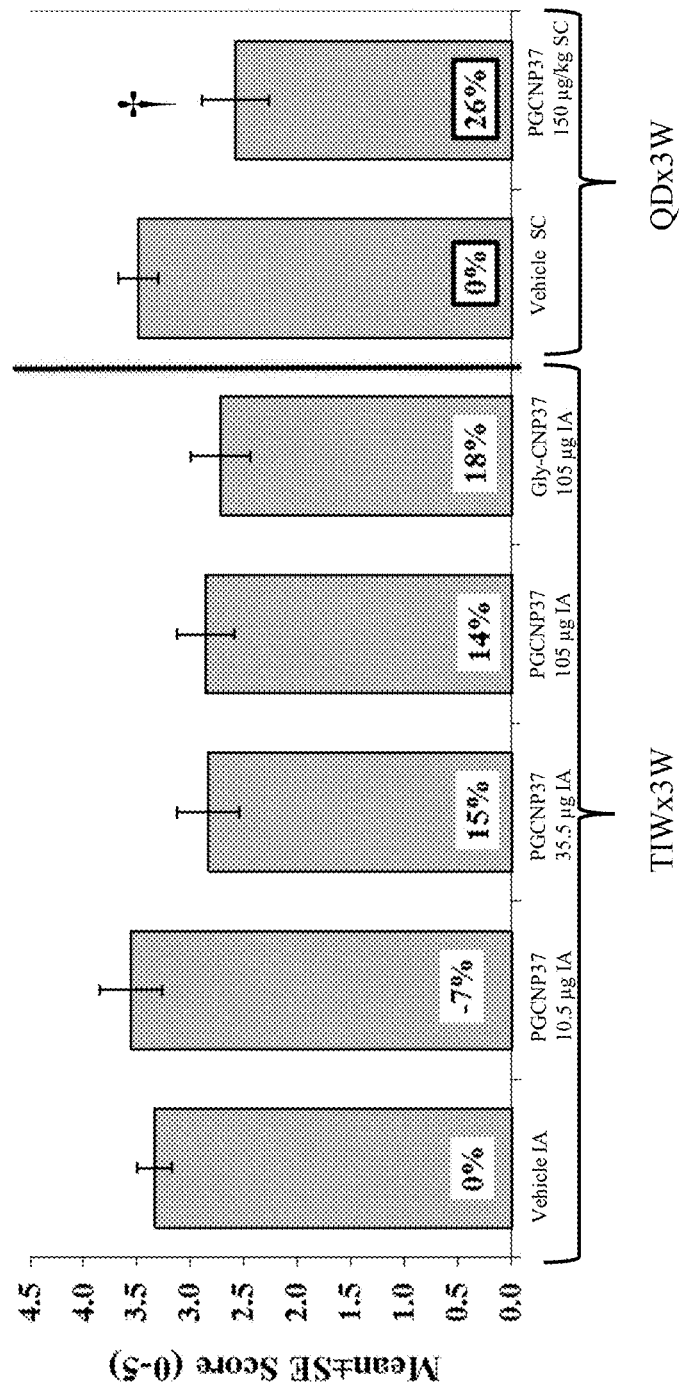
FIG. 13 shows mean Medial Tibial Osteophyte Scores for animals treated with Pro-Gly-CNP-37 or Gly-CNP-37. †$p < 0.05$ t-test to vehicle SC.

Osteophyte thickness (tidemark to furthest point extending toward synovium) was measured with an ocular micrometer. A dose-responsive trend in Medial Tibial Osteophyte Score was observed for Pro-Gly-CNP-37 administered via the IA route (FIG. 13), with a 15% reduction seen at 35.5 µg IA and a 14% reduction seen at 105 µg IA. In addition, a statistically significant reduction ($p < 0.05$ by t-test) of 26% was observed for Pro-Gly-CNP-37 administered subcutaneously.

Figure 14:
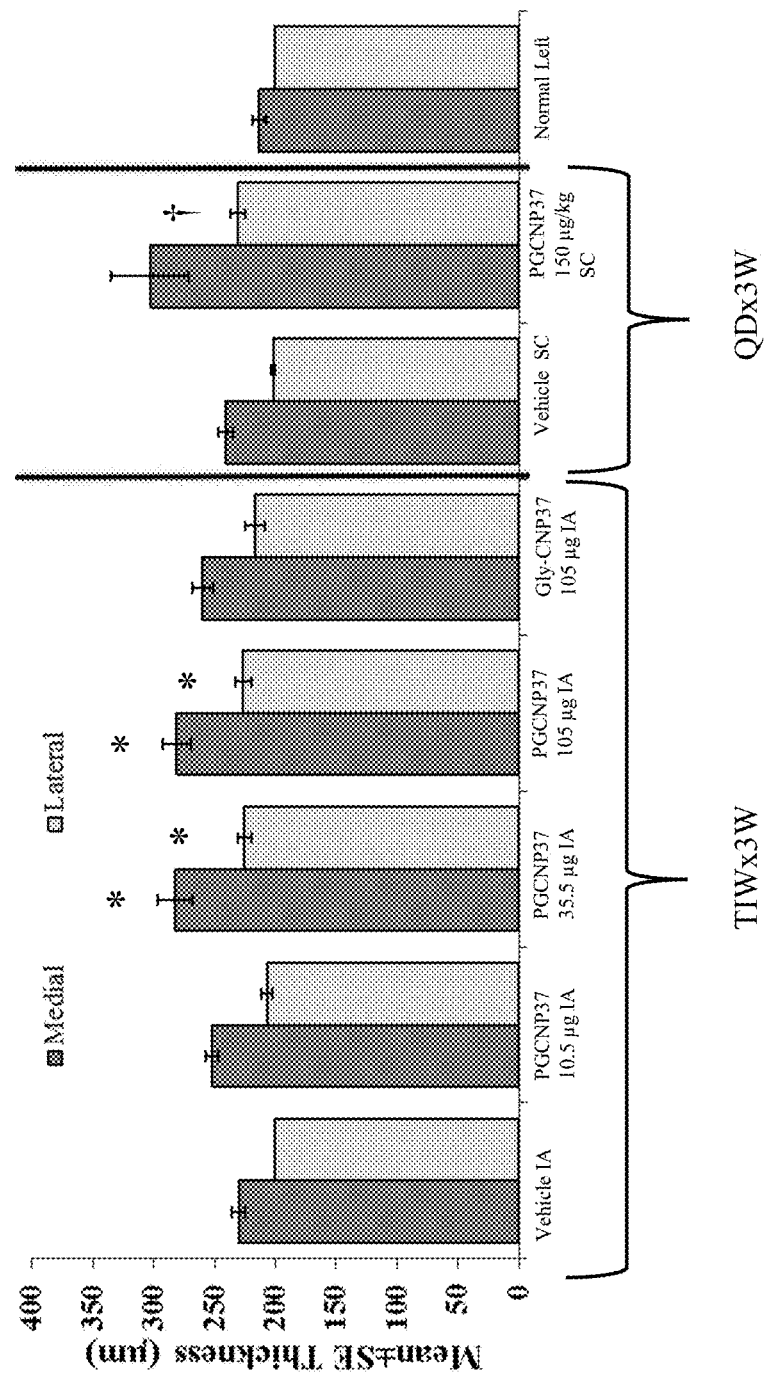
FIG. 14 shows mean growth plate thickness in micrometers for animals treated with Pro-Gly-CNP-37 or Gly-CNP-37. *$p \leq 0.05$ ANOVA to vehicle. †$p < 0.05$ t-test to vehicle SC.

The thickness of the growth plate was measured for each of the groups. Medial and lateral growth plate thickness was significantly larger in animals treated IA with both 35.5 µg IA and 105 µg IA of Pro-Gly-CNP-37 (FIG. 14). Further, medial and lateral growth plate thickness were also larger in animals treated SC with Pro-Gly-CNP-37 vs vehicle.

Figure 15:
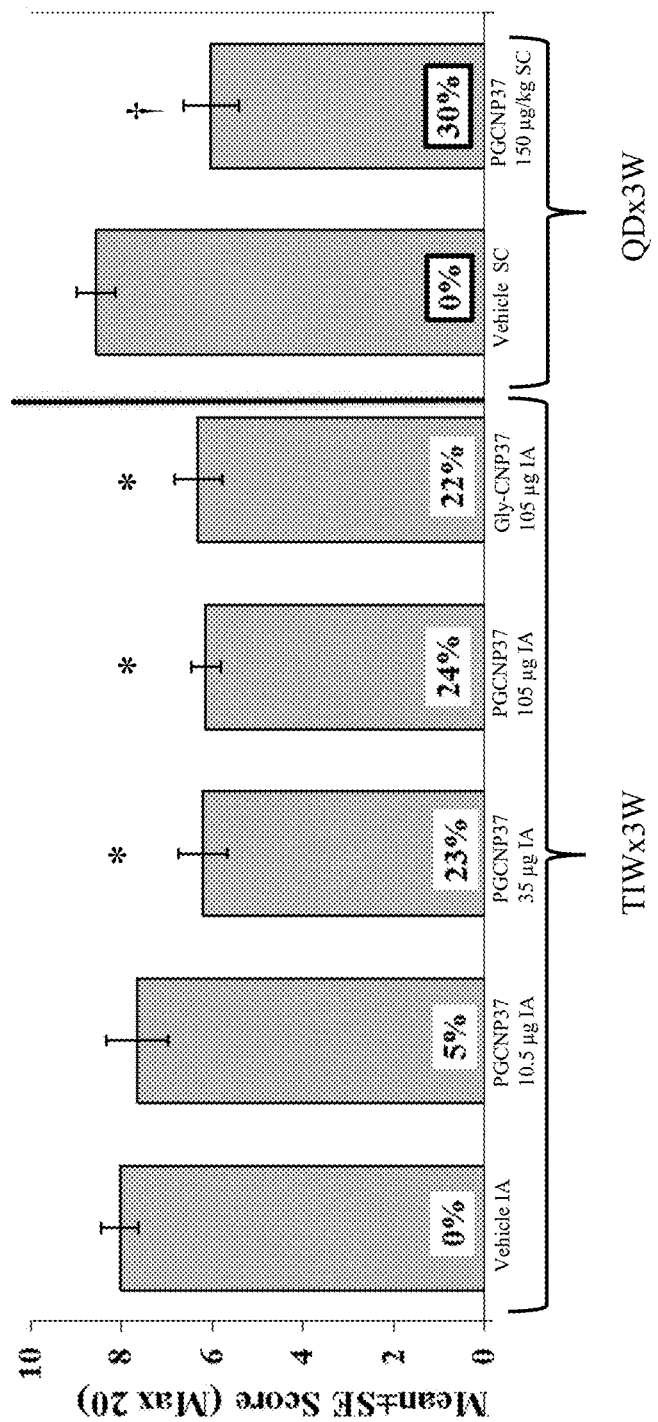
FIG. 15 shows mean total joint scores (minus femur) for animals treated with Pro-Gly-CNP-37 or Gly-CNP-37. *p≤0.05 ANOVA to vehicle. †p<0.05 t-test to vehicle SC.

The total joint scores (without femur) were calculated by summing each of the three-zone scores of the tibial cartilage degeneration and the osteophyte score. As seen in FIG. 15, significant reduction in joint score severity was observed for IA administration of 35.5 and 105 µg Pro-Gly-CNP-37 and also for 105 µg of Gly-CNP-37. Significant reduction in total joint score (minus femur) was also observed for Pro-Gly-CNP-37 given SC.

Figure 16:
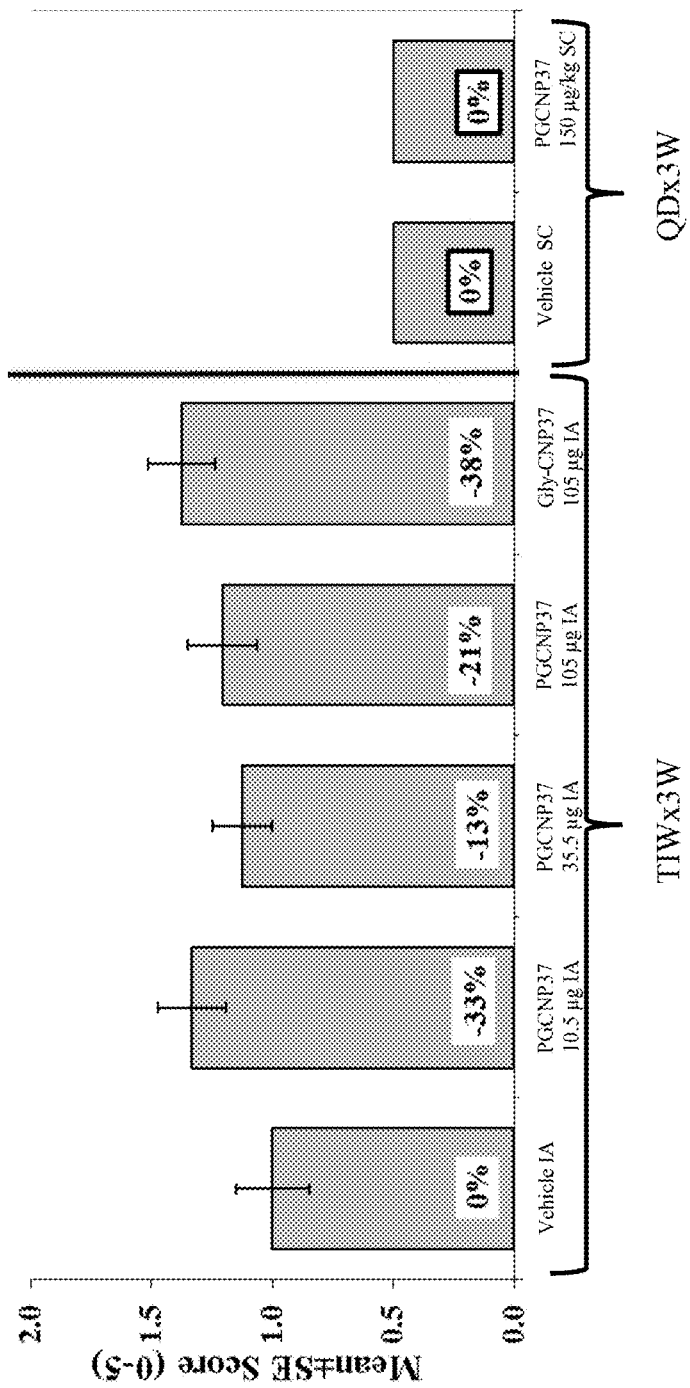
FIG. 16 shows mean synovitis scores for animals treated with Pro-Gly-CNP-37 or Gly-CNP-37.

FIG. 16 shows synovitis scores. Synovial inflammation (mainly mononuclear cell infiltration concentrated on the medial side) was scored using the criteria in Table 7.

TABLE 7

Synovium Inflammation Scoring

| SCORE | SCORING CRITERIA |
|---|---|
| 0 | Normal synovium. |
| 0.5 | ery minimal synovitis (generally focal or scattered minimal diffuse). |
| 1 | Minimal synovitis (generally focal or scattered minimal diffuse). |
| 2 | Mild synovitis (multifocal to confluent areas of mild mononuclear cell infiltration). |
| 3 | Moderate synovitis (confluent areas of moderate mononuclear cell infiltration). |
| 4 | Marked synovitis (confluent areas of marked mononuclear cell infiltration). |
| 5 | Severe synovitis (confluent areas of severe mononuclear cell infiltration). |

No significant increases in synovitis scoring severity were observed across all dose groups. Endotoxin was below the limit of quantitation (<0.5 EU/mL) in all formulations, except in Gly-CNP-37 (0.78 EU/mL).

Figure 17:
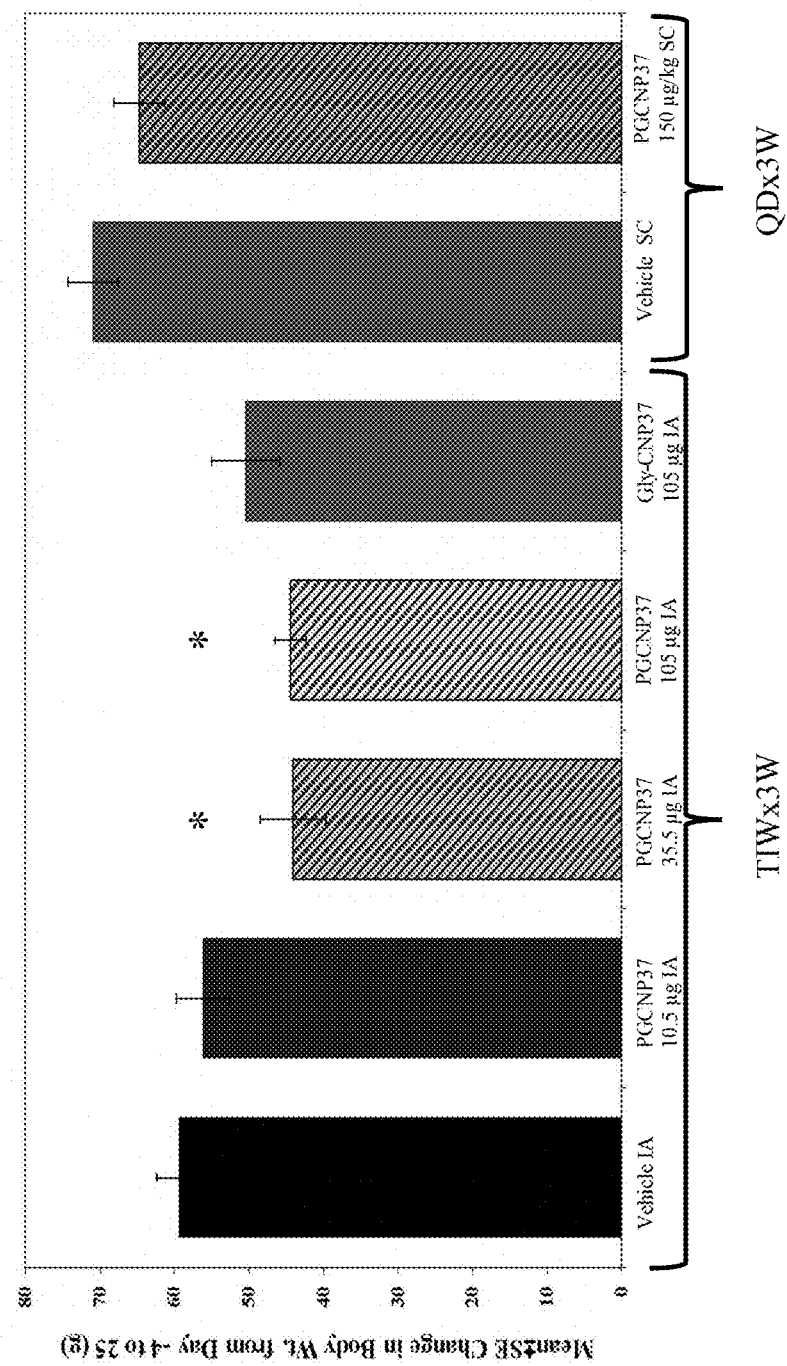
FIG. 17 shows mean change in body weight for animals treated with Pro-Gly-CNP-37 or Gly-CNP-37. *p≤0.05 ANOVA to vehicle.

FIG. 17 shows mean changes in body weight (in grams) from day −4 to 25 for the different groups. A significant reduction in body weight gain was observed for Pro-Gly-CNP-37 given IA at both the 35.5 and the 105 µg/dose and given SC at the 150 µg/kg/day dose.

Figure 18:
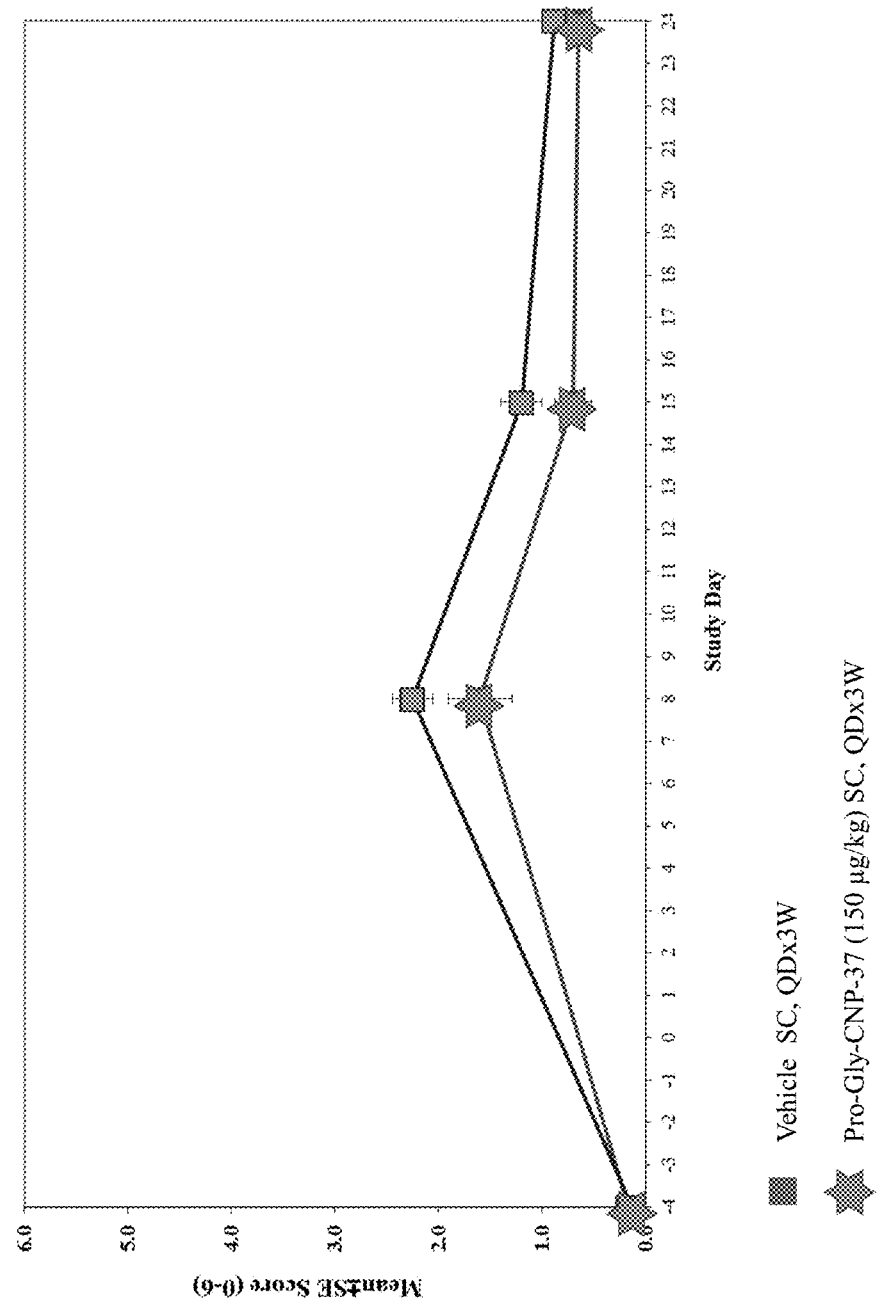
FIG. 18 shows mean gait scores for animals treated with Pro-Gly-CNP-37 or Gly-CNP-37. Values are p<0.05 t-test to vehicle SC.

FIG. 18 shows gait analysis scores from the groups. Gait score was significantly reduced (48%) for Pro-Gly-CNP-37 delivered subcutaneously compared to vehicle on Day 8.

Figure 19:
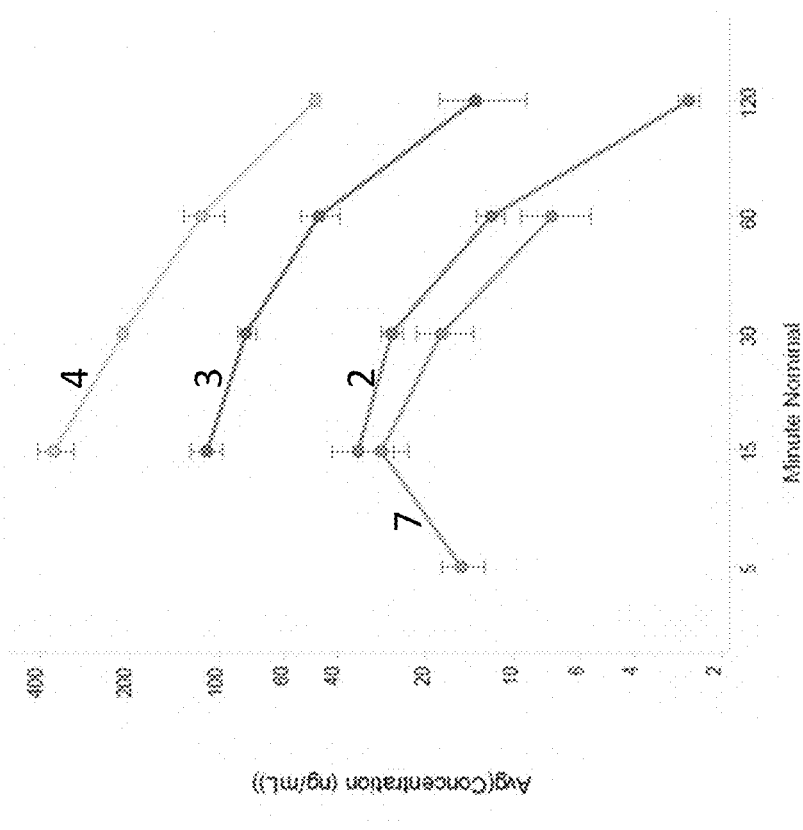
FIG. 19 shows a time course for average plasma concentration of Pro-Gly-CNP-37 in animals after administration of Pro-Gly-CNP-37 via the intrarterial or subcutaneous route for each study group. For each line the corresponding study group number is presented immediately above the corresponding data line.

FIG. 19 and Table 8 show plasma pharmacokinetics for the animals treated with Pro-Gly-CNP-37 (Groups 2, 3, and 4 (IA administration) and Group 7 (SC administration)). Individual plasma samples were analyzed for Pro-Gly-SNP-37 levels and mean concentration vs. time profiles were analyzed using a non-compartmental model for extravascular administration in Phoenix WinNonlin software. The data for each group is plotted and labeled (above each line) with the corresponding number group in FIG. 19. Pro-Gly-CNP-37 appeared rapidly in systemic circulation following both IA and SC injections. Exposure for IA injections (Groups 2, 3, and 4) was generally dose-proportional, with no marked change in $t_{1/2}$ and CL. Although the exposure was similar to the lowest IA dose investigated, once-daily SC injections (Group 7) appeared to provide a response that was similar in efficacy to the two highest dose IA injections that were given three times/week.

TABLE 8

Pharmacokinetics of CNP variants

| Group | $C_{max}$ (ng/mL) | $AUC_{last}$ (ng-min/mL) | $T_{max}$ (min) | $t_{1/2}$ (min) | CL (mL/min) |
|---|---|---|---|---|---|
| 2 | 33.8 | 1719 | 15 | 27.0 | 5.77 |
| 3 | 110 | 5939 | 15 | 34.9 | 5.36 |
| 4 | 357 | 8827 | 15 | 38.1 | 9.19 |
| 7 | 28.4 | 980 | 15 | 23.8 | 121 |

The data indicate that intraarticular treatment with Pro-Gly-CNP-37 (35.5 and 105 µg) or Gly-CNP-37 (105 µg) had significant beneficial effects on histopathology lesions of medial meniscal tear-induced osteoarthritis in rats.

Once-daily subcutaneous treatment with 150 µg/kg/day Pro-Gly-CNP-37 provided similar or better efficacy than the intraarticular treatments. Overall, the studies show evidence of chondroprotective effects.

Example 3

A model of late stage osteoarthritis was used to evaluate the efficacy of Pro-Gly-CNP-37 in pre-developed osteoarthritis (i.e., primary osteoarthritis). As described above in Examples 1 and 2, osteoarthritis was induced in the rear legs of rats by severing the meniscus. However, in contrast to Examples 1 and 2, the lesion pathology was allowed to progress for three weeks before IA or SC treatment with Pro-Gly-CNP-37 thereby simulating pre-existing OA (i.e., primary osteoarthritis). The overall study design is outlined in Table 9. In particular, male Lewis rats underwent a unilateral medial meniscal tear surgery on Study Day 0; administration of control vehicle or Pro-Gly-CNP-37 began on Study Day 21; and animals were euthanized at scheduled time points following the last dose on Study Day 22 (Groups 1-4) or Study Day 40 (Groups 5-11). The primary endpoints evaluated included histopathological examination of chondrocyte death/cartilage degeneration in the knee.

TABLE 9

Late Stage Osteoarthritis Study Design and Groups

| Group | Operated | Treatment | Dose Level | ROA | Termination |
|---|---|---|---|---|---|
| 1 & 6 | Yes | Vehicle | 0 µg | IA | Day 22 or 41 |
| 7 | Yes | Pro-Gly-CNP-37 | 35.5 µg | IA | Day 41 |
| 2 & 8 | Yes | Pro-Gly-CNP-37 | 105 µg | IA | Day 22 or 41 |
| 3 & 9 | Yes | Vehicle | 0 µg/kg | SC | Day 22 or 41 |
| 10 | Yes | Pro-Gly-CNP-37 | 50 µg/kg | SC | Day 41 |
| 4 | Yes | Pro-Gly-CNP-37 | 150 µg/kg | SC | Day 22 or 41 |
| 5 | No | None | N/A | N/A | Day 41 |

All animals survived to the scheduled study termination points. At the end of the study, the rats were euthanized and their knees were collected, fixed, and sectioned for histopathological analysis and scored as in Tables 1-5, and 7. A summary of the study results is presented in Table 10.

Treatment with Pro-Gly-CNP-37 (35.5 or 105 µg) dosed IA, TIW×3W and treatment with Pro-Gly-CNP-37 (150 µg/kg) dosed SC, QD×3W showed slight to significant beneficial effect in later stage rat meniscal tear-induced osteoarthritis as determined by evaluation of knee histopathology. Results of IA treatment with Pro-Gly-CNP-37 were dose responsive.

Arthritis parameters were generally similar across vehicle control groups although lesion severity was slightly increased in SC controls as compared to IA controls with the exception of synovitis, which was reduced in SC treated rats. Body weight gain was significantly increased in SC vehicle controls 40 days post-surgery as compared to IA controls.

TABLE 10

Summary of Clinical and Histopathology Data

| Group | Treatment | Total Tibial CD Width (μm) | Substantial Tibial CD Width (μm) | Total Tibial CD Score | Osteophyte Measurement (μm) | Total Joint Score w/ Femur |
|---|---|---|---|---|---|---|
| 1 | Vehicle IA, 1x(d21) Necropsy Day 22 | 1633.3 (195.88) | 480.56 (113.89) | 4.83 (0.76) | 341.67 (24.25) | 7.89 (0.99) |
| 2 | Pro-Gly-CNP-37 (105μg) IA, 1x(d21) Necropsy Day 22 | 1694.44 (134.83) | 480.56 (92.64) | 4.81 (0.49) | 402.78 (25.61) | 8.97 (0.64) |
| 3 | Vehicle SC, 1x (d21) Necropsy Day 22 | 1577.78 (110.78) | 569.44 (92.04) | 5.39 (0.65) | 375.00 (18.63) | 9.36 (1.02) |
| 4 | Pro-Gly-CNP-37 (150 μg/kg) SC, 1x (d21) Necropsy Day 22 | 1550.00 (109.80) | 572.22 (58.95) | 5.14 (0.34) | 383.33 (23.96) | 8.86 (0.62) |
| 5 | Normal Necropsy Day 40 | 111.11†‡ (37.18) | 0.00†‡ (0.00) | 0.08†‡ (0.04) | 0.00†‡(0.00) | 0.08†‡ (0.04) |
| 6 | Vehicle IA, TIWx3W Necropys Day 40 | 1622.22 (107.88) | 509.72 (57.79) | 4.93 (0.43) | 441.67 (15.56) | 9.07 (0.65) |
| 7 | Pro-Gly-CNP-37 (35.5 μg) IA, TIWx3W Necropsy Day 40 | 1605.56 (71.38) | 358.33 (71.38) | 3.96 (0.46) | 452.78 (22.74) | 8.44 (0.60) |
| 8 | Pro-Gly-CNP-37 IA, TIWx3W Necropsy Day 40 | 1200.00* (69.63) | 313.89 (51.12) | 3.43* (0.32) | 423.61 (28.53) | 7.38 (0.73) |
| 9 | Vehicle SC, QDx3W Necropsy Day 40 | 1741.67 (75.22) | 526.39 (51.84) | 5.06 (0.39) | 472.22 (22.41) | 9.75 (0.69) |
| 10 | Pro-Gly-CNP-37 (50 μg) Sc, QDx3W Necropsy Day 40 | 1847.22 (46.14) | 498.61 (60.18) | 4.83 (0.41) | 473.61(0.41) | 9.82 (0.73) |
| 11 | Pro-Gly-CNP-37 (150 μg) SC, QDx3W Necropsy Day 40 | 1375.00* (98.91) | 443.06 (80.70) | 4.43 (0.59) | 444.44 (18.95) | 9.03 (0.85) |

CD =Cartilage Degeneration,
IA =Intra-articular,
SC =Subcutaneous,
TIWx3W =Three times per week for three weeks,
QDx3W = Once daily for approximately 3 weeks (20 days).
(SE) = Standard error displayed in parenthesis.
*$p<0.05$ ANOVA/K-W test (Dunnett's/Dunn's post-hoc) vs. respective IA or SC Vehicle (Day 40) control.
†0.05 Student's t-test/M-W test vs. IA Vehicle (Day 40).
‡0.05 Student's t-test/M-W test vs. SC Vehicle (Day 40).

Rats treated IA with 35.5 μg Pro-Gly-CNP-37 had significantly (31%) reduced zone-2 tibial cartilage degeneration scores as compared to IA vehicle controls. Tibial cartilage degeneration summed scores and substantial tibial cartilage degeneration widths were non-significantly reduced by 20% and 30%, respectively. Zone-3 medial tibial cartilage degeneration scores and zone-1 femoral cartilage degeneration scores were increased significantly although lesions were generally minimal or mild when present.

Rats treated IA with 105 μg Pro-Gly-CNP-37 had significantly reduced body weight gain as compared to IA vehicle controls. IA treatment with 105 μg Pro-Gly-CNP-37 significantly reduced zone-2 medial tibial cartilage degeneration (44% reduction), zone-3 medial tibial cartilage degeneration (93%), summed medial tibial cartilage degeneration (31%), and total tibial cartilage degeneration widths (28%) as compared to IA vehicle controls. Substantial tibial cartilage degeneration widths were non-significantly (38%) reduced by treatment.

Rats treated SC with 150 μg/kg Pro-Gly-CNP-37 had significantly reduced body weight gain compared to SC vehicle controls. Treatment with 150 μg/kg Pro-Gly-CNP-37 (SC) significantly reduced total tibial cartilage degeneration widths (22% reduction) as compared to SC vehicle controls. Substantial tibial cartilage degeneration widths were non-significantly (16%) reduced by treatment. Medial and lateral growth plate thickness was significantly increased by treatment, contributing to a significant reduction in the difference between medial and lateral thickness.

Figure 20:
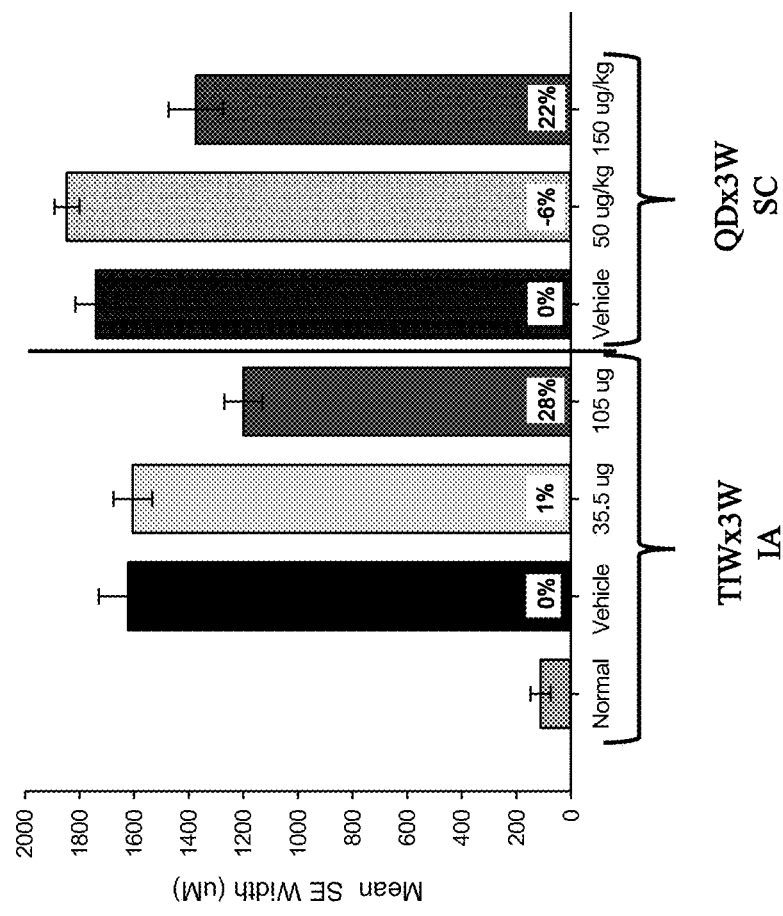
FIG. 20 shows the mean total tibial cartilage degeneration width for animals treated with Pro-Gly-CNP-37 (both intraarticularly ("IA") and subcutaneously ("SC")) in a late stage osteoarthritis model (treatment administration starts twenty-one days after surgery, data collected on day forty).
Figure 21:
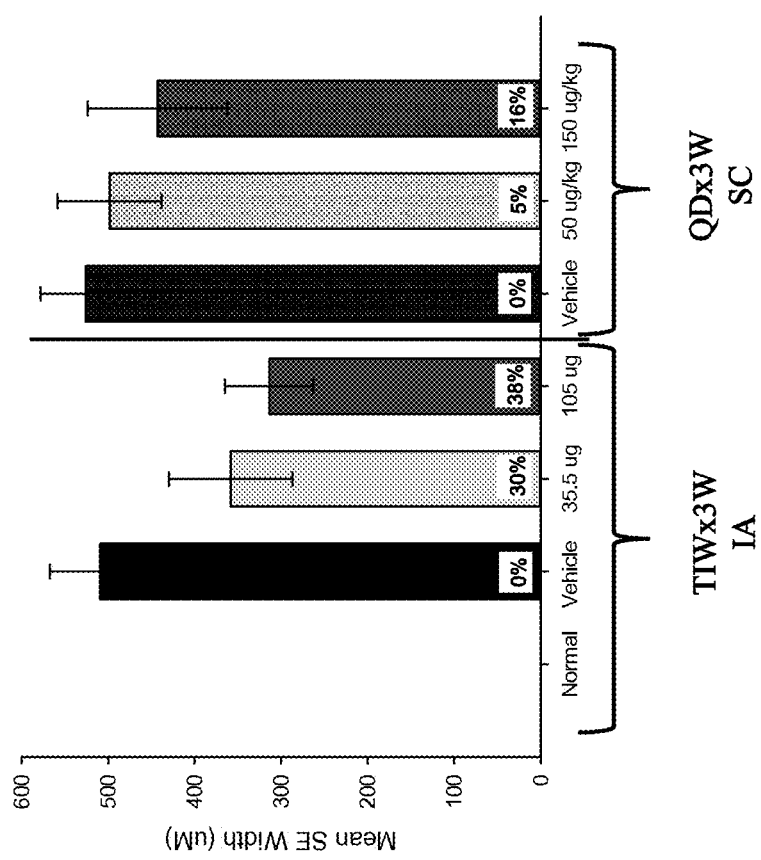
FIG. 21 shows the mean substantial tibial cartilage degeneration width for animals treated with Pro-Gly-CNP-37 (both intraarticularly ("IA") and subcutaneously ("SC")) in a late stage osteoarthritis model (treatment administration starts twenty-one days after surgery, data collected on day forty).
Figure 22:
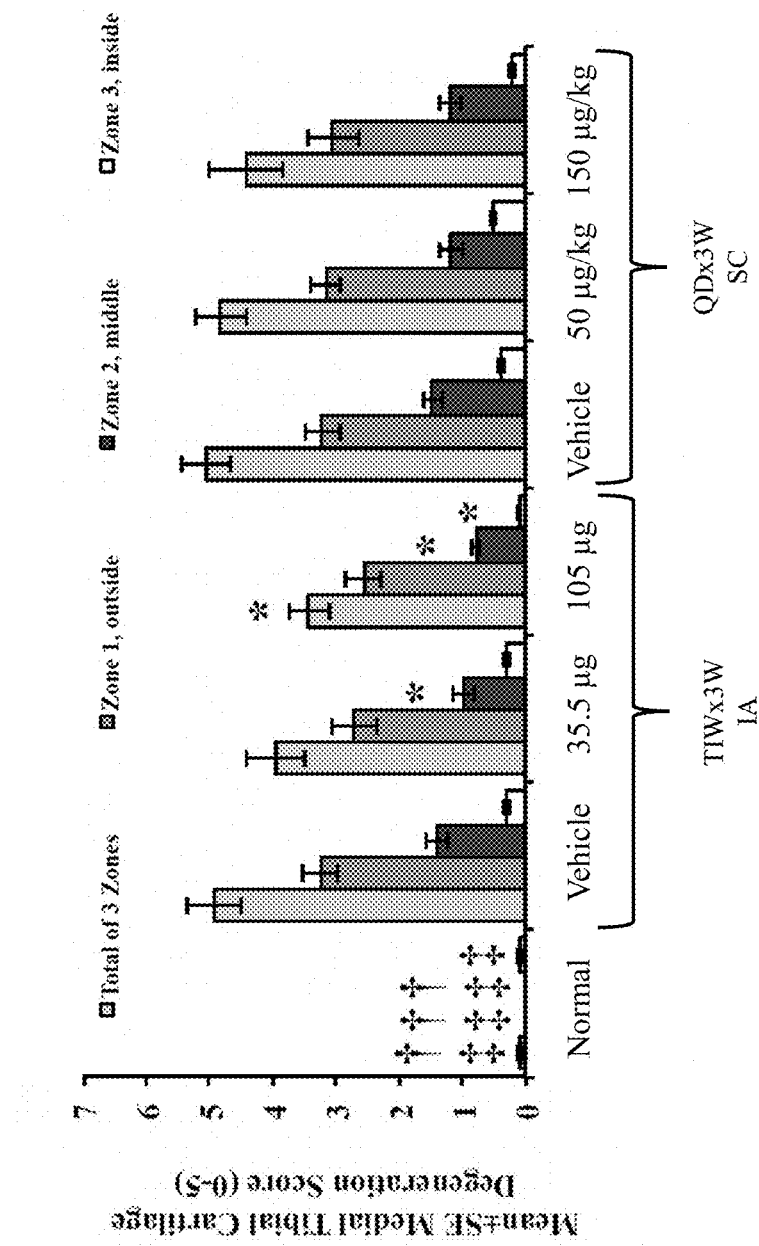
FIG. 22 shows the mean tibial cartilage degeneration scores for each of the three zones and total for animals treated with Pro-Gly-CNP-37 (both intraarticularly ("IA") and subcutaneously ("SC")) in a late stage osteoarthritis model (treatment administration starts twenty-one days after surgery). *p<0.05 K-W test (Dunn's post-hoc) vs. respective IA or SC Vehicle (Day 40) control. †p<0.05 M-W test vs. IA Vehicle (Day 40). ‡p<0.05 M-W test vs. SC Vehicle (Day 40).
Figure 23:
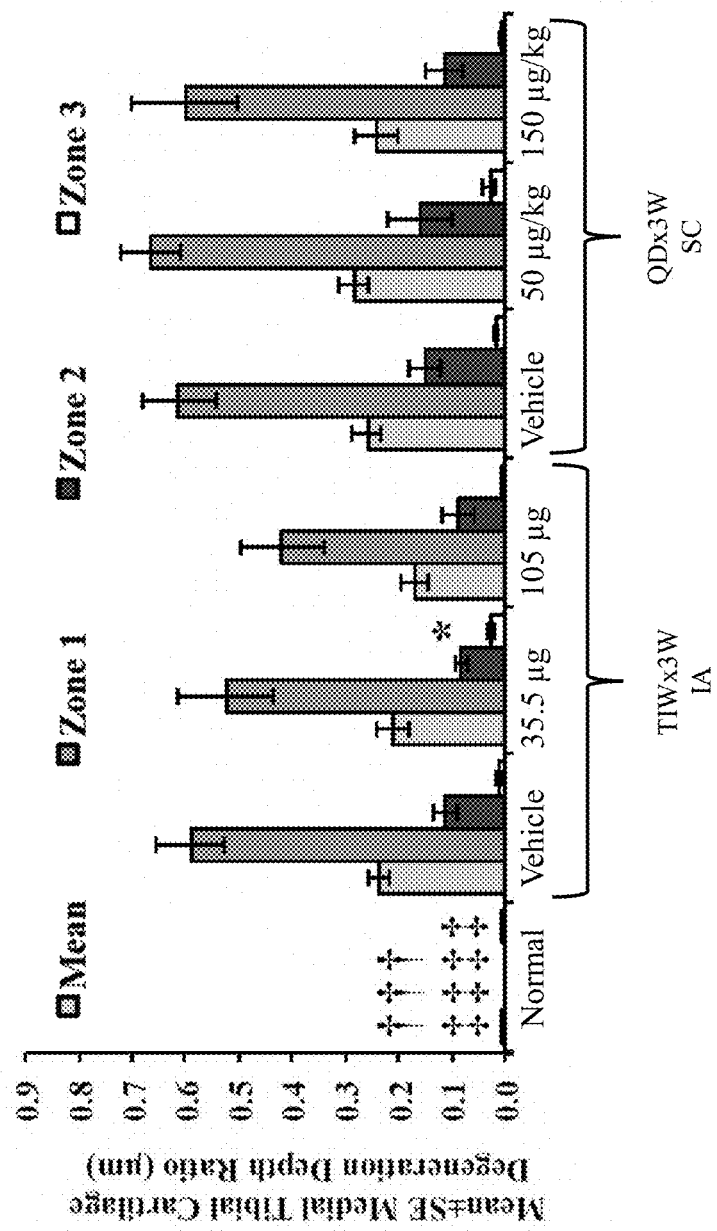
FIG. 23 shows the mean tibial cartilage degeneration depth rations for each of the three zones and the mean for animals treated with Pro-Gly-CNP-37 (both intraarticularly ("IA") and subcutaneously ("SC")) in a late stage osteoarthritis model (treatment administration starts twenty-one days after surgery). *p<0.05 K-W test (Dunn's post-hoc) vs. respective IA or SC Vehicle (Day 40) control. †p<0.05 M-W test vs. IA Vehicle (Day 40). ‡p<0.05 M-W test vs. SC Vehicle (Day 40).

As shown in FIG. 20, Pro-Gly-CNP-37 treatment at 105 μg IA and at 150 μg/kg SC resulted in a decrease in the mean tibial cartilage degeneration. However, substantial tibial cartilage degeneration was decreased by both IA treatment doses as well as the highest SC dose (FIG. 21). Further, Pro-Gly-CNP-37 administered IA has resulted in a statistically significant reduction in medial tibial cartilage degeneration scores (FIG. 22) and medial tibial cartilage degeneration depth ratios (FIG. 23).

Figure 24:
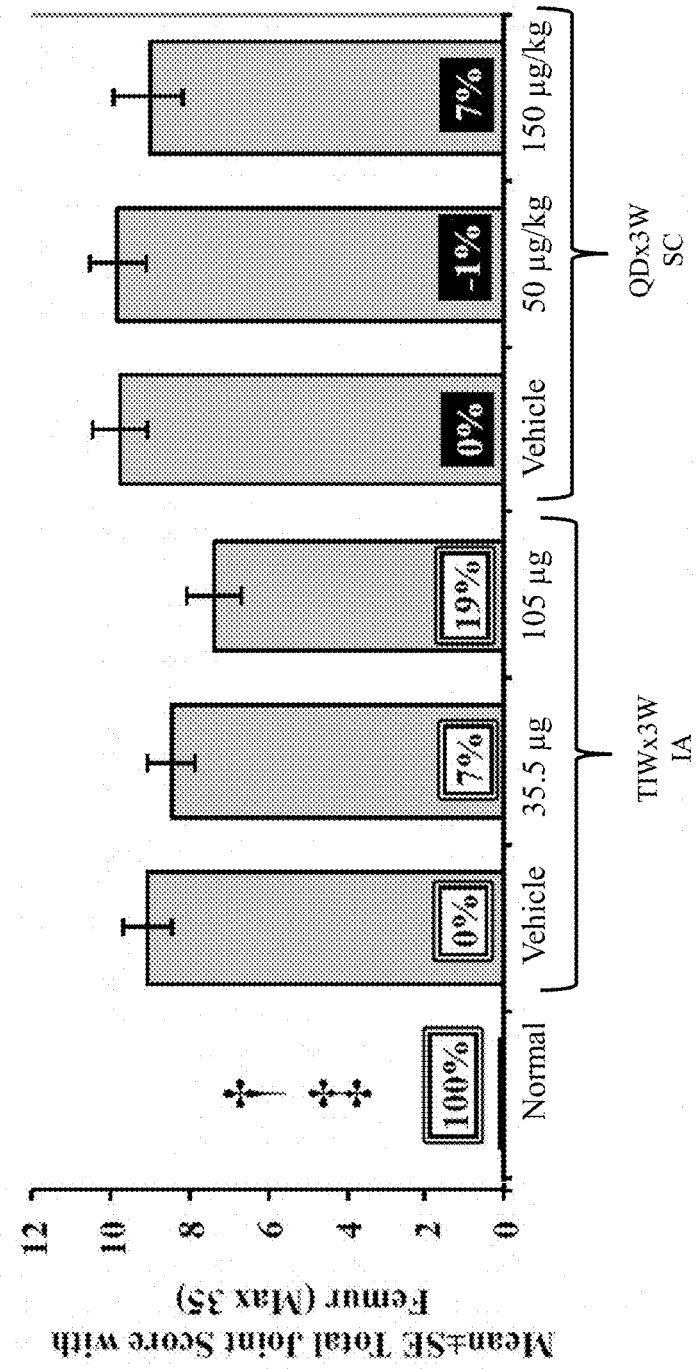
FIG. 24 shows the total joint score with femur for each of the three zones and the mean for animals treated with Pro-Gly-CNP-37 (both intraarticularly ("IA") and subcutaneously ("SC")) in a late stage osteoarthritis model (treatment administration starts twenty-one days after surgery). †p<0.05 M-W test vs. IA Vehicle (Day 40). ‡p<0.05 M-W test vs. SC Vehicle (Day 40).
Figure 25:
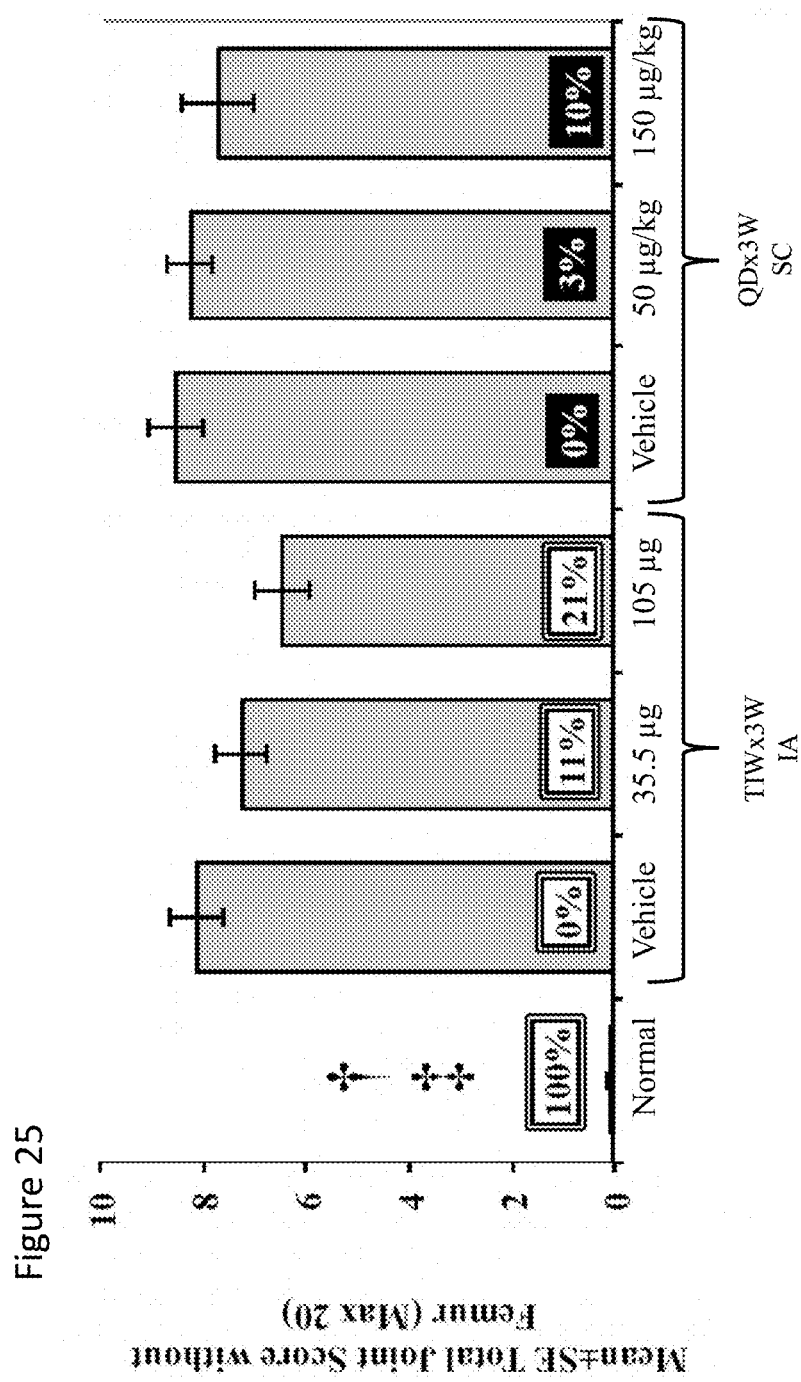
FIG. 25 shows the total joint score without femur for each of the three zones and the mean for animals treated with Pro-Gly-CNP-37 (both intraarticularly ("IA") and subcutaneously ("SC")) in a late stage osteoarthritis model (treatment administration starts twenty-one days after surgery). †p<0.05 M-W test vs. IA Vehicle (Day 40). ‡p<0.05 M-W test vs. SC Vehicle (Day 40).

As described above in Examples 1 and 2, total joint scores were calculated for each joint (with and without femur) by histopathological analysis and scoring. Pro-Gly-CNP-37 administered IA resulted in a 7% (35.5 μg) and a 19% (105 μg) decrease in joint scores with femur and an 11% (35.5 μg) and 21% (105 μg) decrease when calculated without femur (FIG. 24 (with femur) and 25 (without femur). Pro-Gly-CNP-37 administered SC had more modest decreases at the highest dose level (150 μg/kg) of 7% (with femur) and 10% (without femur)(FIGS. 24 and 25).

Figure 26:
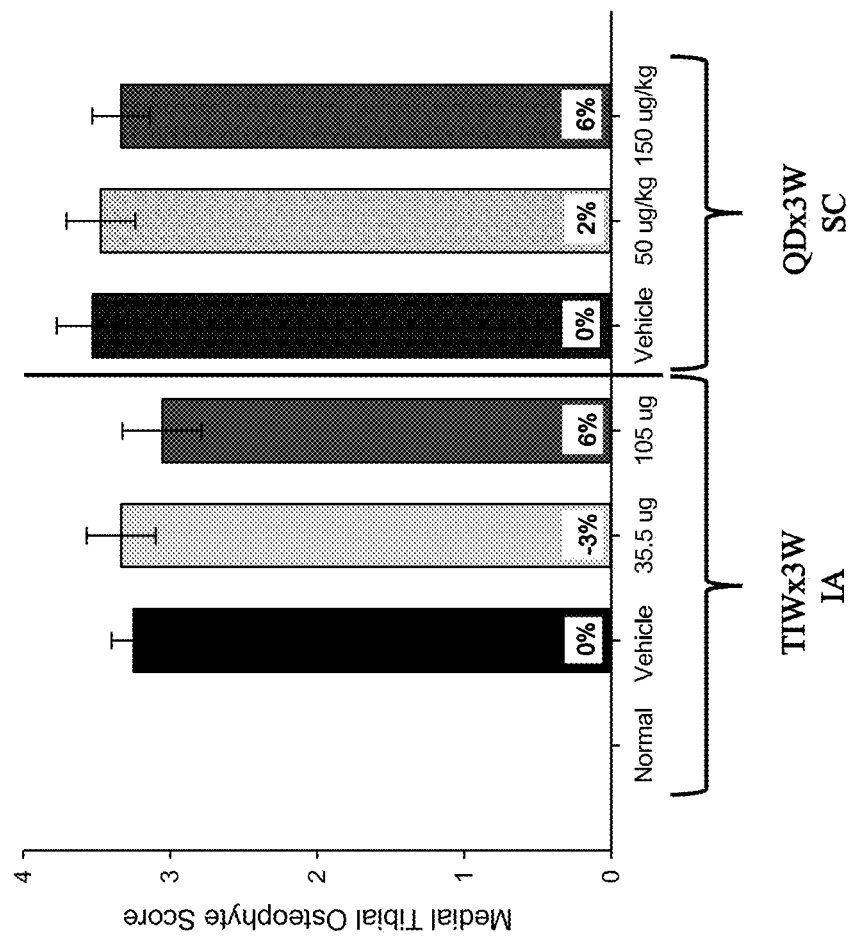
FIG. 26 shows the osteophyte score for animals treated with Pro-Gly-CNP-37 (both intraarticularly ("IA") and subcutaneously ("SC")) in a late stage osteoarthritis model (treatment administration starts twenty-one days after surgery, data collected on day forty).
Figure 27:
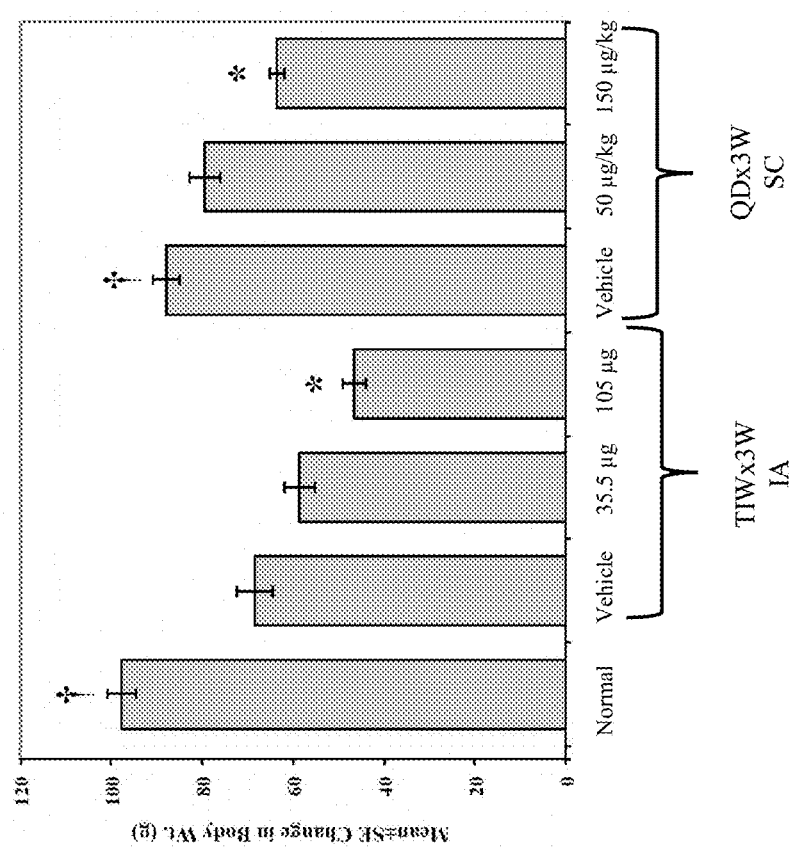
FIG. 27 shows the change in body weight for animals treated with Pro-Gly-CNP-37 (both intraarticularly ("IA") and subcutaneously ("SC")) in a late stage osteoarthritis model (treatment administration starts twenty-one days after surgery). *p<0.05 K-W test (Dunn's post-hoc) vs. respective IA or SC Vehicle (Day 40) control. †p<0.05 M-W test vs. IA Vehicle (Day 40).

As seen in FIG. 26, Pro-Gly-CNP-37 treatment had modest effects on the osteophyte score at all doses and administration routes. As with the earlier stage osteoarthritis study described in Example 2, Pro-Gly-CNP-37 treatment resulted in reduced body weight change in treated animals (FIG. 27).

The present invention may be embodied in other specific forms without departing from the true scope of the invention. Any references to the "invention" are intended to refer to exemplary embodiments of the invention and should not be construed to refer to all embodiments of the invention unless the context otherwise requires. The described embodiments are to be considered in all respects only as illustrative and not restrictive; numerous variations and modifications will be apparent to those skilled in the art.

What is claimed is:

1. A method of treating osteoarthritis in a subject, comprising intraarticularly administering a composition comprising a C-type natriuretic peptide (CNP) variant to the subject at a dose of from 5 μg/kg to 800 μg/kg of the CNP variant, wherein the CNP variant is selected from the group consisting of:

PGQEHPNARKYKGANKKGLSKGCFGLKLDRIGSMSGLGC (SEQ ID NO: 1)
(Pro-Gly-CNP37);

GQEHPNARKYKGANKKGLSKGCFGLKLDRIGSMSGLGC (SEQ ID NO: 2)
(Gly-CNP37);

QEHPNARKYKGANKKGLSKGCFGLKLDRIGSNSGLGC (SEQ ID NO: 43)
[CNP-37(M32N)]

PQEHPNARKYKGANKKGLSKGCFGLKLDRIGSMSGLGC (SEQ ID NO: 44)
(Pro-CNP37);

MQEHPNARKYKGANKKGLSKGCFGLKLDRIGSMSGLGC (SEQ ID NO: 45)
(Met-CNP37);

GQEHPNARKYKGANKKGLSKGCFGLKLDRIGSNSGLGC (SEQ ID NO: 46)
[Gly-CN P-37(M32N)]; and

MGQEHPNARKYKGANKKGLSKGCFGLKLDRIGSMSGLGC (SEQ ID NO: 47)
(Met-Gly-CNP37).

2. The method of claim 1, wherein said method ameliorates a symptom of osteoarthritis in the subject.

3. The method of claim 1, wherein said method increases motor skills or mobility in the subject.

4. The method of claim 1, wherein said method inhibits degeneration of mobility in the subject.

5. The method of claim 1, wherein said method increases range of motion in an affected joint of the subject.

6. The method of claim 5, wherein the range of motion of an affected joint is determined by measuring hip flexion, hip extension, hip abduction, hip adduction, knee flexion, or knee extension.

7. The method of claim 1, wherein said method decreases stiffness in an affected joint of the subject.

8. The method of claim 1, wherein said method decreases synovial inflammation in the subject.

9. A method of increasing cartilage growth or slowing cartilage degeneration in a subject having osteoarthritis, comprising intraarticularly administering a composition comprising a C-type natriuretic peptide (CNP) variant to the subject at a dose of from 5 μg/kg to 800 μg/kg of the CNP variant, wherein the CNP variant is selected from the group consisting of:

PGQEHPNARKYKGANKKGLSKGCFGLKLDRIGSMSGLGC (SEQ ID NO: 1)
(Pro-Gly-CNP37);

GQEHPNARKYKGANKKGLSKGCFGLKLDRIGSMSGLGC (SEQ ID NO: 2)
(Gly-CNP37);

QEHPNARKYKGANKKGLSKGCFGLKLDRIGSNSGLGC (SEQ ID NO: 43)
[CNP-37(M32N)]

PQEHPNARKYKGANKKGLSKGCFGLKLDRIGSMSGLGC (SEQ ID NO: 44)
(Pro-CNP37);

MQEHPNARKYKGANKKGLSKGCFGLKLDRIGSMSGLGC (SEQ ID NO: 45)
(Met-CNP37);

GQEHPNARKYKGANKKGLSKGCFGLKLDRIGSNSGLGC (SEQ ID NO: 46)
[Gly-CN P-37(M32N)]; and

MGQEHPNARKYKGANKKGLSKGCFGLKLDRIGSMSGLGC (SEQ ID NO: 47)
(Met-Gly-CNP37).

10. The method of claim 9, wherein the increase in cartilage growth or slowing of cartilage degeneration is observed in a joint of the subject.

11. A method of reducing osteophyte growth in a subject having osteoarthritis or having an injury or trauma in a joint, comprising intraarticularly administering a composition comprising a C-type natriuretic peptide (CNP) variant to the subject at a dose of from 5 g/kg to 800 μg/kg of the CNP variant, wherein the CNP variant is selected from the group consisting of:

PGQEHPNARKYKGANKKGLSKGCFGLKLDRIGSMSGLGC (SEQ ID NO: 1)
(Pro-Gly-CNP37);

GQEHPNARKYKGANKKGLSKGCFGLKLDRIGSMSGLGC (SEQ ID NO: 2)
(Gly-CNP37);

QEHPNARKYKGANKKGLSKGCFGLKLDRIGSNSGLGC (SEQ ID NO: 43)
[CNP-37(M32N)]

PQEHPNARKYKGANKKGLSKGCFGLKLDRIGSMSGLGC (SEQ ID NO: 44)
(Pro-CNP37);

MQEHPNARKYKGANKKGLSKGCFGLKLDRIGSMSGLGC (SEQ ID NO: 45)
(Met-CNP37);

GQEHPNARKYKGANKKGLSKGCFGLKLDRIGSNSGLGC (SEQ ID NO: 46)
[Gly-CN P-37(M32N)]; and

MGQEHPNARKYKGANKKGLSKGCFGLKLDRIGSMSGLGC (SEQ ID NO: 47)
(Met-Gly-CNP37).

12. The method of claim 11, wherein the subject has osteoarthritis.

13. The method of claim 12, wherein the osteoarthritis is primary or secondary osteoarthritis.

14. The method of claim 12, wherein the CNP variant is administered after cartilage degeneration has occurred.

15. The method of claim 11, wherein the subject has an injury or trauma in a joint, and wherein the CNP variant is administered within one month of the joint injury or trauma.

16. The method of claim 11, further comprising administration of a second agent.

17. The method of claim 11, wherein the subject is identified as having increased levels of at least one cartilage-associated biomarker.

18. The method of claim 17, wherein the at least one cartilage-associated biomarker is selected from the group consisting of CNP, cyclic guanosine monophosphate (cGMP), propeptides of collagen type II and fragments thereof, collagen type II and fragments thereof, osteocalcin, proliferating cell nuclear antigen (PCNA), propeptides of type I procollagen (PINP) and fragments thereof, collagen type I and fragments thereof, and aggrecan chondroitin sulfate.

* * * * *

SEQUENCE LISTING

```
<160> NUMBER OF SEQ ID NOS: 162

<210> SEQ ID NO 1
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Pro-Gly-CNP37
<220> FEATURE:
<221> NAME/KEY: MISC_FEATURE
<223> OTHER INFORMATION: Pro-Gly-wtCNP37

<400> SEQUENCE: 1

Pro Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 2
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Gly-CNP-37
<220> FEATURE:
<221> NAME/KEY: MISC_FEATURE
<223> OTHER INFORMATION: Gly-wtCNP37

<400> SEQUENCE: 2

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 3
<211> LENGTH: 54
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Gly-CNP53
```

```
<220> FEATURE:
<221> NAME/KEY: MISC_FEATURE
<223> OTHER INFORMATION: Gly-wtCNP53

<400> SEQUENCE: 3

Gly Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 4
<211> LENGTH: 54
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Pro-CNP53
<220> FEATURE:
<221> NAME/KEY: MISC_FEATURE
<223> OTHER INFORMATION: Pro-wtCNP53

<400> SEQUENCE: 4

Pro Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 5
<211> LENGTH: 54
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Met-CNP53
<220> FEATURE:
<221> NAME/KEY: MISC_FEATURE
<223> OTHER INFORMATION: Met-wtCNP53

<400> SEQUENCE: 5

Met Asp Leu Arg Val Asp Thr Lys Ser Arg Ala Ala Trp Ala Arg Leu
1               5                   10                  15

Leu Gln Glu His Pro Asn Ala Arg Lys Tyr Lys Gly Ala Asn Lys Lys
            20                  25                  30

Gly Leu Ser Lys Gly Cys Phe Gly Leu Lys Leu Asp Arg Ile Gly Ser
        35                  40                  45

Met Ser Gly Leu Gly Cys
    50

<210> SEQ ID NO 6
<211> LENGTH: 53
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: MISC_FEATURE
<223> OTHER INFORMATION: CNP-53(M48N)

<400> SEQUENCE: 6

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Asn
        35                  40                  45

Ser Gly Leu Gly Cys
    50

<210> SEQ ID NO 7
<211> LENGTH: 52
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-52

<400> SEQUENCE: 7

Leu Arg Val Asp Thr Lys Ser Arg Ala Ala Trp Ala Arg Leu Leu Gln
1               5                   10                  15

Glu His Pro Asn Ala Arg Lys Tyr Lys Gly Ala Asn Lys Lys Gly Leu
            20                  25                  30

Ser Lys Gly Cys Phe Gly Leu Lys Leu Asp Arg Ile Gly Ser Met Ser
        35                  40                  45

Gly Leu Gly Cys
    50

<210> SEQ ID NO 8
<211> LENGTH: 51
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-51

<400> SEQUENCE: 8

Arg Val Asp Thr Lys Ser Arg Ala Ala Trp Ala Arg Leu Leu Gln Glu
1               5                   10                  15

His Pro Asn Ala Arg Lys Tyr Lys Gly Ala Asn Lys Lys Gly Leu Ser
            20                  25                  30

Lys Gly Cys Phe Gly Leu Lys Leu Asp Arg Ile Gly Ser Met Ser Gly
        35                  40                  45

Leu Gly Cys
    50

<210> SEQ ID NO 9
<211> LENGTH: 50
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
```

<223> OTHER INFORMATION: CNP-50

<400> SEQUENCE: 9

Val Asp Thr Lys Ser Arg Ala Ala Trp Ala Arg Leu Leu Gln Glu His
1               5                   10                  15

Pro Asn Ala Arg Lys Tyr Lys Gly Ala Asn Lys Lys Gly Leu Ser Lys
            20                  25                  30

Gly Cys Phe Gly Leu Lys Leu Asp Arg Ile Gly Ser Met Ser Gly Leu
        35                  40                  45

Gly Cys
    50

<210> SEQ ID NO 10
<211> LENGTH: 49
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-49

<400> SEQUENCE: 10

Asp Thr Lys Ser Arg Ala Ala Trp Ala Arg Leu Leu Gln Glu His Pro
1               5                   10                  15

Asn Ala Arg Lys Tyr Lys Gly Ala Asn Lys Lys Gly Leu Ser Lys Gly
            20                  25                  30

Cys Phe Gly Leu Lys Leu Asp Arg Ile Gly Ser Met Ser Gly Leu Gly
        35                  40                  45

Cys

<210> SEQ ID NO 11
<211> LENGTH: 48
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-48

<400> SEQUENCE: 11

Thr Lys Ser Arg Ala Ala Trp Ala Arg Leu Leu Gln Glu His Pro Asn
1               5                   10                  15

Ala Arg Lys Tyr Lys Gly Ala Asn Lys Lys Gly Leu Ser Lys Gly Cys
            20                  25                  30

Phe Gly Leu Lys Leu Asp Arg Ile Gly Ser Met Ser Gly Leu Gly Cys
        35                  40                  45

<210> SEQ ID NO 12
<211> LENGTH: 47
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-47

<400> SEQUENCE: 12

Lys Ser Arg Ala Ala Trp Ala Arg Leu Leu Gln Glu His Pro Asn Ala
1               5                   10                  15

Arg Lys Tyr Lys Gly Ala Asn Lys Lys Gly Leu Ser Lys Gly Cys Phe

```
                    20                  25                  30

Gly Leu Lys Leu Asp Arg Ile Gly Ser Met Ser Gly Leu Gly Cys
        35                  40                  45

<210> SEQ ID NO 13
<211> LENGTH: 46
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-46

<400> SEQUENCE: 13

Ser Arg Ala Ala Trp Ala Arg Leu Leu Gln Glu His Pro Asn Ala Arg
1               5                   10                  15

Lys Tyr Lys Gly Ala Asn Lys Lys Gly Leu Ser Lys Gly Cys Phe Gly
            20                  25                  30

Leu Lys Leu Asp Arg Ile Gly Ser Met Ser Gly Leu Gly Cys
        35                  40                  45

<210> SEQ ID NO 14
<211> LENGTH: 45
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-45

<400> SEQUENCE: 14

Arg Ala Ala Trp Ala Arg Leu Leu Gln Glu His Pro Asn Ala Arg Lys
1               5                   10                  15

Tyr Lys Gly Ala Asn Lys Lys Gly Leu Ser Lys Gly Cys Phe Gly Leu
            20                  25                  30

Lys Leu Asp Arg Ile Gly Ser Met Ser Gly Leu Gly Cys
        35                  40                  45

<210> SEQ ID NO 15
<211> LENGTH: 44
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-44

<400> SEQUENCE: 15

Ala Ala Trp Ala Arg Leu Leu Gln Glu His Pro Asn Ala Arg Lys Tyr
1               5                   10                  15

Lys Gly Ala Asn Lys Lys Gly Leu Ser Lys Gly Cys Phe Gly Leu Lys
            20                  25                  30

Leu Asp Arg Ile Gly Ser Met Ser Gly Leu Gly Cys
        35                  40

<210> SEQ ID NO 16
<211> LENGTH: 43
<212> TYPE: PRT
<213> ORGANISM: Artificial Sequence
<220> FEATURE:
<223> OTHER INFORMATION: Synthetic polypeptide
<220> FEATURE:
```

<221> NAME/KEY: MISC_FEATURE
<223> OTHER INFORMATION: CNP-43

<400> SEQUENCE: 16

Ala Trp Ala Arg Leu Leu Gln Glu His Pro Asn Ala Arg Lys Tyr Lys
1               5                   10                  15

Gly Ala Asn Lys Lys Gly Leu Ser Lys Gly Cys Phe Gly Leu Lys Leu
            20                  25                  30

Asp Arg Ile Gly Ser Met Ser Gly Leu Gly Cys
        35                  40

<210> SEQ ID NO 17
<211> LENGTH: 42
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-42

<400> SEQUENCE: 17

Trp Ala Arg Leu Leu Gln Glu His Pro Asn Ala Arg Lys Tyr Lys Gly
1               5                   10                  15

Ala Asn Lys Lys Gly Leu Ser Lys Gly Cys Phe Gly Leu Lys Leu Asp
            20                  25                  30

Arg Ile Gly Ser Met Ser Gly Leu Gly Cys
        35                  40

<210> SEQ ID NO 18
<211> LENGTH: 41
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-41

<400> SEQUENCE: 18

Ala Arg Leu Leu Gln Glu His Pro Asn Ala Arg Lys Tyr Lys Gly Ala
1               5                   10                  15

Asn Lys Lys Gly Leu Ser Lys Gly Cys Phe Gly Leu Lys Leu Asp Arg
            20                  25                  30

Ile Gly Ser Met Ser Gly Leu Gly Cys
        35                  40

<210> SEQ ID NO 19
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-40

<400> SEQUENCE: 19

Arg Leu Leu Gln Glu His Pro Asn Ala Arg Lys Tyr Lys Gly Ala Asn
1               5                   10                  15

Lys Lys Gly Leu Ser Lys Gly Cys Phe Gly Leu Lys Leu Asp Arg Ile
            20                  25                  30

Gly Ser Met Ser Gly Leu Gly Cys
        35                  40

<210> SEQ ID NO 20
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-39

<400> SEQUENCE: 20

```
Leu Leu Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35
```

<210> SEQ ID NO 21
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-38

<400> SEQUENCE: 21

```
Leu Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35
```

<210> SEQ ID NO 22
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-37
<220> FEATURE:
<221> NAME/KEY: MISC_FEATURE
<223> OTHER INFORMATION: wtCNP37
<220> FEATURE:
<221> NAME/KEY: MISC_FEATURE
<223> OTHER INFORMATION: Analog BL

<400> SEQUENCE: 22

```
Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Met
            20                  25                  30

Ser Gly Leu Gly Cys
        35
```

<210> SEQ ID NO 23
<211> LENGTH: 36
<212> TYPE: PRT
<213> ORGANISM: Artificial Sequence
<220> FEATURE:

<223> OTHER INFORMATION: Synthetic polypeptide
<220> FEATURE:
<221> NAME/KEY: MISC_FEATURE
<223> OTHER INFORMATION: CNP-36

<400> SEQUENCE: 23

Glu His Pro Asn Ala Arg Lys Tyr Lys Gly Ala Asn Lys Lys Gly Leu
1               5                   10                  15

Ser Lys Gly Cys Phe Gly Leu Lys Leu Asp Arg Ile Gly Ser Met Ser
            20                  25                  30

Gly Leu Gly Cys
            35

<210> SEQ ID NO 24
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-35

<400> SEQUENCE: 24

His Pro Asn Ala Arg Lys Tyr Lys Gly Ala Asn Lys Lys Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 25
<211> LENGTH: 34
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-34
<220> FEATURE:
<221> NAME/KEY: MISC_FEATURE
<223> OTHER INFORMATION: wtCNP34

<400> SEQUENCE: 25

Pro Asn Ala Arg Lys Tyr Lys Gly Ala Asn Lys Lys Gly Leu Ser Lys
1               5                   10                  15

Gly Cys Phe Gly Leu Lys Leu Asp Arg Ile Gly Ser Met Ser Gly Leu
            20                  25                  30

Gly Cys

<210> SEQ ID NO 26
<211> LENGTH: 33
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-33

<400> SEQUENCE: 26

Asn Ala Arg Lys Tyr Lys Gly Ala Asn Lys Lys Gly Leu Ser Lys Gly
1               5                   10                  15

Cys Phe Gly Leu Lys Leu Asp Arg Ile Gly Ser Met Ser Gly Leu Gly

```
            20                  25                  30

Cys

<210> SEQ ID NO 27
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-32

<400> SEQUENCE: 27

Ala Arg Lys Tyr Lys Gly Ala Asn Lys Lys Gly Leu Ser Lys Gly Cys
1               5                   10                  15

Phe Gly Leu Lys Leu Asp Arg Ile Gly Ser Met Ser Gly Leu Gly Cys
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-31

<400> SEQUENCE: 28

Arg Lys Tyr Lys Gly Ala Asn Lys Lys Gly Leu Ser Lys Gly Cys Phe
1               5                   10                  15

Gly Leu Lys Leu Asp Arg Ile Gly Ser Met Ser Gly Leu Gly Cys
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-30

<400> SEQUENCE: 29

Lys Tyr Lys Gly Ala Asn Lys Lys Gly Leu Ser Lys Gly Cys Phe Gly
1               5                   10                  15

Leu Lys Leu Asp Arg Ile Gly Ser Met Ser Gly Leu Gly Cys
            20                  25                  30

<210> SEQ ID NO 30
<211> LENGTH: 29
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-29

<400> SEQUENCE: 30

Tyr Lys Gly Ala Asn Lys Lys Gly Leu Ser Lys Gly Cys Phe Gly Leu
1               5                   10                  15

Lys Leu Asp Arg Ile Gly Ser Met Ser Gly Leu Gly Cys
            20                  25
```

```
<210> SEQ ID NO 31
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-28

<400> SEQUENCE: 31

Lys Gly Ala Asn Lys Lys Gly Leu Ser Lys Gly Cys Phe Gly Leu Lys
1               5                   10                  15

Leu Asp Arg Ile Gly Ser Met Ser Gly Leu Gly Cys
            20                  25

<210> SEQ ID NO 32
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-27

<400> SEQUENCE: 32

Gly Ala Asn Lys Lys Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 33
<211> LENGTH: 26
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-26

<400> SEQUENCE: 33

Ala Asn Lys Lys Gly Leu Ser Lys Gly Cys Phe Gly Leu Lys Leu Asp
1               5                   10                  15

Arg Ile Gly Ser Met Ser Gly Leu Gly Cys
            20                  25

<210> SEQ ID NO 34
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-25

<400> SEQUENCE: 34

Asn Lys Lys Gly Leu Ser Lys Gly Cys Phe Gly Leu Lys Leu Asp Arg
1               5                   10                  15

Ile Gly Ser Met Ser Gly Leu Gly Cys
            20                  25

<210> SEQ ID NO 35
```

```
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-24

<400> SEQUENCE: 35

Lys Lys Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 36
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-23

<400> SEQUENCE: 36

Lys Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 37
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-22

<400> SEQUENCE: 37

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 38
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-21

<400> SEQUENCE: 38

Leu Ser Lys Gly Cys Phe Gly Leu Lys Leu Asp Arg Ile Gly Ser Met
1               5                   10                  15

Ser Gly Leu Gly Cys
            20

<210> SEQ ID NO 39
<211> LENGTH: 20
<212> TYPE: PRT
<213> ORGANISM: Artificial Sequence
```

```
<220> FEATURE:
<223> OTHER INFORMATION: Synthetic polypeptide
<220> FEATURE:
<221> NAME/KEY: MISC_FEATURE
<223> OTHER INFORMATION: CNP-20

<400> SEQUENCE: 39

Ser Lys Gly Cys Phe Gly Leu Lys Leu Asp Arg Ile Gly Ser Met Ser
1               5                   10                  15

Gly Leu Gly Cys
            20

<210> SEQ ID NO 40
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-19

<400> SEQUENCE: 40

Lys Gly Cys Phe Gly Leu Lys Leu Asp Arg Ile Gly Ser Met Ser Gly
1               5                   10                  15

Leu Gly Cys

<210> SEQ ID NO 41
<211> LENGTH: 18
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-18

<400> SEQUENCE: 41

Gly Cys Phe Gly Leu Lys Leu Asp Arg Ile Gly Ser Met Ser Gly Leu
1               5                   10                  15

Gly Cys

<210> SEQ ID NO 42
<211> LENGTH: 17
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-17

<400> SEQUENCE: 42

Cys Phe Gly Leu Lys Leu Asp Arg Ile Gly Ser Met Ser Gly Leu Gly
1               5                   10                  15

Cys

<210> SEQ ID NO 43
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-37(M32N)
```

```
<400> SEQUENCE: 43

Gln Glu His Pro Asn Ala Arg Lys Tyr Lys Gly Ala Asn Lys Lys Gly
1               5                   10                  15

Leu Ser Lys Gly Cys Phe Gly Leu Lys Leu Asp Arg Ile Gly Ser Asn
                20                  25                  30

Ser Gly Leu Gly Cys
        35

<210> SEQ ID NO 44
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Pro-CNP-37
<220> FEATURE:
<221> NAME/KEY: MISC_FEATURE
<223> OTHER INFORMATION: Pro-wtCNP37

<400> SEQUENCE: 44

Pro Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
                20                  25                  30

Met Ser Gly Leu Gly Cys
        35

<210> SEQ ID NO 45
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Met-CNP-37
<220> FEATURE:
<221> NAME/KEY: MISC_FEATURE
<223> OTHER INFORMATION: Met-wtCNP37

<400> SEQUENCE: 45

Met Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
                20                  25                  30

Met Ser Gly Leu Gly Cys
        35

<210> SEQ ID NO 46
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Gly-CNP-37(M32N)

<400> SEQUENCE: 46

Gly Gln Glu His Pro Asn Ala Arg Lys Tyr Lys Gly Ala Asn Lys Lys
1               5                   10                  15

Gly Leu Ser Lys Gly Cys Phe Gly Leu Lys Leu Asp Arg Ile Gly Ser
                20                  25                  30
```

Asn Ser Gly Leu Gly Cys
          35

<210> SEQ ID NO 47
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Met-Gly-CNP-37
<220> FEATURE:
<221> NAME/KEY: MISC_FEATURE
<223> OTHER INFORMATION: Met-Gly-wtCNP37

<400> SEQUENCE: 47

Met Gly Gln Glu His Pro Asn Ala Arg Lys Tyr Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
          35

<210> SEQ ID NO 48
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: HSA-CNP-27
<220> FEATURE:
<221> NAME/KEY: MISC_FEATURE
<223> OTHER INFORMATION: HSA-wtCNP27

<400> SEQUENCE: 48

Gly His Lys Ser Glu Val Ala His Arg Phe Lys Gly Ala Asn Lys Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
          35

<210> SEQ ID NO 49
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: HSA-CNP-27(M22N)

<400> SEQUENCE: 49

Gly His Lys Ser Glu Val Ala His Arg Phe Lys Gly Ala Asn Lys Lys
1               5                   10                  15

Gly Leu Ser Lys Gly Cys Phe Gly Leu Lys Leu Asp Arg Ile Gly Ser
            20                  25                  30

Asn Ser Gly Leu Gly Cys
          35

<210> SEQ ID NO 50
<211> LENGTH: 39

<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Pro-HSA-CNP-27
<220> FEATURE:
<221> NAME/KEY: MISC_FEATURE
<223> OTHER INFORMATION: Pro-HSA-wtCNP27

<400> SEQUENCE: 50

Pro Gly His Lys Ser Glu Val Ala His Arg Phe Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 51
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Met-HSA-CNP-27

<400> SEQUENCE: 51

Met Gly His Lys Ser Glu Val Ala His Arg Phe Lys Gly Ala Asn Lys
1               5                   10                  15

Lys Gly Leu Ser Lys Gly Cys Phe Gly Leu Lys Leu Asp Arg Ile Gly
            20                  25                  30

Ser Met Ser Gly Leu Gly Cys
        35

<210> SEQ ID NO 52
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-27(K4,5,9R)
<220> FEATURE:
<221> NAME/KEY: MISC_FEATURE
<223> OTHER INFORMATION: Analog AY

<400> SEQUENCE: 52

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 53
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: CNP-27(K4,5,9R, M22N)

<400> SEQUENCE: 53

```
Gly Ala Asn Arg Arg Gly Leu Ser Arg Gly Cys Phe Gly Leu Lys Leu
1               5                   10                  15

Asp Arg Ile Gly Ser Asn Ser Gly Leu Gly Cys
            20                  25
```

<210> SEQ ID NO 54
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Pro-CNP-27(K4,5,9R)

<400> SEQUENCE: 54

```
Pro Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
                20                  25
```

<210> SEQ ID NO 55
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Met-CNP-27(K4,5,9R)

<400> SEQUENCE: 55

```
Met Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
                20                  25
```

<210> SEQ ID NO 56
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEG1K-CNP-27(K4,5,9R)
<220> FEATURE:
<221> NAME/KEY: MISC_FEATURE
<222> LOCATION: (1)..(1)
<223> OTHER INFORMATION: PEG1K

<400> SEQUENCE: 56

```
Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25
```

<210> SEQ ID NO 57
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEG1K-CNP-27(K4,5,9R, M22N)
<220> FEATURE:
<221> NAME/KEY: MISC_FEATURE

```
<222> LOCATION: (1)..(1)
<223> OTHER INFORMATION: PEG1K

<400> SEQUENCE: 57

Gly Ala Asn Arg Arg Gly Leu Ser Arg Gly Cys Phe Gly Leu Lys Leu
1               5                   10                  15

Asp Arg Ile Gly Ser Asn Ser Gly Leu Gly Cys
            20                  25

<210> SEQ ID NO 58
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEG1K-Pro-CNP-27(K4,5,9R)
<220> FEATURE:
<221> NAME/KEY: MISC_FEATURE
<222> LOCATION: (1)..(1)
<223> OTHER INFORMATION: PEG1

<400> SEQUENCE: 58

Pro Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
                20                  25

<210> SEQ ID NO 59
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEG1K-Met-CNP-27(K4,5,9R)
<220> FEATURE:
<221> NAME/KEY: MISC_FEATURE
<222> LOCATION: (1)..(1)
<223> OTHER INFORMATION: PEG1K

<400> SEQUENCE: 59

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 60
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-CNP-27(K4,5,9R)
<220> FEATURE:
<221> NAME/KEY: MISC_FEATURE
<222> LOCATION: (1)..(1)
<223> OTHER INFORMATION: PEO12

<400> SEQUENCE: 60

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25
```

<210> SEQ ID NO 61
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-CNP-27(K4,5,9R, M22N)
<220> FEATURE:
<221> NAME/KEY: MISC_FEATURE
<222> LOCATION: (1)..(1)
<223> OTHER INFORMATION: PEO12

<400> SEQUENCE: 61

Gly Ala Asn Arg Arg Gly Leu Ser Arg Gly Cys Phe Gly Leu Lys Leu
1               5                   10                  15

Asp Arg Ile Gly Ser Asn Ser Gly Leu Gly Cys
            20                  25

<210> SEQ ID NO 62
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-Pro-CNP-27(K4,5,9R)
<220> FEATURE:
<221> NAME/KEY: MISC_FEATURE
<222> LOCATION: (1)..(1)
<223> OTHER INFORMATION: PEO12

<400> SEQUENCE: 62

Pro Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
            20                  25

<210> SEQ ID NO 63
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-Met-CNP-27(K4,5,9R)
<220> FEATURE:
<221> NAME/KEY: MISC_FEATURE
<222> LOCATION: (1)..(1)
<223> OTHER INFORMATION: PEO12

<400> SEQUENCE: 63

Pro Glu Met Gly Ala Asn Arg Arg Gly Leu Ser Arg Gly Cys Phe Gly
1               5                   10                  15

Leu Lys Leu Asp Arg Ile Gly Ser Met Ser Gly Leu Gly Cys
            20                  25                  30

<210> SEQ ID NO 64
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-CNP-27(K4,5,9R)
<220> FEATURE:
<221> NAME/KEY: MISC_FEATURE
<222> LOCATION: (1)..(1)
<223> OTHER INFORMATION: PEO24

<400> SEQUENCE: 64

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 65
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-CNP-27(K4,5,9R, M22N)
<220> FEATURE:
<221> NAME/KEY: MISC_FEATURE
<222> LOCATION: (1)..(1)
<223> OTHER INFORMATION: PEO24

<400> SEQUENCE: 65

Gly Ala Asn Arg Arg Gly Leu Ser Arg Gly Cys Phe Gly Leu Lys Leu
1               5                   10                  15

Asp Arg Ile Gly Ser Asn Ser Gly Leu Gly Cys
            20                  25

<210> SEQ ID NO 66
<211> LENGTH: 28
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-Pro-CNP-27(K4,5,9R)
<220> FEATURE:
<221> NAME/KEY: MISC_FEATURE
<222> LOCATION: (1)..(1)
<223> OTHER INFORMATION: PEO24

<400> SEQUENCE: 66

Pro Gly Ala Asn Arg Arg Gly Leu Ser Arg Gly Cys Phe Gly Leu Lys
1               5                   10                  15

Leu Asp Arg Ile Gly Ser Met Ser Gly Leu Gly Cys
            20                  25

<210> SEQ ID NO 67
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-Met-CNP-27(K4,5,9R)
<220> FEATURE:
<221> NAME/KEY: MISC_FEATURE
<222> LOCATION: (1)..(1)
<223> OTHER INFORMATION: PEO24

<400> SEQUENCE: 67

Pro Glu Met Gly Ala Asn Arg Arg Gly Leu Ser Arg Gly Cys Phe Gly
1               5                   10                  15

```
Leu Lys Leu Asp Arg Ile Gly Ser Met Ser Gly Leu Gly Cys
            20                  25                  30

<210> SEQ ID NO 68
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CA

<400> SEQUENCE: 68

Ala Ala Trp Ala Arg Leu Leu Gln Glu His Pro Asn Ala Gly Leu Ser
1               5                   10                  15

Lys Gly Cys Phe Gly Leu Lys Leu Asp Arg Ile Gly Ser Met Ser Gly
            20                  25                  30

Leu Gly Cys
        35

<210> SEQ ID NO 69
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CB

<400> SEQUENCE: 69

Ala Ala Trp Ala Arg Leu Leu Gln Glu His Pro Asn Ala Arg Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 70
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CC

<400> SEQUENCE: 70

Asp Leu Arg Val Asp Thr Lys Ser Arg Ala Trp Ala Arg Gly Leu
1               5                   10                  15

Ser Lys Gly Cys Phe Gly Leu Lys Leu Asp Arg Ile Gly Ser Met Ser
            20                  25                  30

Gly Leu Gly Cys
        35

<210> SEQ ID NO 71
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
```

<223> OTHER INFORMATION: R-CNP22

<400> SEQUENCE: 71

Arg Gly Leu Ser Lys Gly Cys Phe Gly Leu Lys Leu Asp Arg Ile Gly
1               5                   10                  15

Ser Met Ser Gly Leu Gly Cys
            20

<210> SEQ ID NO 72
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: ER-CNP22

<400> SEQUENCE: 72

Glu Arg Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 73
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 73

Gly Ala Asn Gln Gln Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 74
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 74

Gly Ala Asn Arg Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 75
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 75

Gly Ala Asn Pro Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 76

```
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 76

Gly Ala Asn Ser Ser Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 77
<211> LENGTH: 32
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CD
<220> FEATURE:
<221> NAME/KEY: MISC_FEATURE
<223> OTHER INFORMATION: CNP17 having N-terminal and C-terminal tails
      derived from BNP

<400> SEQUENCE: 77

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 78
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CI
<220> FEATURE:
<221> NAME/KEY: MISC_FEATURE
<223> OTHER INFORMATION: GANPR-CNP22(K4R)

<400> SEQUENCE: 78

Gly Ala Asn Pro Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 79
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog AZ
<220> FEATURE:
<221> NAME/KEY: MISC_FEATURE
<223> OTHER INFORMATION: R-CNP22(K4R)

<400> SEQUENCE: 79

Arg Gly Leu Ser Arg Gly Cys Phe Gly Leu Lys Leu Asp Arg Ile Gly
1               5                   10                  15

Ser Met Ser Gly Leu Gly Cys
```

<210> SEQ ID NO 80
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog BA
<220> FEATURE:
<221> NAME/KEY: MISC_FEATURE
<223> OTHER INFORMATION: ER-CNP22(K4R)

<400> SEQUENCE: 80

Glu Arg Gly Leu Ser Arg Gly Cys Phe Gly Leu Lys Leu Asp Arg Ile
1               5                   10                  15

Gly Ser Met Ser Gly Leu Gly Cys
            20

<210> SEQ ID NO 81
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CH

<400> SEQUENCE: 81

Gly Ala Asn Gln Gln Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 82
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CG

<400> SEQUENCE: 82

Gly Ala Asn Ser Ser Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 83
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CQ
<220> FEATURE:
<221> NAME/KEY: MISC_FEATURE
<223> OTHER INFORMATION: histidine-rich glycoprotein (HRGP)
      fragment-CNP22 chimera

<400> SEQUENCE: 83

-continued

Gly His His Ser His Glu Gln His Pro His Gly Ala Asn Gln Gln Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 84
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CR
<220> FEATURE:
<221> NAME/KEY: MISC_FEATURE
<223> OTHER INFORMATION: HRGP fragment-CNP22 chimera

<400> SEQUENCE: 84

Gly Ala His His Pro His Glu His Asp Thr His Gly Ala Asn Gln Gln
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 85
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CX
<220> FEATURE:
<221> NAME/KEY: MISC_FEATURE
<223> OTHER INFORMATION: HRGP fragment-CNP22 chimera

<400> SEQUENCE: 85

Gly His His Ser His Glu Gln His Pro His Gly Ala Asn Pro Arg Gly
1               5                   10                  15

Leu Ser Lys Gly Cys Phe Gly Leu Lys Leu Asp Arg Ile Gly Ser Met
            20                  25                  30

Ser Gly Leu Gly Cys
        35

<210> SEQ ID NO 86
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CF
<220> FEATURE:
<221> NAME/KEY: MISC_FEATURE
<223> OTHER INFORMATION: IgG1(Fc) fragment- CNP22 chimera

<400> SEQUENCE: 86

Gly Gln Pro Arg Glu Pro Gln Val Tyr Thr Leu Pro Pro Ser Gly Leu
1               5                   10                  15

Ser Lys Gly Cys Phe Gly Leu Lys Leu Asp Arg Ile Gly Ser Met Ser

```
                20                  25                  30

Gly Leu Gly Cys
        35

<210> SEQ ID NO 87
<211> LENGTH: 39
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CY
<220> FEATURE:
<221> NAME/KEY: MISC_FEATURE
<223> OTHER INFORMATION: human serum albumin (HSA) fragment-CNP22
      chimera

<400> SEQUENCE: 87

Gly Gln His Lys Asp Asp Asn Pro Asn Leu Pro Arg Gly Ala Asn Pro
1               5                   10                  15

Arg Gly Leu Ser Lys Gly Cys Phe Gly Leu Lys Leu Asp Arg Ile Gly
                20                  25                  30

Ser Met Ser Gly Leu Gly Cys
        35

<210> SEQ ID NO 88
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: HSA fragment- CNP22 chimera
<220> FEATURE:
<221> NAME/KEY: MISC_FEATURE
<223> OTHER INFORMATION: Analog CE

<400> SEQUENCE: 88

Gly Glu Arg Ala Phe Lys Ala Trp Ala Val Ala Arg Leu Ser Gln Gly
1               5                   10                  15

Leu Ser Lys Gly Cys Phe Gly Leu Lys Leu Asp Arg Ile Gly Ser Met
                20                  25                  30

Ser Gly Leu Gly Cys
        35

<210> SEQ ID NO 89
<211> LENGTH: 35
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CZ
<220> FEATURE:
<221> NAME/KEY: MISC_FEATURE
<223> OTHER INFORMATION: osteocrin "NPR C inhibitor" fragment-CNP22
      chimera

<400> SEQUENCE: 89

Phe Gly Ile Pro Met Asp Arg Ile Gly Arg Asn Pro Arg Gly Leu Ser
1               5                   10                  15

Lys Gly Cys Phe Gly Leu Lys Leu Asp Arg Ile Gly Ser Met Ser Gly
                20                  25                  30
```

Leu Gly Cys
       35

<210> SEQ ID NO 90
<211> LENGTH: 40
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog DA
<220> FEATURE:
<221> NAME/KEY: MISC_FEATURE
<223> OTHER INFORMATION: FGF2 "heparin-binding domain" fragment-CNP22
      chimera

<400> SEQUENCE: 90

Gly Lys Arg Thr Gly Gln Tyr Lys Leu Gly Ser Lys Thr Gly Pro Gly
1               5                   10                  15

Pro Lys Gly Leu Ser Lys Gly Cys Phe Gly Leu Lys Leu Asp Arg Ile
            20                  25                  30

Gly Ser Met Ser Gly Leu Gly Cys
        35                  40

<210> SEQ ID NO 91
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CK
<220> FEATURE:
<221> NAME/KEY: MISC_FEATURE
<223> OTHER INFORMATION: IgG1(Fc) fragment-CNP22(K4R) chimera

<400> SEQUENCE: 91

Gly Gln Pro Arg Glu Pro Gln Val Tyr Thr Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 92
<211> LENGTH: 36
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CL
<220> FEATURE:
<221> NAME/KEY: MISC_FEATURE
<223> OTHER INFORMATION: HSA fragment-CNP22(K4R) chimera

<400> SEQUENCE: 92

Gly Val Pro Gln Val Ser Thr Ser Thr Gly Ala Asn Gln Gln Gly Leu
1               5                   10                  15

Ser Arg Gly Cys Phe Gly Leu Lys Leu Asp Arg Ile Gly Ser Met Ser
            20                  25                  30

Gly Leu Gly Cys
        35

<210> SEQ ID NO 93
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CM
<220> FEATURE:
<221> NAME/KEY: MISC_FEATURE
<223> OTHER INFORMATION: fibronectin fragment-CNP22(K4R) chimera

<400> SEQUENCE: 93

Gly Gln Pro Ser Ser Ser Gln Ser Thr Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 94
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CN
<220> FEATURE:
<221> NAME/KEY: MISC_FEATURE
<223> OTHER INFORMATION: fibrinogen fragment-CNP22(K4R) chimera

<400> SEQUENCE: 94

Gly Gln Thr His Ser Ser Gly Thr Gln Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 95
<211> LENGTH: 37
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CO
<220> FEATURE:
<221> NAME/KEY: MISC_FEATURE
<223> OTHER INFORMATION: fibrinogen fragment-CNP22(K4R) chimera

<400> SEQUENCE: 95

Gly Ser Thr Gly Gln Trp His Ser Glu Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 96
<211> LENGTH: 37
<212> TYPE: PRT

```
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CP
<220> FEATURE:
<221> NAME/KEY: MISC_FEATURE
<223> OTHER INFORMATION: zinc finger fragment-CNP22(K4R) chimera

<400> SEQUENCE: 96

Gly Ser Ser Ser Ser Ser Ser Ser Ser Gly Ala Asn Gln Gln Gly
1               5                   10                  15

Leu Ser Arg Gly Cys Phe Gly Leu Lys Leu Asp Arg Ile Gly Ser Met
            20                  25                  30

Ser Gly Leu Gly Cys
        35

<210> SEQ ID NO 97
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CS

<400> SEQUENCE: 97

Gly Gln Glu His Pro Asn Ala Arg Lys Tyr Lys Gly Ala Asn Pro Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 98
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CT

<400> SEQUENCE: 98

Gly Gln Glu His Pro Asn Ala Arg Lys Tyr Lys Gly Ala Asn Gln Lys
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 99
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CU

<400> SEQUENCE: 99

Gly Gln Glu His Pro Asn Ala Arg Lys Tyr Lys Gly Ala Asn Gln Gln
```

```
1               5                   10                  15
Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 100
<211> LENGTH: 38
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog CW

<400> SEQUENCE: 100

Gly Gln Glu His Pro Asn Ala Arg Lys Tyr Lys Gly Ala Asn Lys Pro
1               5                   10                  15

Gly Leu Ser Lys Gly Cys Phe Gly Leu Lys Leu Asp Arg Ile Gly Ser
            20                  25                  30

Met Ser Gly Leu Gly Cys
        35

<210> SEQ ID NO 101
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-GANRR-CNP22(K4R)
<220> FEATURE:
<221> NAME/KEY: MISC_FEATURE
<222> LOCATION: (1)..(1)
<223> OTHER INFORMATION: PEO12

<400> SEQUENCE: 101

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 102
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-GANRR-CNP22(K4R)
<220> FEATURE:
<221> NAME/KEY: MISC_FEATURE
<222> LOCATION: (1)..(1)
<223> OTHER INFORMATION: PEO24

<400> SEQUENCE: 102

Gly Ala Asn Arg Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 103
<211> LENGTH: 27
```

```
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-GANRR-CNP22
<220> FEATURE:
<221> NAME/KEY: MISC_FEATURE
<222> LOCATION: (1)..(1)
<223> OTHER INFORMATION: PEO24

<400> SEQUENCE: 103

Gly Ala Asn Arg Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 104
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-GANRR-CNP22
<220> FEATURE:
<221> NAME/KEY: MISC_FEATURE
<222> LOCATION: (1)..(1)
<223> OTHER INFORMATION: PEO12

<400> SEQUENCE: 104

Gly Ala Asn Arg Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 105
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-GANPR-CNP22(K4R)
<220> FEATURE:
<221> NAME/KEY: MISC_FEATURE
<222> LOCATION: (1)..(1)
<223> OTHER INFORMATION: PEO24

<400> SEQUENCE: 105

Gly Ala Asn Pro Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 106
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-GANPR-CNP22(K4R)
<220> FEATURE:
<221> NAME/KEY: MISC_FEATURE
<222> LOCATION: (1)..(1)
```

<223> OTHER INFORMATION: PEO12

<400> SEQUENCE: 106

Gly Ala Asn Pro Arg Gly Leu Ser Arg Gly Cys Phe Gly Leu Lys Leu
1               5                   10                  15

Asp Arg Ile Gly Ser Met Ser Gly Leu Gly Cys
            20                  25

<210> SEQ ID NO 107
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-GANPR-CNP22
<220> FEATURE:
<221> NAME/KEY: MISC_FEATURE
<222> LOCATION: (1)..(1)
<223> OTHER INFORMATION: PEO24

<400> SEQUENCE: 107

Gly Ala Asn Pro Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 108
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-GANPR-CNP22
<220> FEATURE:
<221> NAME/KEY: MISC_FEATURE
<222> LOCATION: (1)..(1)
<223> OTHER INFORMATION: PEO12

<400> SEQUENCE: 108

Gly Ala Asn Pro Arg Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 109
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-GANQQ-CNP22
<220> FEATURE:
<221> NAME/KEY: MISC_FEATURE
<222> LOCATION: (1)..(1)
<223> OTHER INFORMATION: PEO24

<400> SEQUENCE: 109

Gly Ala Asn Gln Gln Gly Leu Ser Lys Gly Cys Phe Gly Leu Lys Leu
1               5                   10                  15

Asp Arg Ile Gly Ser Met Ser Gly Leu Gly Cys
            20                  25

```
<210> SEQ ID NO 110
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-GANQQ-CNP22
<220> FEATURE:
<221> NAME/KEY: MISC_FEATURE
<222> LOCATION: (1)..(1)
<223> OTHER INFORMATION: PEO12

<400> SEQUENCE: 110

Gly Ala Asn Gln Gln Gly Leu Ser Lys Gly Cys Phe Gly Leu Lys Leu
1               5                   10                  15

Asp Arg Ile Gly Ser Met Ser Gly Leu Gly Cys
            20                  25

<210> SEQ ID NO 111
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-ER-CNP22(K4R)
<220> FEATURE:
<221> NAME/KEY: MISC_FEATURE
<222> LOCATION: (1)..(1)
<223> OTHER INFORMATION: PEO24

<400> SEQUENCE: 111

Glu Arg Gly Leu Ser Arg Gly Cys Phe Gly Leu Lys Leu Asp Arg Ile
1               5                   10                  15

Gly Ser Met Ser Gly Leu Gly Cys
            20

<210> SEQ ID NO 112
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-ER-CNP22(K4R)
<220> FEATURE:
<221> NAME/KEY: MISC_FEATURE
<222> LOCATION: (1)..(1)
<223> OTHER INFORMATION: PEO12

<400> SEQUENCE: 112

Glu Arg Gly Leu Ser Arg Gly Cys Phe Gly Leu Lys Leu Asp Arg Ile
1               5                   10                  15

Gly Ser Met Ser Gly Leu Gly Cys
            20

<210> SEQ ID NO 113
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-ER-CNP22
```

```
<220> FEATURE:
<221> NAME/KEY: MISC_FEATURE
<222> LOCATION: (1)..(1)
<223> OTHER INFORMATION: PEO24

<400> SEQUENCE: 113

Glu Arg Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 114
<211> LENGTH: 24
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-ER-CNP22
<220> FEATURE:
<221> NAME/KEY: MISC_FEATURE
<222> LOCATION: (1)..(1)
<223> OTHER INFORMATION: PEO12

<400> SEQUENCE: 114

Glu Arg Gly Leu Ser Lys Gly Cys Phe Gly Leu Lys Leu Asp Arg Ile
1               5                   10                  15

Gly Ser Met Ser Gly Leu Gly Cys
            20

<210> SEQ ID NO 115
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-R-CNP22(K4R)
<220> FEATURE:
<221> NAME/KEY: MISC_FEATURE
<222> LOCATION: (1)..(1)
<223> OTHER INFORMATION: PEO24

<400> SEQUENCE: 115

Arg Gly Leu Ser Arg Gly Cys Phe Gly Leu Lys Leu Asp Arg Ile Gly
1               5                   10                  15

Ser Met Ser Gly Leu Gly Cys
            20

<210> SEQ ID NO 116
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-R-CNP22(K4R)
<220> FEATURE:
<221> NAME/KEY: MISC_FEATURE
<222> LOCATION: (1)..(1)
<223> OTHER INFORMATION: PEO12

<400> SEQUENCE: 116

Arg Gly Leu Ser Arg Gly Cys Phe Gly Leu Lys Leu Asp Arg Ile Gly
1               5                   10                  15
```

```
Ser Met Ser Gly Leu Gly Cys
            20

<210> SEQ ID NO 117
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO24-R-CNP22
<220> FEATURE:
<221> NAME/KEY: MISC_FEATURE
<222> LOCATION: (1)..(1)
<223> OTHER INFORMATION: PEO24

<400> SEQUENCE: 117

Arg Gly Leu Ser Lys Gly Cys Phe Gly Leu Lys Leu Asp Arg Ile Gly
1               5                  10                  15

Ser Met Ser Gly Leu Gly Cys
            20

<210> SEQ ID NO 118
<211> LENGTH: 25
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: PEO12-R-CNP22
<220> FEATURE:
<221> NAME/KEY: MISC_FEATURE
<222> LOCATION: (1)..(1)
<223> OTHER INFORMATION: PEO12

<400> SEQUENCE: 118

Pro Glu Arg Gly Leu Ser Lys Gly Cys Phe Gly Leu Lys Leu Asp Arg
1               5                  10                  15

Ile Gly Ser Met Ser Gly Leu Gly Cys
            20                  25

<210> SEQ ID NO 119
<211> LENGTH: 27
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: GANRR-CNP22(K4R)

<400> SEQUENCE: 119

Gly Ala Asn Arg Arg Gly Leu Ser Arg Gly Cys Phe Gly Leu Lys Leu
1               5                  10                  15

Asp Arg Ile Gly Ser Met Ser Gly Leu Gly Cys
            20                  25

<210> SEQ ID NO 120
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N terminus may be modified by a synthetic
```

```
      bone-targeting compound or absent
<220> FEATURE:
<221> NAME/KEY: MISC_FEATURE
<222> LOCATION: (6)..(6)
<223> OTHER INFORMATION: Xaa is Cys, or any natural or unnatural Amino
      Acid or peptide bond isotere
<220> FEATURE:
<221> NAME/KEY: MISC_FEATURE
<222> LOCATION: (6)..(7)
<223> OTHER INFORMATION: Peptide Bond
<220> FEATURE:
<221> NAME/KEY: MISC_FEATURE
<222> LOCATION: (7)..(7)
<223> OTHER INFORMATION: Xaa is Phe, or any natural or unnatural Amino
      Acid or peptide bond isotere
<220> FEATURE:
<221> NAME/KEY: MISC_FEATURE
<222> LOCATION: (8)..(8)
<223> OTHER INFORMATION: Xaa is Gly or any natural or unnatural amino
      acid or petidomimetic
<220> FEATURE:
<221> NAME/KEY: MISC_FEATURE
<222> LOCATION: (22)..(22)
<223> OTHER INFORMATION: C terminus may be modified by a synthetic
      bone-targeting compound or absent

<400> SEQUENCE: 120

Gly Leu Ser Lys Gly Xaa Xaa Xaa Leu Lys Leu Asp Arg Ile Gly Ser
1               5                   10                  15

Met Ser Gly Leu Gly Cys
            20

<210> SEQ ID NO 121
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog A
<220> FEATURE:
<221> NAME/KEY: MOD_RES
<222> LOCATION: (6)..(6)
<223> OTHER INFORMATION: CH2NH

<400> SEQUENCE: 121

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 122
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog B
<220> FEATURE:
<221> NAME/KEY: MOD_RES
<222> LOCATION: (6)..(6)
<223> OTHER INFORMATION: N-Methyl-Phe

<400> SEQUENCE: 122

Gly Leu Ser Lys Gly Cys Gly Leu Lys Leu Asp Arg Ile Gly Ser Met
1               5                   10                  15

Ser Gly Leu Gly Cys
            20
```

```
<210> SEQ ID NO 123
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog E
<220> FEATURE:
<221> NAME/KEY: MOD_RES
<222> LOCATION: (6)..(6)
<223> OTHER INFORMATION: D-Phe

<400> SEQUENCE: 123

Gly Leu Ser Lys Gly Cys Gly Leu Lys Leu Asp Arg Ile Gly Ser Met
1               5                   10                  15

Ser Gly Leu Gly Cys
            20

<210> SEQ ID NO 124
<211> LENGTH: 23
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog F
<220> FEATURE:
<221> NAME/KEY: MOD_RES
<222> LOCATION: (7)..(7)
<223> OTHER INFORMATION: tBu-Gly

<400> SEQUENCE: 124

Gly Leu Ser Lys Gly Cys Phe Leu Tyr Leu Lys Leu Asp Arg Ile Gly
1               5                   10                  15

Ser Met Ser Gly Leu Gly Cys
            20

<210> SEQ ID NO 125
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<223> OTHER INFORMATION: Analog G
<220> FEATURE:
<221> NAME/KEY: MOD_RES
<222> LOCATION: (6)..(6)
<223> OTHER INFORMATION: 3-Cl-Phe

<400> SEQUENCE: 125

Gly Leu Ser Lys Gly Cys Gly Leu Lys Leu Asp Arg Ile Gly Ser Met
1               5                   10                  15

Ser Gly Leu Gly Cys
            20

<210> SEQ ID NO 126
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
```

```
<223> OTHER INFORMATION: Analog H
<220> FEATURE:
<221> NAME/KEY: MOD_RES
<222> LOCATION: (6)..(6)
<223> OTHER INFORMATION: NHCH2CH(Ph)CO

<400> SEQUENCE: 126

Gly Leu Ser Lys Gly Cys Gly Leu Lys Leu Asp Arg Ile Gly Ser Met
1               5                   10                  15

Ser Gly Leu Gly Cys
            20

<210> SEQ ID NO 127
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N terminus may be modified by a synthetic
      bone-targeting compound or absent
<220> FEATURE:
<221> NAME/KEY: MISC_FEATURE
<222> LOCATION: (4)..(4)
<223> OTHER INFORMATION: Xaa is any natural or unnatural Amino Acid or
      peptidomimetic that does not have a reactive primary amine on a
      side chain
<220> FEATURE:
<221> NAME/KEY: MISC_FEATURE
<222> LOCATION: (6)..(6)
<223> OTHER INFORMATION: Xaa is Cys or peptide-bond isosteres
<220> FEATURE:
<221> NAME/KEY: MISC_FEATURE
<222> LOCATION: (6)..(7)
<223> OTHER INFORMATION: Peptide bond
<220> FEATURE:
<221> NAME/KEY: MISC_FEATURE
<222> LOCATION: (7)..(7)
<223> OTHER INFORMATION: Xaa is L-Phe; D-Phe; 3-amino-2-phenylpropionic
      acid; or N-alkylated derivatives of Phe
<220> FEATURE:
<221> NAME/KEY: MISC_FEATURE
<222> LOCATION: (8)..(8)
<223> OTHER INFORMATION: Xaa is Gly, tert-butyl-Gly (tBu-Gly), Thr, Ser,
      Val, or Asn
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa is natural or unnatural amino acid or
      peptidomimetic that does not have a reactive primary amine on a
      side chain
<220> FEATURE:
<221> NAME/KEY: MISC_FEATURE
<222> LOCATION: (11)..(11)
<223> OTHER INFORMATION: Xaa is Leu or peptide-bond isosteres
<220> FEATURE:
<221> NAME/KEY: MISC_FEATURE
<222> LOCATION: (12)..(12)
<223> OTHER INFORMATION: Xaa is Ile, tBu-Gly, or peptide-bond isosteres
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: Xaa is Met, Val, Asn, beta-Cl-Ala,
      2-aminobutyric acid (Abu), or 2-amino-isobutyric acid (Aib)
<220> FEATURE:
<221> NAME/KEY: MISC_FEATURE
```

```
<222> LOCATION: (20)..(20)
<223> OTHER INFORMATION: Xaa is Leu, norleucine (Nle), homoleucine
      (Hleu), Val, tert-butyl-Ala (tBu-Ala), Ser, Thr, Arg, or
      peptide-bond isosteres
<220> FEATURE:
<221> NAME/KEY: MISC_FEATURE
<222> LOCATION: (22)..(22)
<223> OTHER INFORMATION: C terminus may be modified by a synthetic
      bone-targeting compound or absent

<400> SEQUENCE: 127

Gly Leu Ser Xaa Gly Xaa Xaa Xaa Xaa Xaa Xaa Asp Arg Xaa Gly Ser
1               5                   10                  15

Xaa Ser Gly Xaa Gly Cys
            20

<210> SEQ ID NO 128
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(1)
<223> OTHER INFORMATION: N terminus may be modified by a synthetic
      bone-targeting compound or absent
<220> FEATURE:
<221> NAME/KEY: MISC_FEATURE
<222> LOCATION: (4)..(4)
<223> OTHER INFORMATION: Xaa is Lys, a conservative amino acid
      substitution, any natural or unnatural amino acid or
      peptidomimetic that does not have a reactive primary amine on a
      side chain
<220> FEATURE:
<221> NAME/KEY: MISC_FEATURE
<222> LOCATION: (6)..(6)
<223> OTHER INFORMATION: Xaa is Cys or peptide bond isoteres
<220> FEATURE:
<221> NAME/KEY: MISC_FEATURE
<222> LOCATION: (6)..(7)
<223> OTHER INFORMATION: Peptide Bond
<220> FEATURE:
<221> NAME/KEY: MISC_FEATURE
<222> LOCATION: (7)..(7)
<223> OTHER INFORMATION: Xaa is L-Phe; D-Phe; 3-amino-2-phenylpropionic
      acid; N-alkylated derivatives of Phe
<220> FEATURE:
<221> NAME/KEY: MISC_FEATURE
<222> LOCATION: (8)..(8)
<223> OTHER INFORMATION: Xaa is Gly, tert-butyl-Gly, Thr, Ser, Val, or
      Asn
<220> FEATURE:
<221> NAME/KEY: MISC_FEATURE
<222> LOCATION: (9)..(9)
<223> OTHER INFORMATION: Xaa is Leu, Ser, Thr, or peptide bond isosteres
<220> FEATURE:
<221> NAME/KEY: MISC_FEATURE
<222> LOCATION: (10)..(10)
<223> OTHER INFORMATION: Xaa is Lys, Arg, Gly, 6-hydroxy-norleucine,
      citrulline (Cit), Gln, or Ser
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: MISC_FEATURE
<222> LOCATION: (14)..(14)
<223> OTHER INFORMATION: Xaa is Ile, tert-butyl-Gly (tBu-Gly), Asn, or
      peptide bond isosteres
<220> FEATURE:
<221> NAME/KEY: MISC_FEATURE
<222> LOCATION: (15)..(15)
<223> OTHER INFORMATION: Xaa is Gly, Arg, Ser, or Asn
<220> FEATURE:
<221> NAME/KEY: MISC_FEATURE
```

```
<222> LOCATION: (17)..(17)
<223> OTHER INFORMATION: Xaa is Met, Val, Asn, beta-Cl-Ala,
      2-aminobutyric acid (Abu), or 2-amino-isobutyric acid (Aib)
<220> FEATURE:
<221> NAME/KEY: MISC_FEATURE
<222> LOCATION: (20)..(20)
<223> OTHER INFORMATION: Xaa is Leu, norleucine (Nle), homoleucine
      (Hleu), Val, tert-butyl-Ala (tBu-Ala), Arg, Thr, Ser, and peptide
      bond isosteres
<220> FEATURE:
<221> NAME/KEY: MISC_FEATURE
<222> LOCATION: (22)..(22)
<223> OTHER INFORMATION: C terminus may be modified by a synthetic
      bone-targeting compound or absent

<400> SEQUENCE: 128

Gly Leu Ser Xaa Gly Xaa Xaa Xaa Xaa Xaa Xaa Asp Arg Xaa Xaa Ser
1               5                   10                  15

Xaa Ser Gly Xaa Gly Cys
            20

<210> SEQ ID NO 129
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N terminus is a natural or synthetic polymer
<220> FEATURE:
<221> NAME/KEY: MISC_FEATURE
<222> LOCATION: (17)..(17)
<223> OTHER INFORMATION: C terminus is a natural or synthetic polymer

<400> SEQUENCE: 129

Cys Phe Gly Leu Lys Leu Asp Arg Ile Gly Ser Met Ser Gly Leu Gly
1               5                   10                  15

Cys

<210> SEQ ID NO 130
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N terminus is a natural or synthetic polymer
<220> FEATURE:
<221> NAME/KEY: MISC_FEATURE
<222> LOCATION: (17)..(17)
<223> OTHER INFORMATION: C terminus is a natural or synthetic polymer

<400> SEQUENCE: 130

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 131
<211> LENGTH: 17
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
```

```
<222> LOCATION: (1)..(1)
<223> OTHER INFORMATION: N terminus is a synthetic or natural polymeric
      group, or a combination thereof
<220> FEATURE:
<221> NAME/KEY: MISC_FEATURE
<222> LOCATION: (4)..(4)
<223> OTHER INFORMATION: Xaa is Lys or a conservative amino acid
      substitution or any natural or unnatural amino acid or
      peptidomimetic that does not have a reactive primary amine on a
      side chain
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (17)..(17)
<223> OTHER INFORMATION: C terminus is a synthetic or natural polymeric
      group, or a combination thereof

<400> SEQUENCE: 131

Cys Phe Gly Leu Xaa Leu Asp Arg Ile Gly Ser Met Ser Gly Leu Gly
1               5                   10                  15

Cys

<210> SEQ ID NO 132
<211> LENGTH: 22
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: N terminus is a synthetic or natural polymeric
      group, or a combination thereof
<220> FEATURE:
<221> NAME/KEY: MISC_FEATURE
<222> LOCATION: (4)..(4)
<223> OTHER INFORMATION: Xaa is Lys or a conservative amino acid
      substitution or any natural or unnatural amino acid or
      peptidomimetic that does not have a reactive primary amine on a
      side chain
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (22)..(22)
<223> OTHER INFORMATION: C terminus is a synthetic or natural polymeric
      group, or a combination thereof

<400> SEQUENCE: 132

Gly Leu Ser Xaa Gly Cys Phe Gly Leu Xaa Leu Asp Arg Ile Gly Ser
1               5                   10                  15

Met Ser Gly Leu Gly Cys
            20

<210> SEQ ID NO 133
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 133

Gly Ala Asn Lys Lys
1               5

<210> SEQ ID NO 134
```

```
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 134

Gly Ala Asn Arg Arg
1               5

<210> SEQ ID NO 135
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 135

Gly Ala Asn Pro Arg
1               5

<210> SEQ ID NO 136
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 136

Gly Ala Asn Gln Gln
1               5

<210> SEQ ID NO 137
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 137

Gly Ala Asn Ser Ser
1               5

<210> SEQ ID NO 138
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 138

Gly Ala Asn Arg Gln
1               5

<210> SEQ ID NO 139
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 139

Gly Ala Asn Arg Met
1               5

<210> SEQ ID NO 140
<211> LENGTH: 5
```

```
<212> TYPE: PRT
<213> ORGANISM: Artificial Sequence
<220> FEATURE:
<223> OTHER INFORMATION: Synthetic Polypeptide

<400> SEQUENCE: 140

Gly Ala Asn Arg Thr
1               5

<210> SEQ ID NO 141
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 141

Gly Ala Asn Arg Ser
1               5

<210> SEQ ID NO 142
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 142

Ala Ala Trp Ala Arg Leu Leu Gln Glu His Pro Asn Ala
1               5                   10

<210> SEQ ID NO 143
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 143

Ala Ala Trp Ala Arg Leu Leu Gln Glu His Pro Asn Ala Arg
1               5                   10

<210> SEQ ID NO 144
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 144

Asp Leu Arg Val Asp Thr Lys Ser Arg Ala Ala Trp Ala Arg
1               5                   10

<210> SEQ ID NO 145
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 145

Gln Glu His Pro Asn Ala Arg Lys Tyr Lys Gly Ala Asn Lys Lys
1               5                   10                  15

<210> SEQ ID NO 146
<211> LENGTH: 15
<212> TYPE: PRT
```

```
<213> ORGANISM: Artificial Sequence
<220> FEATURE:
<223> OTHER INFORMATION: Synthetic Polypeptide

<400> SEQUENCE: 146

Gln Glu His Pro Asn Ala Arg Lys Tyr Lys Gly Ala Asn Arg Arg
1               5                   10                  15

<210> SEQ ID NO 147
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 147

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys
                20                  25                  30

<210> SEQ ID NO 148
<211> LENGTH: 31
<212> TYPE: PRT
<213> ORGANISM: Artificial Sequence
<220> FEATURE:
<223> OTHER INFORMATION: Synthetic Polypeptide

<400> SEQUENCE: 148

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Arg Arg
                20                  25                  30

<210> SEQ ID NO 149
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 149

Ser Leu Arg Arg Ser Ser
1               5

<210> SEQ ID NO 150
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 150

Asn Ser Phe Arg Tyr
1               5

<210> SEQ ID NO 151
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 151

Ser Pro Lys Met Val Gln Gly Ser Gly
1               5
```

```
<210> SEQ ID NO 152
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 152

Met Val Gln Gly Ser Gly
1               5

<210> SEQ ID NO 153
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 153

Lys Val Leu Arg Arg Tyr
1               5

<210> SEQ ID NO 154
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 154

Lys Val Leu Arg Arg His
1               5

<210> SEQ ID NO 155
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 155

Gly Gln His Lys Asp Asp Asn Pro Asn Leu Pro Arg
1               5                   10

<210> SEQ ID NO 156
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 156

Gly Val Pro Gln Val Ser Thr Ser Thr
1               5

<210> SEQ ID NO 157
<211> LENGTH: 15
<212> TYPE: PRT
<213> ORGANISM: Artificial Sequence
<220> FEATURE:
<223> OTHER INFORMATION: Synthetic Polypeptide

<400> SEQUENCE: 157

Gly Glu Arg Ala Phe Lys Ala Trp Ala Val Ala Arg Leu Ser Gln
1               5                   10                  15
```

<210> SEQ ID NO 158
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 158

Gly Gln Pro Arg Glu Pro Gln Val Tyr Thr Leu Pro Pro Ser
1               5                   10

<210> SEQ ID NO 159
<211> LENGTH: 5
<212> TYPE: PRT
<213> ORGANISM: Artificial Sequence
<220> FEATURE:
<223> OTHER INFORMATION: Synthetic Polypepeptide

<400> SEQUENCE: 159

Gly Ala Asn Lys Pro
1               5

<210> SEQ ID NO 160
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 160

Gly Ala Asn Pro Lys
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 161

Gly Ala Asn Pro Gln
1               5

<210> SEQ ID NO 162
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 162

Gly Ala Asn Gln Lys
1               5